United States Patent
Neveu et al.

(10) Patent No.: US 11,458,218 B2
(45) Date of Patent: Oct. 4, 2022

(54) DISINFECTION SYSTEM FOR REUSABLE MEDICAL INSTRUMENTS

(71) Applicant: GERMITEC, Ivry-sur-Seine (FR)

(72) Inventors: Cédric Neveu, Montrouge (FR); Frédéric Lepine, Saint-Gratien (FR); Clément Deshays, Paris (FR)

(73) Assignee: GERMITEC, Ivry-sur-Seine (FR)

(*) Notice: Subject to any disclaimer, the term of this patent is extended or adjusted under 35 U.S.C. 154(b) by 15 days.

(21) Appl. No.: 16/876,765

(22) Filed: May 18, 2020

(65) Prior Publication Data
US 2020/0360549 A1    Nov. 19, 2020

Related U.S. Application Data

(63) Continuation-in-part of application No. PCT/IB2019/000567, filed on May 16, 2019.

(51) Int. Cl.
*A61L 2/10* (2006.01)
*A61L 2/24* (2006.01)

(52) U.S. Cl.
CPC ............ *A61L 2/10* (2013.01); *A61L 2/24* (2013.01); *A61L 2202/11* (2013.01); *A61L 2202/122* (2013.01); *A61L 2202/14* (2013.01); *A61L 2202/24* (2013.01)

(58) Field of Classification Search
CPC .......... A61L 2/10; A61L 2/24; A61L 2202/11; A61L 2202/122; A61L 2202/14; A61L 2202/24
USPC ............................ 250/453.11, 454.11, 455.11
See application file for complete search history.

(56) References Cited

U.S. PATENT DOCUMENTS

| 5,931,557 A * | 8/1999 | Danilychev ............ B01J 19/124 362/234 |
| 2013/0032733 A1 | 2/2013 | Rife |
| 2017/0260681 A1 | 9/2017 | Gao et al. |
| 2018/0117192 A1* | 5/2018 | Baranov ................... A61L 2/10 |

* cited by examiner

Primary Examiner — Nicole M Ippolito
(74) Attorney, Agent, or Firm — B. Aaron Schulman, Esq.; Stites & Harbison, PLLC

(57) ABSTRACT

A disinfection system includes a disinfection chamber and a disinfection device. The disinfection chamber has an interior volume, a plurality of radiation sources, which, when enabled, output a disinfecting radiation, at least one disinfection chamber registration feature, and a disinfection chamber controller arranged to perform a disinfection process via enablement of the plurality of radiation sources. The disinfection tray device has a UV-transparent tray structure, the UV-transparent tray structure having a multi-compartment receptacle shaped to align and contain a certain type of target article to be disinfected.

21 Claims, 18 Drawing Sheets

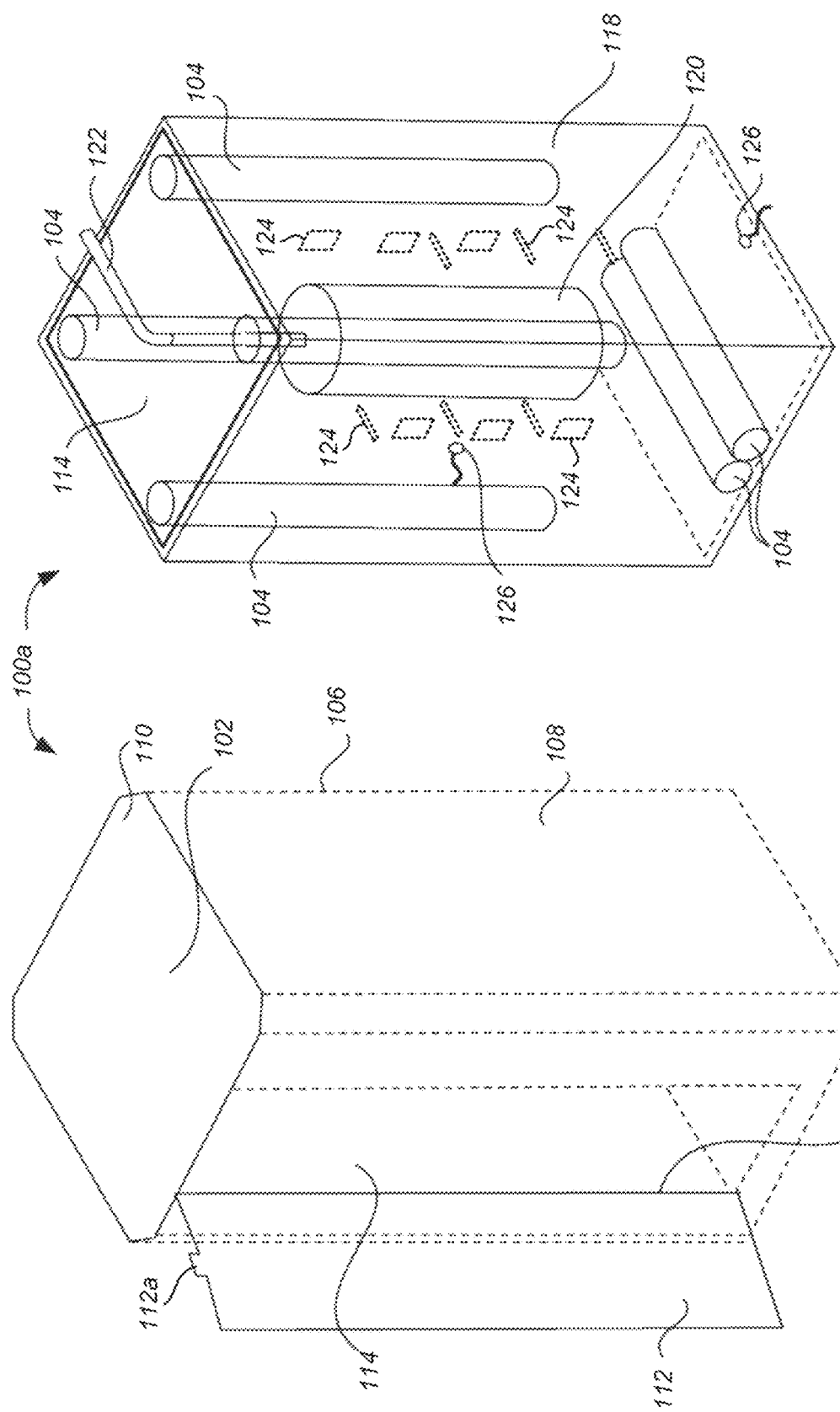

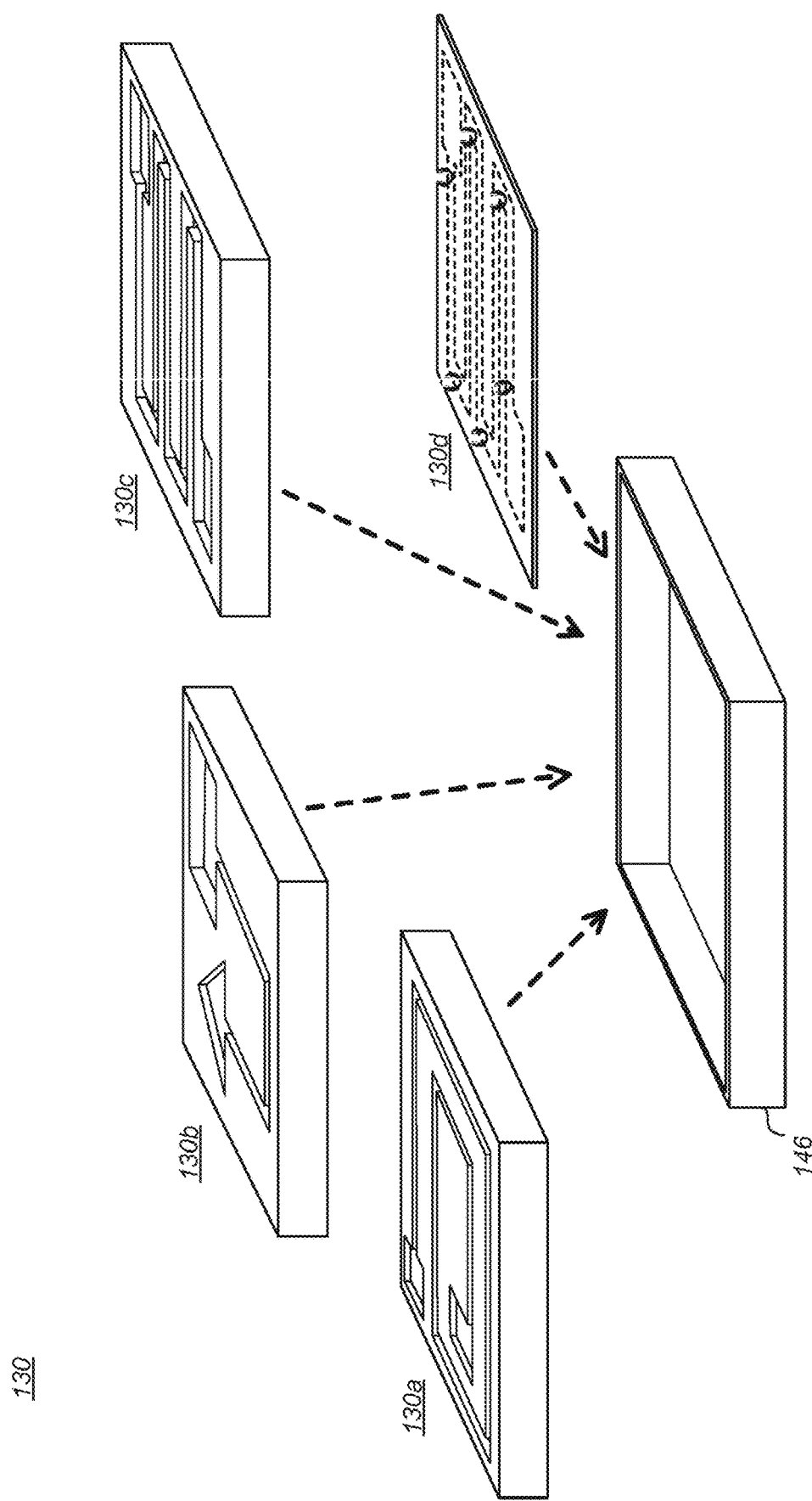

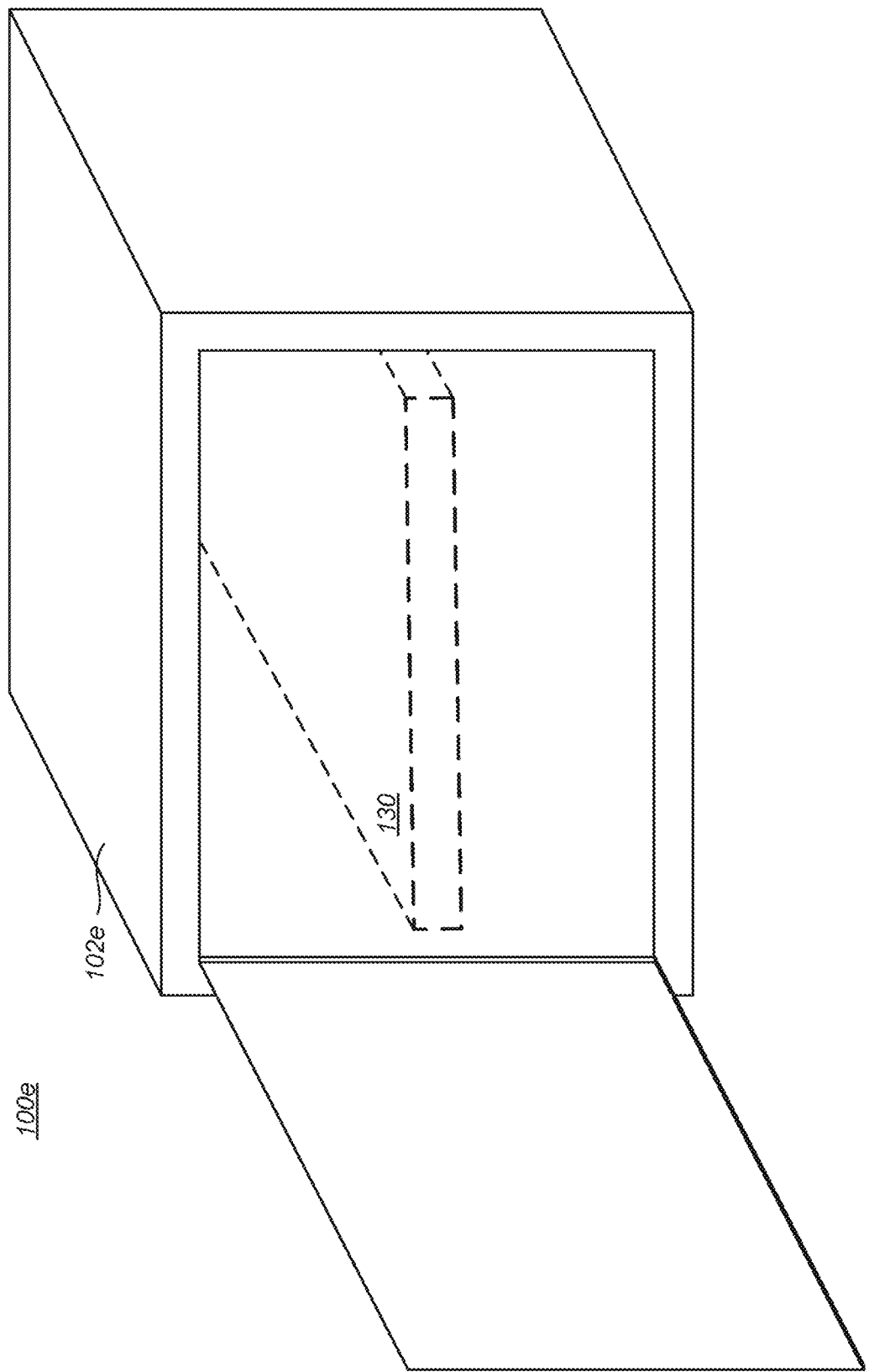

DISINFECTION SYSTEM FOR REUSABLE MEDICAL INSTRUMENTS

CROSS-REFERENCE TO RELATED APPLICATION

This application is a continuation-in-part of International Patent Application PCT/IB2019/000567, filed May 16, 2019, said application hereby incorporated by reference herein.

FIELD OF THE INVENTION

The disclosure is generally directed to devices and systems for disinfecting target articles. More specifically, but not exclusively, the disclosure relates to systems, devices, and methods for containing a target article during an ultraviolet radiation disinfection cycle.

BACKGROUND OF THE INVENTION

Proper disinfection or sterilization of reusable medical instruments is important in preventing the person-to-person transmission of pathogenic microbes. The level of sterilization and disinfection applied to medical instruments depends on how the device is classified. The Centers for Disease Control (CDC) classifies a medical instrument as a critical item, semi critical item, or noncritical item, depending on the intended use of the device (CDC Guideline for Disinfection and Sterilization in Healthcare Facilities, 2008). In the CDC Guideline, it is stated that critical items confer a high risk for infection if they are contaminated with any microorganism.

Examples of critical items are devices that contact sterile tissue and include surgical instruments, implants, and ultrasound probes used in sterile body cavities. These devices must be sterilized prior to use.

Semi critical items typically contact mucous membranes or non-intact skin. Exemplary semi critical items include such devices as probes used in vaginal, rectal, and transesophageal ultrasound exams, equipment for respiratory therapy and anesthesia, and certain endoscopes. These medical devices should be free from all microorganisms; however, some small numbers of bacterial spores are considered permissible. Semi critical items require at least high-level disinfection (HLD).

Noncritical items are those that come in contact with intact skin (e.g., blood pressure cuffs and stethoscopes). In contrast to critical and some semi critical items, most noncritical reusable items may be decontaminated where they are used to achieve intermediate or low levels of disinfection and these items typically do not need to be transported to a central processing area for service.

Because critical items confer a high risk for infection when they are contaminated with any microorganism, they are typically subjected to sterilization processes that kill and remove all microorganisms. Similarly, semi-critical items require high-level disinfection (HLD) where population levels of pathogens are reduced to very low levels prior to or between uses. Some common methods for achieving sterilization or high-level disinfection include treatments using steam and/or chemical disinfectants. Chemical treatments are often used where the article to be treated is heat sensitive, and chemical disinfectants suitable for use in sterilizing or disinfecting medical devices include, for example, glutaraldehyde, hydrogen peroxide, ortho-phthalaldehyde, and peracetic acid with hydrogen peroxide. Currently, some common methods for achieving high-level disinfection of semi-critical medical devices include soaking the devices in a chemical bath. The chemical bath method for semi-critical items may include soaking for shorter periods of time than would be required to assure complete sterilization.

Although effective, there are disadvantages to sterilization and disinfection processes that utilize steam or chemical treatments. For example, the high temperature associated with steam sterilization can damage the instrument being sterilized. Additionally, the chemicals used for chemical sterilization or disinfection are often costly to store and dispose of properly, and their toxicity can present risks to personnel handling them. Furthermore, chemical methods and high heat (i.e., severe heating to high temperatures in steam) systems can cause degradation of the materials used to make the medical device being treated. Steam- or chemical-based processes can also be time consuming with some procedures taking between 15-40 minutes to complete, and these procedures typically require the instrument or device to be removed to a central location for treatment and then returned to the clinical setting. Such prolonged process times remove medical devices from service, which may be a serious problem if the device is used in an Emergency Department setting. Factors such as these can lead to non-compliance with the sterilization or disinfection procedures recommended by the Food and Drug Administration.

Some companies provide devices and systems that can achieve high-level disinfection of target articles that are reusable, in a short time, at a low temperature, and done locally within the clinical setting of use. For example, U.S. Pat. No. 9,364,573, which is incorporated herein by reference, provides a disinfection method and system using a disinfection chamber with a radiation source, wherein high-level disinfection is achieved within 10 minutes (i.e., 600 seconds or less). The temperature within the disinfection chamber is maintained at a low level. One or both of the ambient temperature within the disinfection chamber and the surface temperature of the target article to be disinfected are monitored so that a threshold temperature, e.g., somewhere between 35° C. to 55° C., will be met and will not be exceeded. As another example, U.S. Provisional Patent Application No. 62/776,974, which is incorporated herein by reference, teaches modeling various portions of disinfection systems and target articles to assist high-level ultraviolet disinfection. In at least some cases, devices, systems, and methods are provided to effectively determine and control the disinfection exposure of ultraviolet radiation provided within a disinfection chamber such that a minimum exposure (i.e., minimum dosage) to the radiation is achieved at a target article on each surface portion that is intended for disinfection.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

SUMMARY OF THE INVENTION

The following is a summary of the present disclosure to provide an introductory understanding of some features and context. This summary is not intended to identify key or critical elements of the present disclosure or to delineate the scope of the disclosure. This summary presents certain concepts of the present disclosure in a simplified form as a prelude to the more detailed description that is later presented.

The device, method, and system embodiments described in this disclosure (i.e., the teachings of this disclosure) improve high-level disinfection (HLD) processes. In at least some embodiments, a disinfection tray system is formed having a tray portion with an integrated receptacle. Some or all parts of the tray portion are formed from a material that passes ultraviolet (UV) radiation (i.e., a UV-transparent material). Some or all parts of the disinfection tray system may also be UV-transparent. The integrated receptacle is arranged in a way to fully or partially contain a target article to be disinfected. When the disinfection tray system and target article to be disinfected are placed in a disinfection chamber, UV radiation emitted into the chamber strikes the target article, thereby performing disinfection. Some of the UV radiation passes from a UV source directly to a surface of the target article, and some of the UV radiation passes through the UV-transparent material of the disinfection tray system.

Optionally, disinfection tray system embodiments may include registration features. First registration features, when so included, may be used to align the target article in the disinfection tray portion. Second registration features, when so included, may be used to align the disinfection tray system in the disinfection chamber. Optionally, disinfection tray system embodiments may include an electronics module. The electronics module, when so included, may be arranged to communicate with the disinfection chamber, provide a user interface, and enable other smart features. Optionally, the disinfection tray system embodiments may further include any one or more of handles, covers, cases, compartments, and the like.

In some cases, a suitable disinfection chamber may be arranged as a pass-through disinfection chamber. In these cases, the disinfection chamber may be arranged in a wall or other barrier structure, and the disinfection chamber may provide first access (e.g., a first door) on an unclean side of the barrier to insert the disinfection tray system, and the disinfection chamber may provide second access (e.g., a second door) on a clean side of the barrier to remove the disinfection tray system. In this way, first medical practitioners handling contaminated or other target articles to be disinfected may place the target articles in the disinfection tray, insert the disinfection tray system into the disinfection chamber, and start the disinfection cycle. Other medical practitioners handling disinfected target articles may remove the disinfection tray system from the disinfection chamber after the disinfection cycle has completed.

This Brief Summary has been provided to describe certain concepts in a simplified form that are further described in more detail in the Detailed Description. The Brief Summary does not limit the scope of the claimed subject matter, but rather the words of the claims themselves determine the scope of the claimed subject matter.

The present description deals with a disinfection system for reusable medical instruments, comprising:
a disinfection chamber, the disinfection chamber having:
an interior volume;
at least a radiation source, which, when enabled, output an UV disinfecting radiation;
a disinfection chamber controller arranged to perform an high-level disinfection process via enablement of the at least one radiation source; and
a UV-transparent receptacle device for allowing at least a part of at least an instrument to be disinfected, to lay in an adapted position for an high-level disinfection.

According to some particular embodiments, the disinfection system comprises one or more of the following features:
the disinfection device further comprises a plurality of radiation sources.
the disinfection device further comprises at least one disinfection chamber registration feature.
the disinfection device further comprises at least one disinfection tray registration feature, the at least one disinfection tray registration feature arranged to cooperate with the at least one disinfection chamber registration feature when the disinfection tray device is placed in the disinfection chamber.
the at least one disinfection tray registration feature is a non-electronic, physical structure.
a proper alignment of the disinfection tray device in the disinfection chamber is indicated via tactile feedback.
the at least one disinfection tray registration feature is an electronic registration feature.
a state of proper alignment or improper alignment of the disinfection tray device in the disinfection chamber is indicated via at least one of an audible output and a visual output.
the disinfection chamber is arranged to concurrently hold a plurality of disinfection devices.
the disinfection tray device is arranged to align and contain the at least target instrument to be disinfected.
the disinfection chamber device further comprises:
a door; and
door sensor, wherein the disinfection chamber controller is arranged to determine when the door is closed and wherein the disinfection chamber controller is further arranged to prevent and suspend the disinfection process when the door sensor indicates that the door is open.
the disinfection chamber device further comprises:
a second door; and
a second door sensor, wherein the disinfection chamber controller is arranged to determine when both the door and the second door are closed and wherein the disinfection chamber controller is further arranged to prevent and suspend the disinfection process when the door sensor indicates that the door is open or when the second door sensor indicates that the second door is open.
the disinfection chamber device further comprises:
a first door lock mechanism arranged to lock the door and arranged to unlock the door; and
a second door lock mechanism arranged to lock the second door and arranged to unlock the second door, wherein the disinfection chamber controller is arranged to:
determine a pre-disinfection state, said pre-disinfection state being a first time before the disinfection process begins;
determine a current disinfection state, said current disinfection state being a second time when the disinfection process has started and the disinfection process has not completed;
determine a post-disinfection state, said post-disinfection state being a third time when the disinfection process has completed;

unlock the door during the pre-disinfection state;
lock the second door during the pre-disinfection state;
lock both the door and the second door during the current disinfection state;
lock the door during the post-disinfection state; and
unlock the second door during the post-disinfection state.

the disinfection chamber is integrated into a wall.

a first side of the wall exposes the door and wherein a second opposing side of the wall exposes the second door, said first side of the wall being a pre-disinfected side of the wall and said second side opposing side of the wall being a post-disinfected side of the wall.

the disinfection device further comprises a disinfection controller, the disinfection controller arranged to communicate identification information to the disinfection chamber controller, the identification information representing at least one of the UV-transparent structure and the certain type of target article to be disinfected.

the disinfection chamber controller is further arranged to select the disinfection process from a plurality of disinfection processes based on the identification information.

the disinfection chamber controller is further arranged to control the disinfection process based on the identification information.

the disinfection chamber controller is further arranged to selectively enable a first one of the plurality of radiation sources and concurrently a disable a second one of the plurality of radiation sources during the disinfection process based on the identification information.

the disinfection chamber controller is further arranged to:
generate metadata based on the disinfection process; and
communicate at least some of the metadata to a remote computing device.

the metadata includes user identification information representing an identity of a user that initiated the disinfection process.

the metadata includes timestamp information representing a date when the disinfection process was executed.

the disinfection chamber controller is further arranged to generate an expiration date associated with the disinfection process.

the disinfection device further comprises at least one electronic radiation sensor integrated into a surface of the disinfection device.

the disinfection chamber controller is further arranged to disable the at least one radiation source based on information from the at least one electronic radiation sensor.

the disinfection device further comprises:
a first electronic radiation sensor integrated into a surface of the disinfection device at a first location proximal to a first receptacle portion of the UV-transparent structure; and
a second electronic radiation sensor integrated into the surface of the disinfection device at a second location proximal to a second receptacle portion of the UV-transparent structure.

the disinfection chamber controller is further arranged to:
selectively enable and disable a first one of the plurality of radiation sources based on information from the first electronic radiation sensor; and
selectively enable and disable a second one of the plurality of radiation sources based on information from the second electronic radiation sensor.

The present description also relates to a disinfection device, comprising:
a portion formed from a UV-transparent material, the portion having a receptacle arranged therein to receive a target article to be disinfected, wherein the receptacle has a first defined shape and a first defined dimension; and
an alignment portion having a second defined shape and a second defined dimension.

According to some particular embodiments, the disinfection device comprises one or more of the following features:
the receptacle is arranged to receive only a portion of the target article to be disinfected.
the second defined shape is a cuboid.
the UV-transparent material includes at least one of a plastic, a glass, a gel, a polymer, a polymethyl methacrylate (PMMA), and a polystyrene.
the tray portion is arranged for use a single time.
the disinfection device is a disposable device.
the tray portion is at least 50 percent (50%) UV-transparent.
the tray portion is at least 75 percent (75%) UV-transparent.
the tray portion is at least 95 percent (95%) UV-transparent.
the tray portion is a molded structure, a blow-molded structure, a laser-cut structure, or a heat-formed structure.
the disinfection device comprises at least two handle attachment structures.
the disinfection device comprising at least two handles, wherein each of said at least two handles is arranged for removable coupling to a corresponding handle attachment structure.
the alignment portion includes at least one registration feature.
the at least one registration feature is an electronic registration feature.
the electronic registration feature includes at least one time-of-flight sensor or at least one photo-diode.
the disinfection device comprises a lid arranged to cover at least the receptacle.
the disinfection device comprises at least one UV sensor.
the disinfection device comprises an electronics module, the electronics module having;
a communications interface;
a user interface; and
at least one clean/not clean indicator.
the electronics module is hermetically sealed in the device portion.
the electronics module is arranged to communicate identification information associated with the target article to be disinfected from the disinfection device to a disinfection system.
the disinfection device comprises a mechanically sealable case arranged to hold at least one device portion, the mechanically sealable case arranged to store the at least one target article to be disinfected.

The present description also deals with a disinfection method, comprising:
arranging a target article to be disinfected in a receptacle device having at least one pre-formed receptacle arranged therein to receive the target article, wherein the receptacle device is formed at least in part from a UV-transparent material;

arranging the receptacle device in a disinfection chamber, wherein arranging the receptacle device includes cooperatively aligning a registration feature of the receptacle device with a corresponding registration feature of the disinfection chamber; and executing a UV-based disinfection process within the disinfection chamber.

According to some particular embodiments, the disinfection method comprises one or more of the following features:

the disinfection method comprises:
  determining a misalignment condition, said determining the misalignment condition by:
    electronically determining whether or not the target article to be disinfected is properly aligned in the at least one pre-formed receptacle; or
    electronically determining whether or not the receptacle device is properly aligned in the disinfection chamber; and
    providing an output indication representing the misalignment condition.

the disinfection method comprises:
  determining a misalignment condition, said determining the misalignment condition by
    visually determining whether or not the target article to be disinfected is properly aligned in the at least one pre-formed receptacle; and
    tactilely determining whether or not the receptacle device is properly aligned in the disinfection chamber.

the disinfection method comprises:
  communicating identification information to the disinfection chamber, the identification information representing at least one of the receptacle device and the target article to be disinfected; and
  using the identification information to select the UV-based disinfection process.

the disinfection method comprises:
  generating metadata associated with the disinfection process; and
  communicating the metadata to a remote computing device.

the metadata includes at least one of: time information representing when the disinfection process was executed, date information representing when the disinfection process was executed, and user identification information.

the metadata includes date information representing when the disinfection will expire.

the disinfection method comprises extending the disinfection process based on accumulated radiation information derived from at least one radiation sensor.

the disinfection method comprises individually controlling a plurality of radiation sources in the disinfection chamber based on at least one of the receptacle device and the target article to be disinfected, wherein individually controlling the plurality of radiation sources includes directing a first radiation source to output radiation for a first period of time and directing a second radiation source to output radiation for a second period of time, the first period of time being different from the second period of time.

arranging the target article to be disinfected in the receptacle device having at least one pre-formed receptacle includes aligning the target article to be disinfected on a surface of the receptacle device according to a template printed on the surface of the receptacle device.

the at least one pre-formed receptacle includes a plurality of clips arranged to bind certain portions of the target article to be disinfected.

the disinfection method comprises verifying disinfection of the target article to be disinfected after executing at least a portion of the UV-based disinfection process.

the verifying includes sensing UV-radiation with at least one radiation sensor associated with the receptacle device.

the registration feature of the receptacle device and the corresponding registration feature of the disinfection chamber are formed at least in part by electronic devices.

the electronic devices are arranged to form an optical connection, a wireless radio connection, an electromagnetic connection, or an inductive connection.

the disinfection method comprises removing at least one handle structure from the receptacle device after arranging the receptacle device in the disinfection chamber.

The present invention also deals with a disinfection system for reusable medical instruments, comprising:
  a disinfection chamber, the disinfection chamber having:
    an interior volume;
    at least one radiation source, which, when enabled, output an UV disinfecting radiation, the at least one radiation source being suitable for emitting sufficient UV disinfecting radiation to carry out high-level disinfection;
    a disinfection chamber controller configured to perform an high-level disinfection process via enablement of the at least one radiation source; and
  a disinfection tray device suitable to be placed into the disinfection chamber, the disinfection tray device comprising at least one UV-transparent receptacle for receiving at least a part of at least an instrument to be disinfected, the at least one UV-transparent receptacle being arranged for a specific orientation and placement of an instrument to be disinfected.

According to some particular embodiments, the disinfection system comprises one or more of the following features:

the disinfection tray device comprises at least one first registration feature, the at least one first registration feature enabling the alignment of the instrument to be disinfected into the at least one UV-transparent receptacle.

the at least one first registration feature is a non-electronic, physical structure, such as a template printed on the surface of the UV-transparent receptacle.

the at least one registration feature is an electronic registration feature.

the disinfection chamber comprises at least one disinfection chamber registration feature, the disinfection tray device comprising at least one second disinfection tray registration feature, the at least one second disinfection tray registration feature being configured to cooperate with the at least one disinfection chamber registration feature when the disinfection tray device is placed in the disinfection chamber.

the at least one second registration feature and/or the at least one disinfection chamber is a non-electronic, physical structure.

the disinfection tray device further comprises a disinfection controller, the disinfection controller being arranged to communicate identification information to the disinfection chamber controller, the identification information representing at least one of the UV-transparent receptacle and the certain type of instrument to be disinfected.

the disinfection chamber controller is further arranged to select the disinfection process from a plurality of disinfection processes based on the identification information.

the disinfection chamber controller is further arranged to control the disinfection process based on the identification information.

the disinfection device further comprises at least one electronic radiation sensor integrated into a surface of the disinfection device.

the disinfection chamber controller is further arranged to disable the at least one radiation source based on information from the at least one electronic radiation sensor.

the disinfection tray device further comprises:
a first electronic radiation sensor integrated into a surface of the disinfection tray device at a first location proximal to a first receptacle portion of the UV-transparent receptacle; and
a second electronic radiation sensor integrated into the surface of the disinfection tray device at a second location proximal to a second receptacle portion of the UV-transparent receptacle.

the disinfection chamber comprises a plurality of radiation source, the disinfection chamber controller being further arranged to:
selectively enable and disable a first one of the plurality of radiation sources based on information from the first electronic radiation sensor; and
selectively enable and disable a second one of the plurality of radiation sources based on information from the second electronic radiation sensor.

the disinfection system comprises an element suitable for verifying a proper alignment of the disinfection tray device in the disinfection chamber and/or a proper alignment of the instrument to be disinfected into the UV-transparent receptacle, the element being suitable for analyzing data from a sensor.

the disinfection chamber controller is configured to enable the at least one radiation source so as to emit a dose of radiation comprised between 10 Millijoules per square centimeter and 10 Joules per square centimeter for a duration comprised between 10 seconds and 10 minutes.

the disinfection chamber controller is configured to create a plurality of disinfection regions within the interior volume, the disinfection chamber controller being configured to enable the at least one radiation source in order to irradiate the disinfection regions at a varying radiation intensity, at least one region being irradiated two or three time the radiation intensity of another region.

the UV-transparent receptacle is arranged such that the instrument to be disinfected is oriented substantially horizontally in the disinfection chamber, when the disinfection tray device is positioned into the disinfection chamber.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIGS. 1A-1C are exemplary disinfection chambers embodiments of the types that may be used in cooperation with disinfection tray systems described herein;

FIGS. 5A and 5B are optional container portions that may be arranged as part of a disinfection tray system;

FIGS. 6A-6E are disinfection system embodiments arranged to receive any one or more of the disinfection tray embodiments taught in the present disclosure;

DETAILED DESCRIPTION OF THE INVENTION

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

The device, method, and system embodiments described in this disclosure (i.e., the teachings of this disclosure) improve high-level disinfection (HLD) processes. The present disclosure will describe, in detail, certain disinfection tray systems, certain tray portions, certain integrated receptacles, and particular materials that pass determined ultraviolet (UV) radiation (i.e., a UV-transparent material). The present disclosure will also describe certain electronic modules and capabilities of such modules, registration features, handles, covers, cases, and other such features, and the present disclosure will describe certain disinfection chamber embodiments.

Figure 1C:
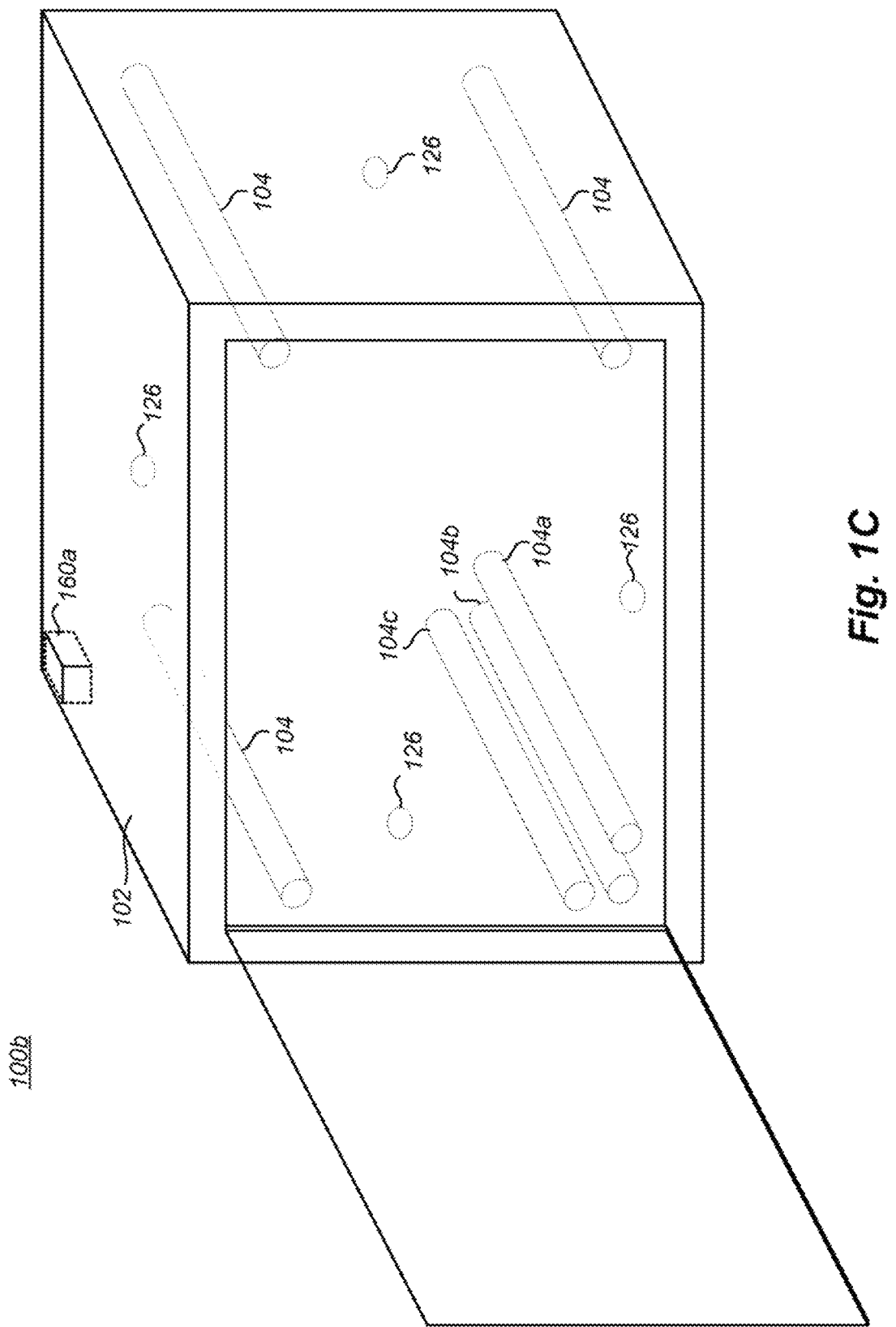

FIGS. 1A-1C are exemplary disinfection chamber embodiments of the types that may be used in cooperation with disinfection tray systems described herein. FIGS. 1A-1C may be collectively referred to herein as FIG. 1. The present disclosure includes a first disinfection system 100*a* embodiment in FIGS. 1A-1B, a second disinfection system 100*b* embodiment in FIG. 1C, and various other disinfection system 100*c*-100*g* embodiments in other figures. To simplify the present disclosure, the disinfection systems 100*a*-100*g* may be referred to herein as a disinfection system 100. Where specific features of a disinfection system 100*a*-100*g* embodiment are discussed, the relevant figure and embodiment of interest will be specifically identified.

In FIGS. 1A-1B, disinfection system 100a is a high-level disinfection device that includes a disinfection chamber 102 and one or more radiation sources 104. Disinfection chamber 102 includes a housing 106 having a plurality of sidewalls 108, a top 110, and a door 112 disposed within one of the sidewalls 108 for accessing the interior volume 114. The door 112 in FIG. 1A includes an interlock mechanism 112a, which may be used to verify the open or closed position of the door, to affirmatively lock the door closed during a disinfection cycle, or for other purposes. Although the door 112 in FIG. 1A is shown as being rotatably movable about a vertical axis, other door configurations may be used, so long as they provide adequate access to the interior volume 114. It is understood that upon opening door 112, an access opening 116 is created in the disinfection chamber sidewall 108, and the access opening 116 communicates with the interior volume 114. Other arrangements of disinfection chambers are of course contemplated.

The interior volume 114 of the disinfection chamber 102 may include one or more reflective surfaces 118 arranged to facilitate reflections of radiation light rays emitted from radiation sources 104 such that a rapid and low temperature disinfection is achieved. The reflective surface is typically formed from one or more materials having at least 30% reflectivity. By "at least 30% reflectivity," it is meant that no more than 70% of the incident UV radiation, particularly in the UV-C range, will be absorbed, and the rest of the incident radiation will be reflected via one or both diffuse and specular reflection. Reflective materials that may be particularly useful in a disinfection chamber include, but are not limited to, aluminum, glass, magnesium, stainless steel, polyvinyl alcohol, polytetrafluoroethylene, substrate materials treated with barium sulfate-containing paints, and alloys, derivatives, and copolymers thereof. In some variations, the reflective surface comprises aluminum, polished to a "Grand Brilliant" condition. In other variations, the reflective surface may be formed using polytetrafluoroethylene PTFE, or PTFE and similar polymers may be coated by various means onto another substrate, to form the reflective surface. In particular embodiments, the reflective interior surfaces of the disinfection chamber are formed to be as reflective as available manufacturing techniques provide. Such an approach facilitates disinfection processes that utilize high intensity disinfection radiation carried out at low temperatures.

The interior reflective surfaces 118 of the interior volume 114 may be positioned and shaped to reduce the absorption of UV radiation by the interior surfaces 118 and instead reflect and redirect the UV radiation within the interior volume 114 of disinfection chamber 102 and onto the one or more target articles 120 positioned within the interior volume 114. The material choice and configuration of the interior volume 114 of disinfection chamber 102 may be selected to promote preferential extinction of certain UV or other wavelengths of electromagnetic energy that can contribute to increased temperatures within the interior volume 114 (i.e., longer wavelengths of radiation). That is, the shape of the interior volume 114 may contribute to the quick and efficient directing of radiation to the target article 120. For example, it may be configured that the radiation passing through the middle of the interior volume 114 of the disinfection chamber 102, where the target article 120 is to be positioned, and the reflective material(s) employed in the interior volume 114 may contribute to the reflection (e.g., re-radiation or re-emission) of radiation with low loss (i.e., approximately the same amount of energy returns from the surface as was incident). In particular embodiments, the interior walls of the interior volume 114 are constructed and configured to provide low loss of UV-C radiation emitted from the one or more UV radiation sources 120 (not specifically shown in FIG. 1A for simplicity purposes). Such embodiments increase the likelihood that UV-C radiation useful for disinfection will be reflected one or more times inside the interior volume 114 of the disinfection chamber 102 until the radiation impinges upon the target article 120 to be disinfected where it may be absorbed and extinguished, reflected, or re-emitted. In this way, for a given amount of total energy released into the disinfection chamber 102, which also may include some amount of infrared or heat energy, an improved utility is made of the useful UV-C band energy in disinfecting the target article 120 (e.g., medical device, dental instrument, electronic component, or any other target article to be disinfected), while reducing the amount of thermal heating of the target article 120.

Figure 7:
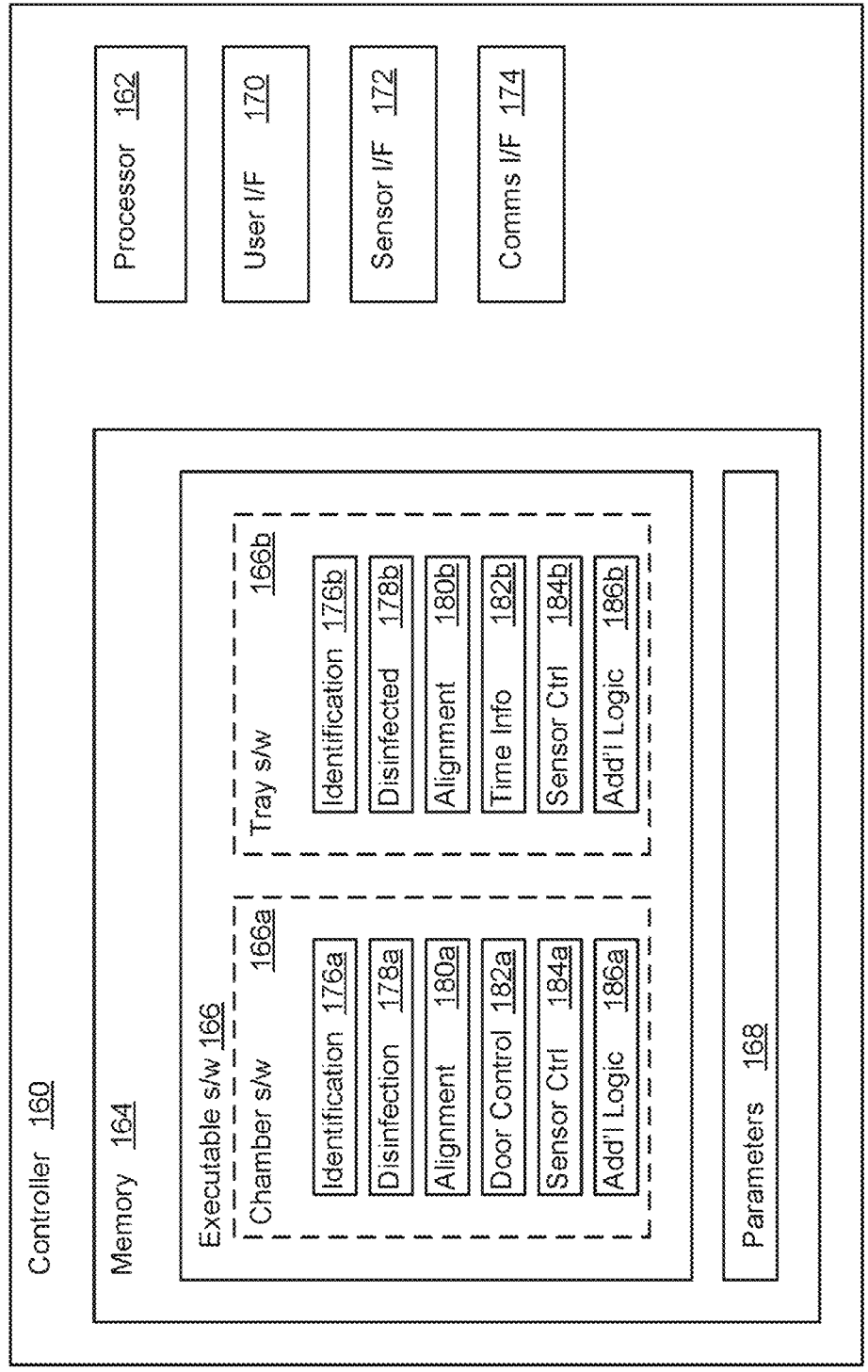
FIG. 7 is an exemplary controller.

In particular embodiments, a suspension assembly 122 may be provided that positions a target article 120 in a central portion, or other desired portion, of the disinfection chamber 102, where a disinfection region of high-intensity radiation is created. In some variations, for instance, when the target article 120 is connected to a cable that may then extend into the interior volume 114 of the disinfection chamber 102, the suspension assembly 122 comprises a slot at the top of the assembly that extends to a central portion of the top 110 of the disinfection chamber 102. In some cases, the suspension assembly 122 may include one or more control mechanisms arranged to receive control signals from a processing device such as an electronic control module 160 (FIG. 7). In these or other cases, the suspension assembly 122 may operate according to a generated disinfection program to adjust the position of a target article 120 in the disinfection chamber 102 in two dimensions (e.g., up, down, left, right), three dimensions (e.g., rotation, lateral motion), four dimensions (e.g., time dependent, motion during a disinfection cycle), or some other number of dimensions. In some cases, a suspension assembly 122 includes registration features 124 to help align a target article 120. In some cases, a suspension assembly 122 is permanently or semi-permanently fixed such that the target article 120, once placed in the interior volume 114 of the disinfection chamber 102, does not move during a disinfection cycle.

In various embodiments, any number of registration features 124 are arranged at suitable locations within the disinfection chamber 102. In FIG. 1B, for example, twelve registration features 124 are shown. In other embodiments, a different number of registration features 124 may be included. The registration features will be sized, shaped, located, or otherwise arranged to cooperate with corresponding registration features of disinfection tray systems 130 (FIG. 3) positioned in the interior volume 114 of the disinfection chamber 102. In the embodiment of FIG. 1B, some of the registration features 124 are arranged normal to each other, and some of the registration features 124 are opposing each other. In addition, registration features 124 of FIG. 1B are formed on each of four internal sidewalls 108 of the disinfection chamber 102. In still other embodiments, more or fewer registration features 124 are arranged, and the registration features 124 may be formed at the top of the disinfection chamber 102, the bottom of the disinfection chamber 102, or some other portion of the disinfection chamber 102. In some cases, zero or only one registration feature 124 is arranged in the disinfection chamber 102. In some cases, one or more registration features 124 are movable structures that can be arranged at a first location for a first disinfection cycle and arranged at a second, different location for a second disinfection cycle.

As detailed herein, the disinfecting radiation utilized can be UV-C radiation, and in embodiments that utilize UV-C radiation, the one or more radiation sources 104 may be any commercially available device suitable for emitting sufficient UV-C radiation to carry out high-level disinfection. Where one source 104 of UV-C radiation is coupled to the disinfection chamber 102, that source 104 will emit sufficient UV-C radiation to carry out high-level disinfection. Where two or more sources of UV-C radiation are coupled to the disinfection chamber 102, the UV-C radiation sources 104 may each be capable of emitting sufficient UV-C radiation to carry out high-level disinfection. Alternatively, in embodiments of the system 100 including two or more UV-C sources 104 coupled to interior volume 114 of disinfection chamber 102, such radiation sources 104 may each, on their own, emit insufficient UV-C radiation to achieve high-level disinfection, but when the individual outputs of UV-C radiation emitted from the two or more sources 104 are combined, the total output of UV-C radiation is sufficient to achieve high-level disinfection.

Radiation source 104 may be coupled to interior volume 114 through various approaches. For example, radiation source 104 may be locally attached to interior volume 114 to emit UV-C radiation rays into interior volume 114, as shown in FIG. 1B for illustrative purposes. In further examples, a radiation source 104 may be remotely coupled to interior volume 114. For example, radiation source 104 may be a standard laser, or solid state laser photodiode, and may be employed as a source of disinfecting energy for a stand-alone disinfection chamber 102, along with appropriate optical conductors and couplers to emit UV-C radiation rays into interior volume 114. Further, in some embodiments, a direct or conducted source of UV radiation could be steered, via a mirror or other device, or scanned along a target article 120 positioned within interior volume 114. In other embodiments, disinfection chamber 102 may include a moveable attachment assembly, which is not specifically shown to avoid unnecessarily cluttering the figure, within interior volume 114 such that a target article 120 may be positioned on the moveable base and may be moved past a stationary radiation emission region. An electronic control module (e.g., controller 160 of FIG. 7) may control the radiation source 104 and the moveable base to rotate or move in opposite directions to provide preferential exposure of the target article 120 to the UV radiation.

Though the devices, methods, and systems provided herein are primarily described with reference to UV-C radiation as the disinfecting radiation within the disinfection chamber, this is for illustrative purposes only. The radiation or energy used in the disinfection system 100 may also be or include UV-A radiation, UV-B radiation, or even non-UV radiation, alone or in various combinations. It is to be further understood that, within the interior volume 114, exposure of the articles to UV radiation may be carried out in a variety of ways.

Instead of UV radiation, such as UV-C radiation, some variations of the devices taught herein may use a flash source of energy. A flash source of energy emits extremely high intensity disinfecting radiation. The flash source of energy can provide high-level disinfection of one or more contaminated articles in an acceptably short period of time. In certain embodiments, a flash source of energy may deliver disinfecting radiation to the one or more articles at such a high rate that high-level disinfection is achieved in period of time selected from 10 seconds or less, 5 seconds or less, 3 seconds or less, and 2 seconds or less. A flash source of energy as contemplated herein may be selected to deliver any selected disinfecting radiation. For instance, a disinfection system as described herein may include a flash source of energy that emits electron beam, gamma-ray, x-ray, gas-plasma, or UV-C radiation. The biologically active mechanism of disinfection of the flash source may be different for the different sources. For example gamma-ray may fully kill a pathogen, whereas UV-C may leave the pathogen alive but biologically sterile and unable to reproduce.

Where a flash source of energy is used, one radiation source 104 of disinfecting radiation may be all that is needed in the interior volume 114 of disinfection chamber 102. In such embodiments, to achieve generally homogenous or uniform radiation exposure on the target article 120, the radiation emitted by the flash source may first strike a surface that will spread and distribute the radiation before hitting the target. In this case, the target will receive primarily indirect rather than direct, illumination. In other words, the disinfection device could be configured so that the radiation source 104 or radiation sources 104, of any appropriate type, are located in a different part of the disinfection chamber 102 than the target article 120. Since the energy spectrum emitted by some types of flash sources may be broad, a filter (not shown) may be interposed in some cases between the radiation source 104 and the target article 120 so only the spectrum of interest is allowed to pass to the interior volume 114. The filter may serve to reduce the presence within the chamber of infrared energy, which does not disinfect but will otherwise heat the disinfection chamber 102 and thus raise its temperature and that of objects contained therein. Said filters may also be useful when implemented with the other radiation sources mentioned herein. Combinations of disinfection energy sources may be used in the devices and systems described herein. Where two or more different disinfection energy sources are used, they may be applied sequentially, in parallel, or in various combinations and orders. The inclusion and use of two or more different sources of disinfecting energy may prove advantageous in situations where certain pathogens are more susceptible to a particular source of disinfection energy, and in order to reduce overall exposure of the target article 120, it may be useful to employ a variety of radiations sources, durations, and doses to achieve acceptable disinfection for pathogens of interest.

Where the devices and systems described herein utilize UV radiation, such as UV-C radiation, the one or more UV radiation sources 104 and/or the one or more UV radiation sensors 126 are positioned within the interior volume 114 of disinfection chamber 102 in a manner that facilitates rapid, low temperature disinfection. In general, the configuration of the disinfection chamber 102, the sources of disinfecting radiation, and the sensors detecting disinfecting radiation will be selected to provide and confirm a selected exposure of the one or more articles to radiation and/or optimize transmission of radiation from the one or more sources to efficiently and reproducibly target an article.

As described, a disinfection chamber 102 according to the present disclosure may be coupled to a single radiation source 104 of disinfecting radiation, such as one UV-C radiation source. In such embodiments, the radiation source may be positioned on a top or bottom of the chamber. Alternatively, depending on the positioning of the target articles 120 to be disinfected, the single radiation source 104 may be positioned on a side of the disinfection chamber or, where the disinfection chamber includes multiple sides, at an intersection formed at an intersection of two sides. However, the devices and systems described herein are not limited to disinfection chambers having a single source of disinfecting radiation.

The disinfection chamber 102 included in the systems, devices, and methods of the present disclosure may utilize multiple radiation sources 104, of the same or different variety, and different embodiments of a disinfection chamber 102 having multiple sources 104 of disinfecting radiation are detailed herein and illustrated in the accompanying figures. Such embodiments may be advantageous where the respective surfaces of the one or more target articles 120 to be disinfected are more complex than a single flat surface. For example, a target article 120 to be disinfected, such as an endotracheal probe or an ultrasound probe, may have two or more of a front, back, lateral, and dorsal and/or ventral surface that require disinfection. In such a scenario, it may be difficult to deliver high intensity radiation to each surface of target article 120 with a single source or type of disinfecting radiation. Accordingly, in some embodiments of the disinfection devices systems 100 described herein, the radiation sources 104, and other structures are arranged to disinfect one particular type of target. That is, the radiation sources 104 and/or other structures may provide illumination to each surface of the specific target article 120, but the device would not function effectively if a different type of target article 120 was placed in the disinfection chamber 102.

Radiation sources 104 that may be employed in devices and systems as described herein are available in the art, and include, for example, UV-C emitting lamps. UV-C emitting lamps, which may also be referred to herein as "tubes," are available commercially from various sources, including Philips Lighting B.V., and can be obtained in different shapes, sizes, input energy, and UV-C output ratings. Suitable UV-C tubes for use as a UV-C energy source include low-pressure mercury vapor discharge lamps. However, the disinfection chambers are not limited to a particular UV-C source. Any source capable of emitting UV-C light within the selected UV-C wavelength at an output rating that contributes to the disinfection of a target article 120 could be used in the devices disclosed herein. For example, in addition to or as an alternative to one or more UV-C tubes, one or more lasers or photodiodes, or arrays of sources, or combinations of types of sources designed to emit UV-C light may be used to deliver disinfecting radiation within the disinfecting chamber.

In particular embodiments, the one or more sources of UV-C radiation included in the disinfection chambers 102 described herein provide a total UV-C output within the interior volume 114 of the disinfection chamber 102 that is selected to be at least 5 Watts of radiant power. Selection of such a radiation source, which can deliver a high-power dose of radiation, may be preferred to shorten a disinfection cycle. That is, by selecting a high-power radiation source, the energy is delivered rapidly, which may reduce the duration of radiation exposure and also reduce the amount of heat generated by the radiation. In other cases, the one or more radiation sources 104 may be selected to provide a total UV-C output within the chamber's interior volume 114 selected from at least 10 W, at least 15 W, at least 20 W, at least 25 W, at least 30 W, at least 40 W, at least 50 W, at least 75 W, at least 90 W, and at least 100 W of radiant power. Where UV-C sources are used as the one or more sources 104 of disinfecting radiation, the frequency band of UV-C light emitted from the one or more sources may be selected from between about 240 nm and about 270 nm and between about 255 nm and about 265 nm. In other cases, radiation sources 104 may output UV-A radiation (e.g., 320-400 nm), UV-B radiation (e.g., 280-320 nm), or some other form of radiation such as UV-C radiation (e.g., 100-280 nm).

FIG. 1C is another disinfection system 100b embodiment along the lines of the disinfection systems 100a of FIGS. 1A-1B. Certain features of the disinfection system 100b that are common to other disinfection systems 100 in the present disclosure are not identified so as to avoid unnecessarily crowding the drawings.

As evident in the embodiment of FIG. 1C, various disinfection systems 100 may be arranged having any suitable size, shape, and dimension. Various disinfection systems 100 may include any number of doors, door positions, door shapes, door sizes, and the like. Various disinfection systems 100 may include any number of radiation sources 104, radiation source configurations, and control mechanisms for such radiation sources.

In the disinfection system 100b, a plurality of radiation sources 104, 104a, 104b, 104c are positioned at various locations in the disinfection chamber. In the exemplary embodiment of FIG. 1C, three radiation sources 104 are located in three opposing "corners" of the disinfection chamber, and three different radiation sensors 104a, 104b, 104c are located in a fourth opposing corner of the disinfection chamber. In the embodiment of FIG. 1C, when all of the radiation sources 104, 104a, 104b, 104c are operating concurrently, it can be expected that the portion of the disinfection chamber proximate to the three radiation sources 104a, 104b, 104c will receive an increased amount of radiation relative to other portions of the disinfection chamber. By arranging a more or fewer radiation sources in a first portion of a disinfection chamber, the amount of radiation in that first portion of the disinfection chamber may be more or less than in other portions of the chamber. In addition, by selectively operating various ones of the radiation sources 104, 104a, 104b, 104c, the amount of radiation in one portion of a disinfection chamber may be desirably increased or decreased relative to other portions of the disinfection chamber.

The radiation sources 104, 104a, 104b, 104c may have any suitable dimensions, configurations, and operating parameters. Any or all of the radiation sources 104, 104a, 104b, 104c may be alike or different from others of the radiation sources 104, 104a, 104b, 104c. For example, in the exemplary embodiment of FIG. 1C, each of radiation sources 104a, 104b, 104c has a similar size and configuration to radiation sources 104. In other cases, radiation sources 104a, 104b, 104c may be combined into a single, larger radiation source (not shown). To simplify the discussion in the present disclosure, any one or more of the radiation sources 104, 104a, 104b, 104c may be referred to herein as a radiation source 104.

In the disinfection system 100b embodiment of FIG. 1C, a plurality of radiation sensors 126 are positioned at various locations in the disinfection chamber. The locations may be arranged so that one or more radiation sensors 126 receive radiation from one or more radiation sources 104. The radiation sources 104, 104a, 104b, 104c may be arranged symmetrically, asymmetrically, or in any other pattern. The radiation sources may be illuminated in concurrently, randomly, sequentially, or according to some other illumination scheme.

A controller 160a is arranged to direct operations of the disinfection system 100. The controller 160a may in some cases control the operating and communication parameters of the radiation sensors 126. In these and other cases, the controller 160a will also direct the operations of the radiation sensors 126 and receive radiation sensor data from the radiation sensors 126. The radiation sensor data may, for example, include numerical information that represents or otherwise indicates how much radiation has reached the respective radiation sensor 126. The controller 160a will also direct the operations of the radiation sources 104. The controller 160a may provide or otherwise direct one or more of the radiation sources 104 to output radiation based on radiation sensor data from one or more of the radiation sensors 126. In at least some cases, the controller 160a directs the operations of the radiation sources 104 and radiation sensors 126 based a software program formed by a set of computer executable instructions that are executed by the controller 160a.

Figure 2A:
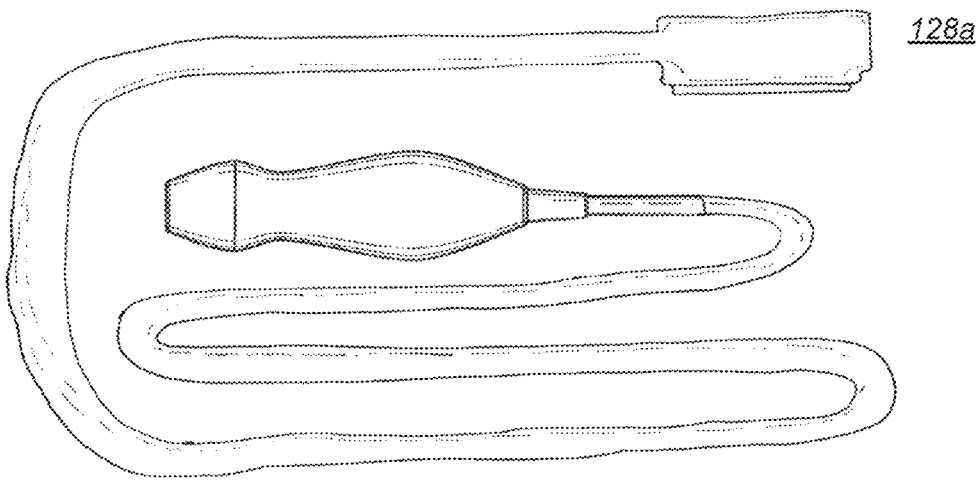
FIGS. 2A-2C are exemplary medical probes of the types that may be used in cooperation with disinfection tray systems described herein.
Figure 2B:
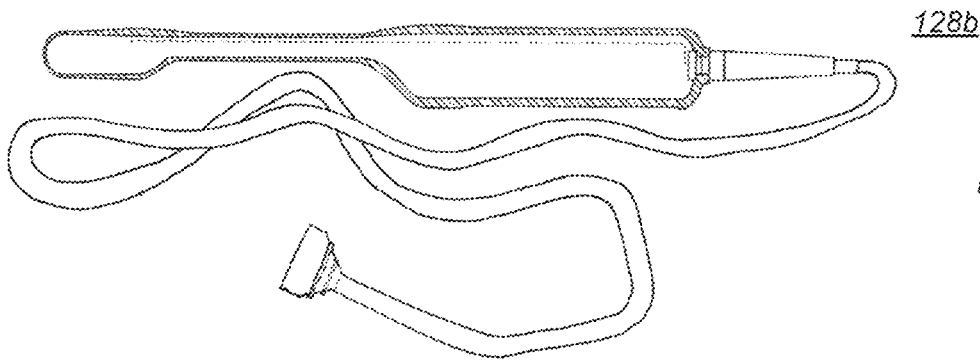
Figure 2C:
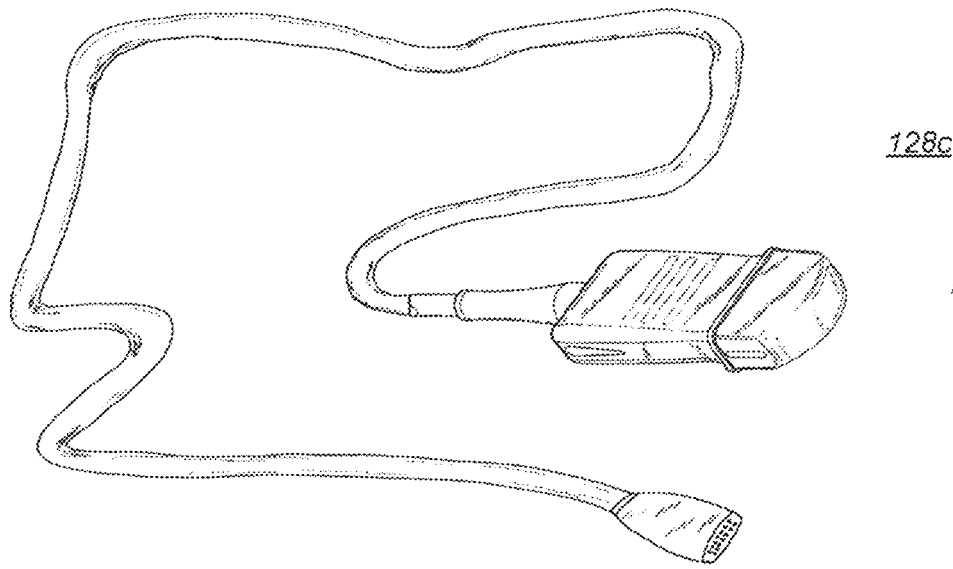

FIG. 2A is a known broadband linear array ultrasound transducer probe 128a for general abdominal imaging procedures. FIG. 2B is a known endocavity ultrasound transducer probe 128b for invasive medical imaging. FIG. 2C is a known handheld convex array ultrasound transducer probe 128c for pre-natal examinations, diagnosing cardiac health, and other medical procedures. For the sake of simplifying the present disclosure, the medical probes 128a-128c to be disinfected by the teachings in the present disclosure may be referred to herein as a probe 128. The probes 128 and other instruments to be disinfected by the teachings in the present disclosure may also be referred to herein as target articles 120. FIGS. 2A-2C may be collectively referred to herein as FIG. 2.

Medical devices, such as the probes 128 of FIG. 2, are manufactured in many different forms. The devices may be small diameter invasive tools such as catheters, endo-cavity probes, dental instruments, and the like. Other devices may be non-invasive, such as palm size and hand-held medical probes. Still other devices may be used in non-medical environments such as electronics, space-bound devices, fine instrumentation, pharmaceutical and other consumable manufacturing spaces, and the like. The manufactured structure of such devices may be simple or complex. The probes of FIG. 2 are illustrated because they demonstrate complex angles, symmetrical and non-symmetrical portions, a variety of materials, irregular sizes, and irregular shapes. The efficient disinfection by means of radiation such as UV of such devices has heretofore been difficult, and in some cases, not previously possible.

FIGS. 3A-3D are exemplary embodiments of disinfection tray systems arranged to align and temporarily hold a target article to be disinfected during a disinfection process. The exemplary disinfection tray system embodiments of FIGS. 3A-3D may be used in cooperation with one or more of the disinfection chamber 102 embodiments described herein. FIGS. 3A-3D may be collectively referred to herein as FIG. 3.

Figure 3A:
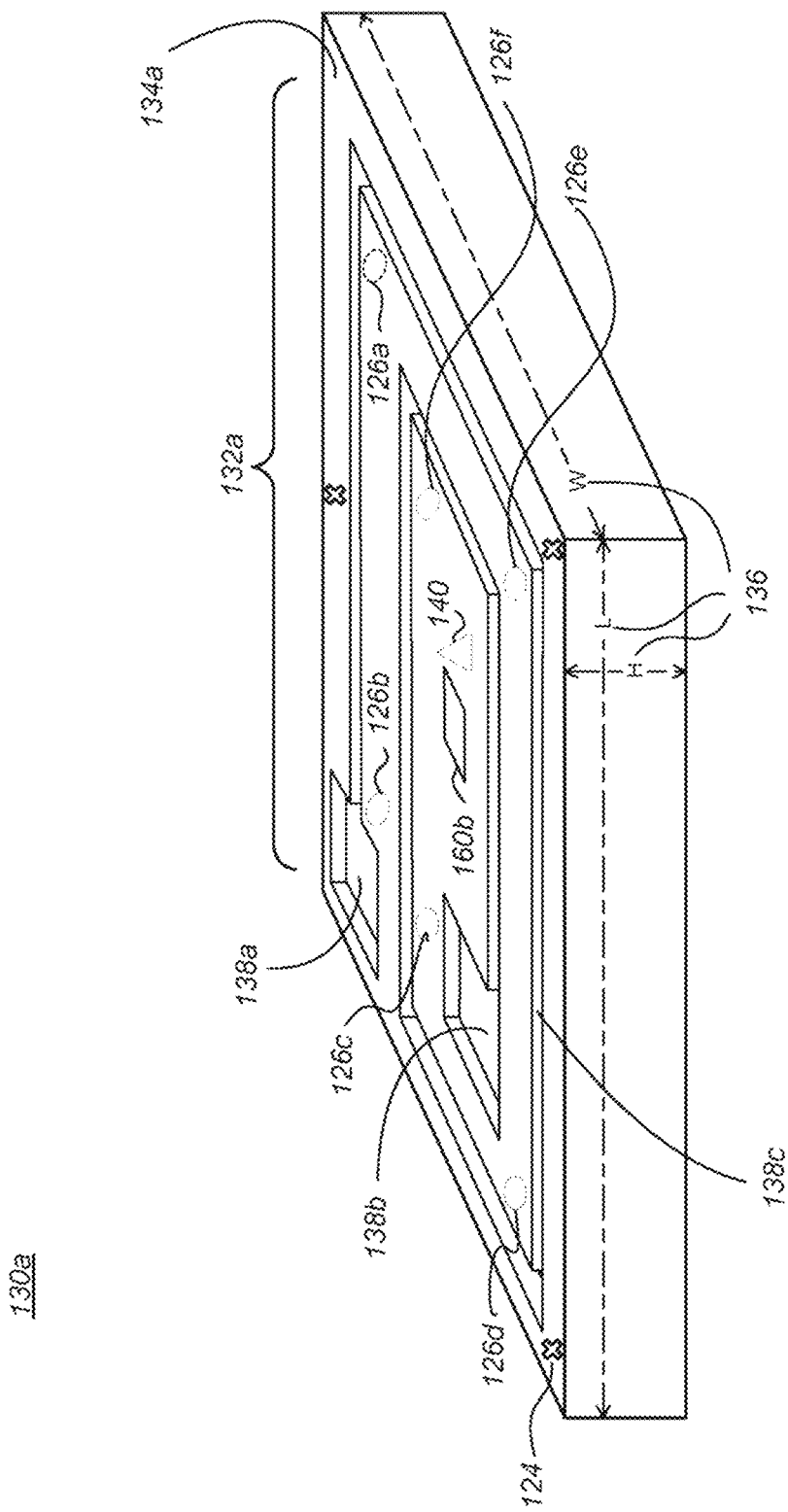
FIGS. 3A-3D are exemplary embodiments of disinfection tray systems arranged to align and temporarily hold a target article to be disinfected during a disinfection process.

FIG. 3A is an embodiment of a disinfection tray system 130a. The disinfection tray system 130a includes a tray portion 134a formed from a UV-transparent material, and an alignment portion 136. The tray portion 134a generally includes the surface of the disinfection tray system 130a, certain features that are formed on the surface of the disinfection tray system 130a, and certain features that extend into the surface of the disinfection tray system 130a. The tray portion 134a, for example, includes the receptacle 132a that is formed on the surface of the disinfection tray system 130a and extends, in this embodiment, down into the surface of the disinfection tray system 130a.

The alignment portion 136 of the disinfection tray system 130a includes a shape and one or more dimensions of the disinfection tray system 130a along with zero or more optional features that are used to align the disinfection tray system 130a in the interior volume of a disinfection chamber 102. In the embodiment of FIG. 3A, the alignment portion 136 includes the cuboid shape having a length L, a width W, and a height H. Other shapes, including complex shapes, are of course contemplated.

In the cuboid-shaped disinfection tray system 130a embodiment of FIG. 3A, tray portion 134a has the same length and width as the alignment portion 136. In addition, the tray portion 134a in FIG. 3A extends into the surface of the disinfection tray system 130a, and in at least some cases, the tray portion 134a may have the same height as the alignment portion. Accordingly, in some embodiments, the shape and dimensions of the tray portion 134a may define the shape and dimensions of the alignment portion 136. In this way, the shape and dimensions of the tray portion 134a, which define the shape and dimensions of the alignment portion 136, cooperate with features in the interior volume 114 of a disinfection chamber 102 to properly align a target article (e.g., target article 120 of FIG. 1, probe 128 of FIG. 2, or the like) to be disinfected with the radiation sources 104 of the disinfection chamber 102.

Optionally, the alignment portion 136 may also include an internal frame (not shown), and external frame (not shown), stiffening members (not shown), and any other such features to assist proper placement of the disinfection tray system 130a in the disinfection chamber. In some cases, these structural supports may also provide support to the UV-transparent material of the tray portion 134a.

In some cases, the alignment portion 136 may include specific structures that are dedicated to the alignment of the disinfection tray system 130a in the disinfection chamber. For example, three registration features 124 are represented in the embodiment of FIG. 3A, some of which, to avoid cluttering the figure, are not identified. These registration features 124 in the disinfection tray system 130a cooperate with corresponding registration features 124 in the disinfection system 100a of FIG. 1A. The shapes, sizes, location, and other such parameters of the registration features 124 in FIGS. 1A and 3A are non-limiting, and registration features having any other suitable shapes, sizes, locations, and the like are also contemplated. In various embodiments, registration features 124 may bumps and cooperating valleys, points and cooperating apertures, or any other suitable cooperating structures.

In some cases, registration features 124 include one or more radiation sensors 126 and one or more cooperating light sources 104. For example, in at least one embodiment, a first light source 104 in a disinfection chamber 102 is directed at a first radiation sensor 126a, which is sunken into the surface of the disinfection tray system 130a. In this way, part of the tray portion 134a forms a cylindrical wall around the surface of the first radiation sensor 126a, which substantially prevents indirect radiation from reaching the radiation sensor 126a. Conversely, if the surface of the radiation sensor 126a is in line-of-sight of the selected first light source 104, then radiation will reach the radiation sensor 126a, and the light source 104 and radiation sensor 126a can be paired as a registration feature to indicate that that disinfection tray system 130a is properly aligned within the disinfection chamber 102. In other cases, a discrete cylindrical body may be arranged about the radiation sensor 126a to form a wall that filters out indirect radiation. Such a wall, whether a discrete cylindrical body, a part of the tray portion 134a, or some other wall may be arranged at any suitable angle or other orientation to desirably align with a selected light source 104.

In some cases, registration features 124 include radio transmitters and cooperating receivers. In at least some of these cases, a small directed energy radio-frequency (RF) transmitter may be paired with a corresponding receiver. Antennas of each of the transmitter and receiver may be aligned (e.g., via a waveguide) to identify when the disinfection tray system 130a is suitably aligned in the disinfection chamber 102. Alternatively, or in addition, an RF signal may be encoded such that data from a time-of-flight sensor in the receiver can be used to identify when the disinfection tray system 130a is suitably aligned in the disinfection chamber 102. In still other cases, the cooperative registration features 124 of a disinfection tray system 130a and a disinfection chamber 102 may include any one or more of electromagnetic registration features, inductive registration features, and other types electronic and non-electronic registration features.

The tray portion 134a in the embodiment of FIG. 3A has a primary receptacle portion 138a arranged to receive a first portion of a target article to be disinfected, an alignment receptacle portion 138b, and a secondary receptacle portion 138c arranged to receive a second portion of the target article to be disinfected. Each receptacle portion 138a-138c has a defined shape and any number of defined dimensions. In some cases, each receptacle portion 138a-138c has a same shape and dimension; in other cases, one or more receptacle portions 138a-138c have different shapes, different dimensions, or different shapes and different dimensions. The tray portion 134a in FIG. 3A has a single primary receptacle portion 138a, a single alignment receptacle portion 138b, and a single secondary receptacle portion 138c, but in other cases, a tray portion may have any number of receptacle portions. For example, a different tray portion may have a first receptacle portion only; first, second, and third receptacle portions; first and second alignment receptacle portions, or any other numbers of primary receptacle portions, secondary receptacle portions, and alignment receptacle portions.

The tray portion 134a in FIG. 3A has a single, contiguous, uniform alignment receptacle portion 138b, but in other cases, a tray portion may have an alignment receptacle portion having any number of sub-portions. For example, in some cases, the alignment receptacle portion 138b includes two or more contiguous, uniform alignment receptacle portions 138b separated by a different receptacle portion. Such an implementation may, for example, be useful for a probe having a connector at a first proximal end location of a cable, a control mechanism at an interim second location of the cable, and a sensor or other point of patient contact at a third distal end of the cable.

In some embodiments, the alignment receptacle portion may terminate at a natural boundary of the tray portion 134a. In this way, for example, a receptacle is arranged to receive a portion of the target article to be disinfected, a flexible portion (e.g., a cable, a hose, or the like) of the target article to be disinfected is placed in the alignment receptacle portion, and a portion of the target article that will not be disinfected extends beyond the boundaries of the tray portion.

The disinfection tray system 130a embodiment is arranged to snugly contain a target article to be disinfected. The target article may be, for example, a target article 120 (FIG. 1), a medical probe along the lines of the probes 128 of FIG. 2, or some other target article to be disinfected. In the embodiment, a first sensor portion of the target article to be disinfected is placed in the first receptacle 136a, and a "cable" portion of the target article is placed in the alignment portion 136b. A third connector portion of the target article is placed in the second receptacle 136c, and then the disinfection tray system 130a is placed in a chamber along the lines of the disinfection chambers 102 of FIG. 1. Because of the UV-transparency of the tray portion 134, each portion of the target article that is intended to be disinfected during a disinfection procedure will be disinfected.

The disinfection tray system 130a may optionally include one or more structures formed of a radiation sensitive medium 140. The radiation sensitive medium may, for example, include a dye, a liquid, a paint, a film, a glass, a ceramic, or some other medium that reacts when exposed to a particular form of radiation such as ultraviolet radiation. In at least some embodiments, the radiation sensitive medium 140 is a photochromic substance (e.g., a photosensitive paper, a color-changing ultraviolet detection beads, and the like) that changes color when exposed to radiation from a radiation source 104, and the change in color can represent how much radiation the target article has been exposed to. In these or in other cases, the exposure to radiation from a radiation source 104 induces a measurable change in electrical conductivity of the radiation sensitive medium 140, and in these cases, the electrical conductivity change can be used to determine how much radiation has been delivered to the target article. In at least some cases, a radiation-sensitive material may include silver halide. In other cases, the radiation-sensitive material may comprise a silica, an alumina, and a metallic fluoride such as cadmium fluoride, lead fluoride, or some other fluoride. Other radiation sensitive elements and compounds are also contemplated.

An optional controller 160b is arranged in the disinfection tray system 130a of FIG. 3A. A controller 160b, which is along the lines of the controller 160a in the disinfection system 100 of FIG. 1, may be arranged in any disinfection tray system of the present disclosure. As described herein, the controller 160b may be arranged to include any one or more of a processor, memory, at least one transceiver, a user interface, and any number of peripheral devices (e.g., clocks, control circuits, power circuits, and the like). The controller 160b may be arranged to maintain a time value that indicates when the disinfection tray system 130a was last exposed to disinfecting radiation (e.g., time information identifying the execution of one or more previous disinfection cycles). The controller 160b may be arranged to indicate that target article is properly positioned in the receptacle 132a. The controller 160b may also control the receipt and transmission of information such as serial numbers, identification information, type or types of target article that can be disinfected in the disinfection tray 130a, alignment of the disinfection tray 130a in the disinfection chamber 102, and any other such information.

Figure 3B:
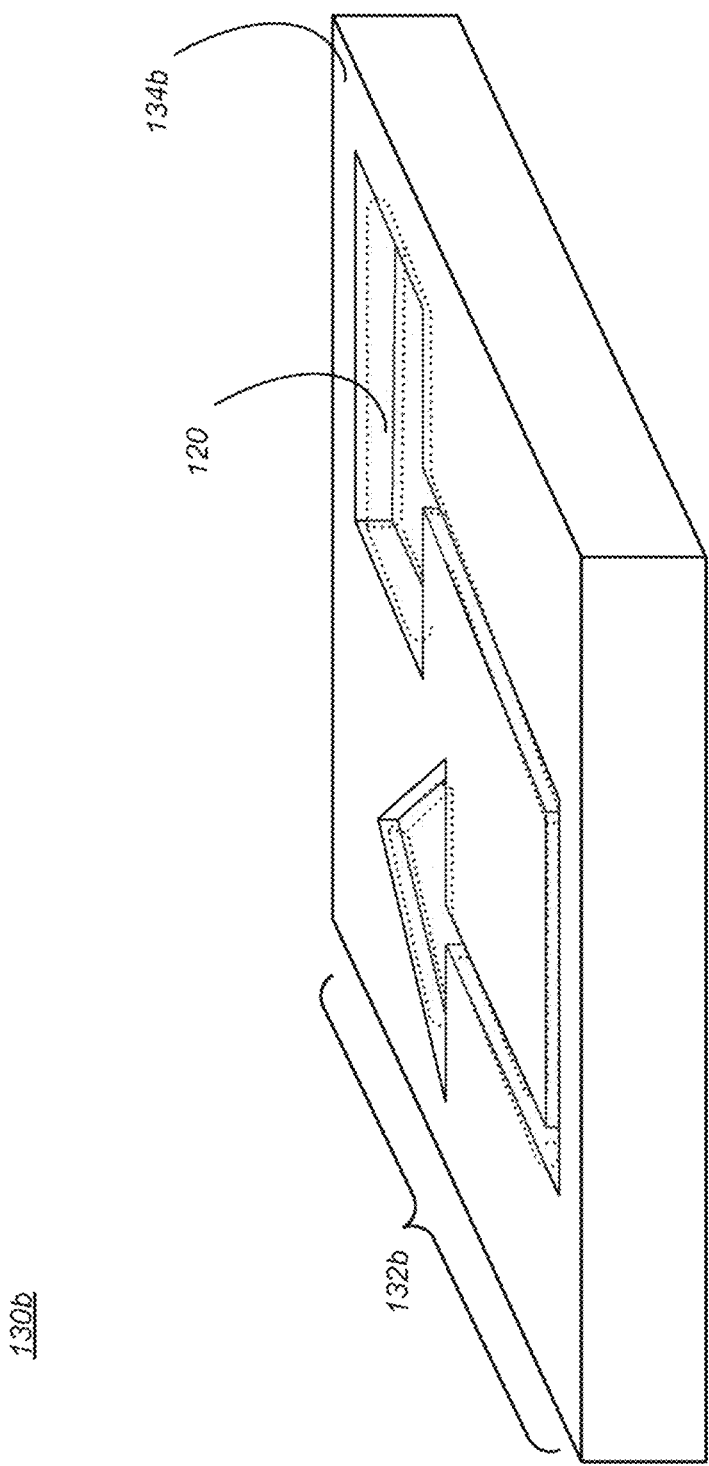

FIG. 3B is another embodiment of a disinfection tray system 130b. The disinfection tray system 130b includes a tray portion 134b formed from a UV-transparent material and a receptacle 132b. A target article 120 is aligned in the receptacle 132b. Other structures and features of the disinfection tray system 130b are not identified so as to avoid cluttering the figure. As evident in FIG. 3B, the receptacle 132b is arranged for a specific target article 120, and more particularly, for a specific orientation and placement of the target article 120 into the receptacle 132b. The target article 120 could not intuitively or instructionally be arranged in the receptacle 132b in any other suitable way. When so arranged, and when the disinfection tray system 130b is placed in a disinfection chamber 102, the radiation from radiation sources 104 (FIG. 1) will penetrate the disinfection tray 134b and expose all surfaces of the target article 120 with disinfecting radiation. In at least some cases, a controller 160b is arranged to receive and analyze sensor data from one or more radiation sensors 126, and based on the analysis, the controller 160b is arranged to control, direct, or otherwise influence the operations of the radiation sources 104 in the disinfection chamber 102.

Figure 3C:
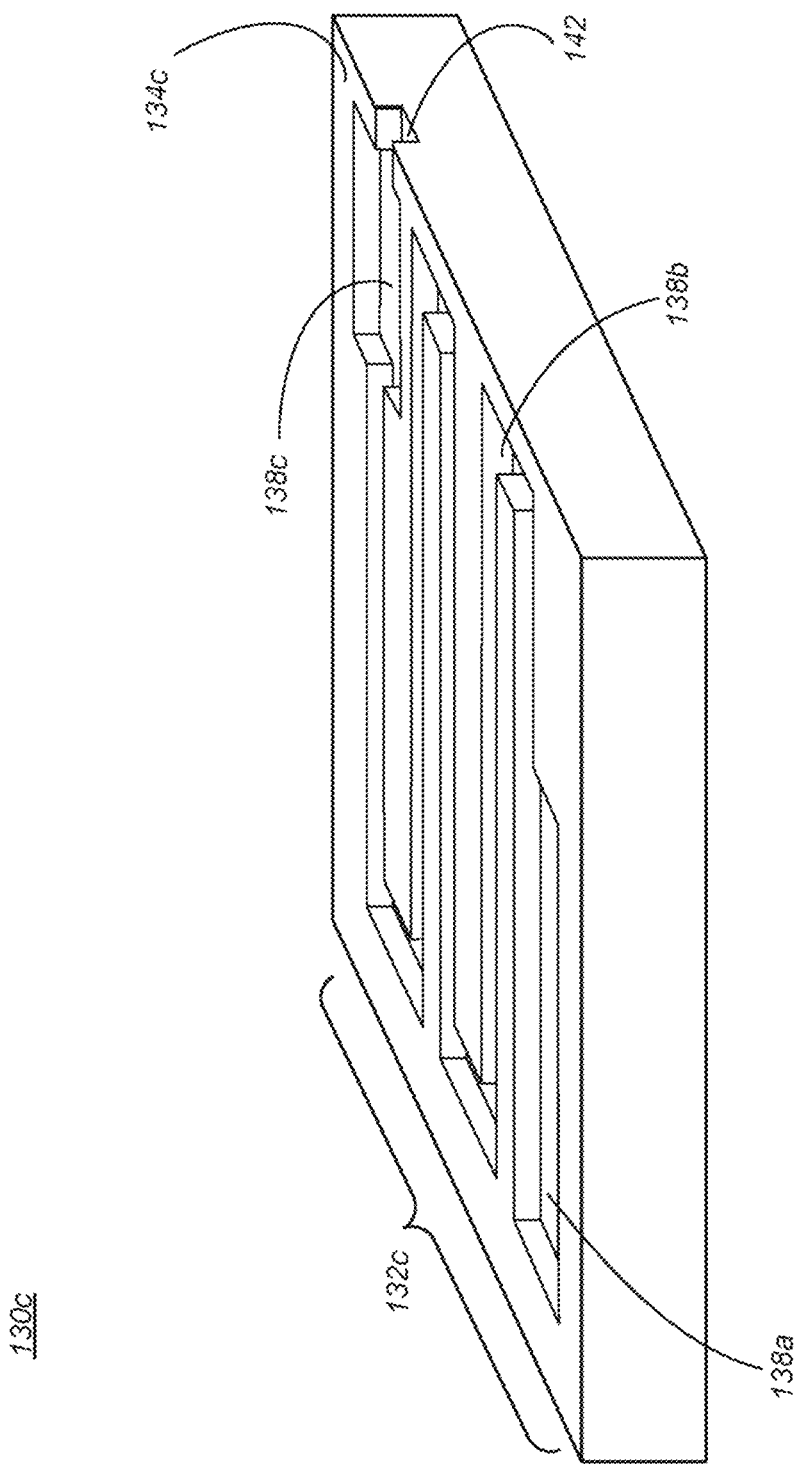

FIG. 3C is yet one more embodiment of a disinfection tray system 130c. The disinfection tray system 130c includes a tray portion 134c formed from a UV-transparent material and a receptacle 132c. The disinfection tray system 130c embodiment of FIG. 3C also includes an alignment receptacle pass-through portion 142, which is formed at a natural boundary of the tray portion 134c.

When a target article to be disinfected is arranged in the disinfection tray system 130c, a first portion of the target article may be placed in a primary receptacle portion 138a. The first portion of the target article may, for example, be an ultrasound sensor probe that makes contact with the body of a patient. A second portion of the target article, which may be a cable, for example, will be arranged in the alignment receptacle portion 138b, which snakes across the surface of the tray portion 134c. A hand-held controller portion of the target article to be disinfected may be arranged in the second receptacle portion 138c, and a cable that begins at the hand-held controller portion of the target article will continue across the boundary threshold of the tray portion 134c at the alignment receptacle pass-through portion 142. The cable of the target article that extends out from the disinfection tray system 130c is typically a portion of the target article that will be plugged into the particular apparatus (e.g., the ultrasound machine). This cable portion may be placed in the disinfection chamber 102, but disinfection of this cable portion may not be a primary function of the disinfection system 100.

Figure 3D:
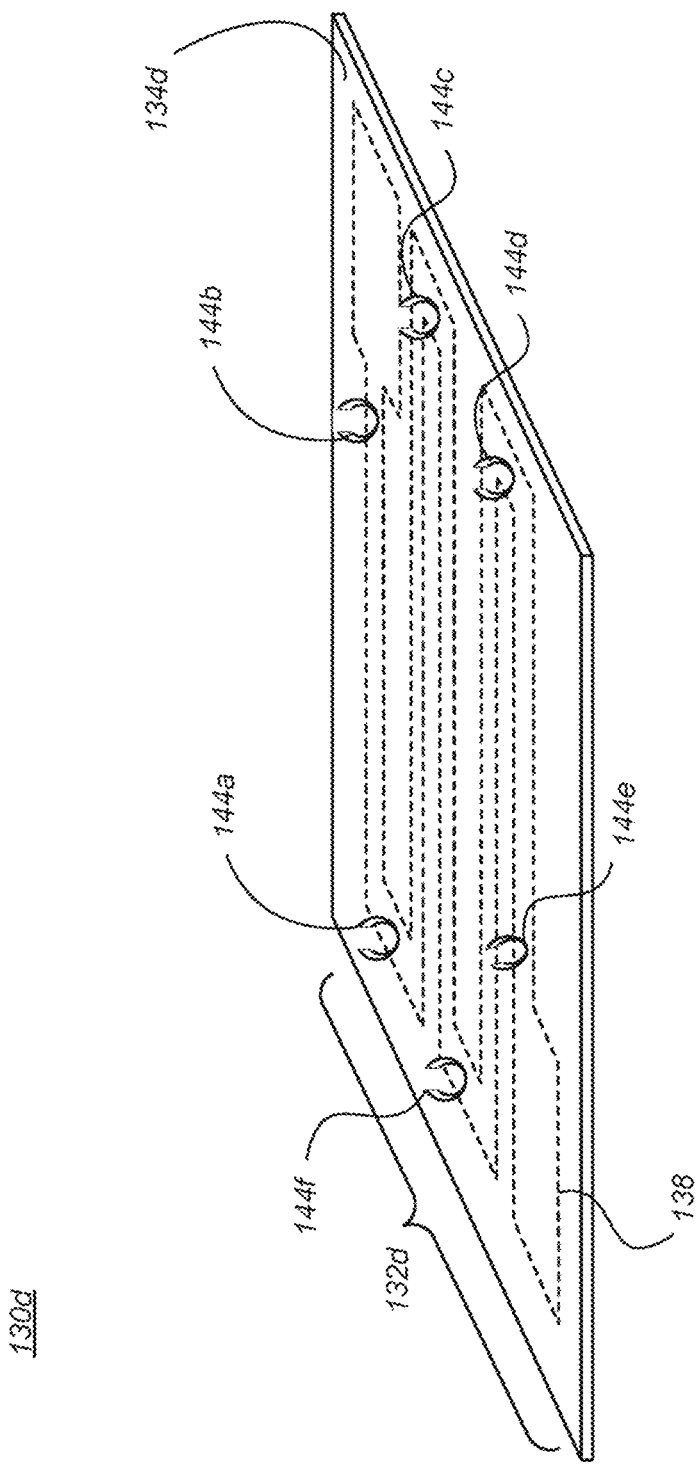

FIG. 3D is an embodiment of a disinfection tray system 130d that has a receptacle 138 with very little depth (e.g, about 50 millimeters (mm), about 30 mm, about 10 mm, or less) or in some cases, no depth at all. The tray portion 134d of the disinfection tray system 130d is formed from a UV-transparent material. An optional template pattern of the target article to be disinfected may be integrated with, or otherwise represented on, the surface of the tray portion 134d. One or more containment structures 144a-144f are arranged to temporarily align and affix the target article to be disinfected to the tray portion 134d.

In at least some cases, the template pattern of the receptacle 138 may be formed from a radiation-sensitive material. In this way, the template may be used both to guide a user to properly place the target article to be disinfected and as an indicator that a disinfection cycle has executed. In other cases, the template pattern may be printed on the tray portion 134d, adhered to the tray portion 134d, or integrated in some other way. The template pattern may include printed text instructions to a user guiding proper alignment and placement of the target article to be disinfected.

The disinfection tray system 130d may contain any suitable number of containment structures 144a-144f. The containment structures may be formed as clips, clamps, clasps, brackets, or some other type of fastening means. The containment structures 144a-144f may be formed entirely or partially from a UV-transparent material. In some cases, one or more of the containment structures 144a-144f may be moved, removed, repositioned, reoriented, or otherwise located at a point and orientation desired by a user.

In some cases, two or more template patterns may be formed on the same tray portion 134d. In at least some of these cases, the tray portion 134d may have containment structures 144a-144f for each of the two or more templates. In others of these cases, one or more containment structures 144a-144f may be placed by a user at particular locations and orientations suitable for the respective target article that corresponds to the particular template. Accordingly, some embodiments of disinfection tray system 130d may have include fixed containment structures, and these or other embodiments may include removable or otherwise re-positionable containment structures.

FIGS. 4A-4E are disinfection tray system embodiments 130e-130i, which demonstrate the flexibility of the present disinfection technology. Disinfection tray system embodiments 130e-130i may be completely or partially formed from UV-transparent material. The disinfection tray system embodiments 130e-130i include one or more receptacles 132e-132i, respectively, formed in a corresponding tray portion 134e-134i. The receptacles 132e-132i are along the lines of other receptacles described in more detail in the present disclosure. The receptacles 132e-132i are simplified to more clearly illustrate other features of the disinfection tray system embodiments 130e-130i.

Each of the disinfection tray system embodiments 130e-130i has a different alignment portion 136. The alignment portion 136 comprises the shape and one or more dimensions of the respective disinfection tray system 130e-130i. The alignment portion 136 of disinfection tray system embodiments 130e-130h of FIGS. 4A-4D include a cuboid shape, a length L, a width W, and a height H. The alignment portion 136 of the disinfection tray system embodiment 130i of FIG. 4E includes a disc shape, a diameter D, and a height H. Other simple shapes and complex shapes are contemplated.

Figure 4A:
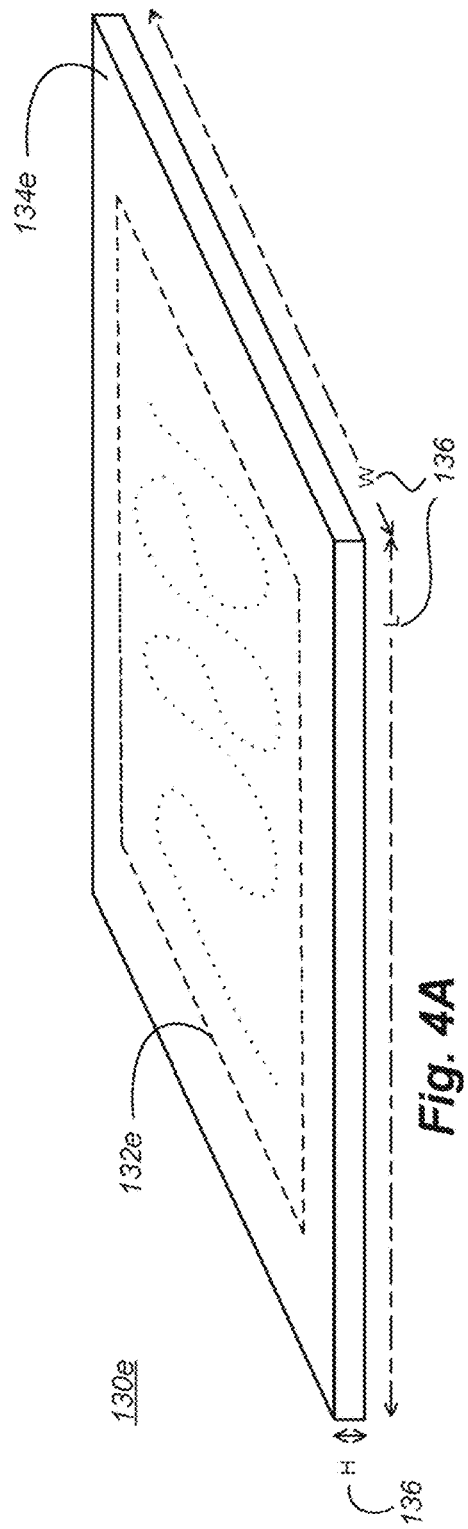
FIGS. 4A-4E are additional disinfection tray system embodiments.
Figure 4B:
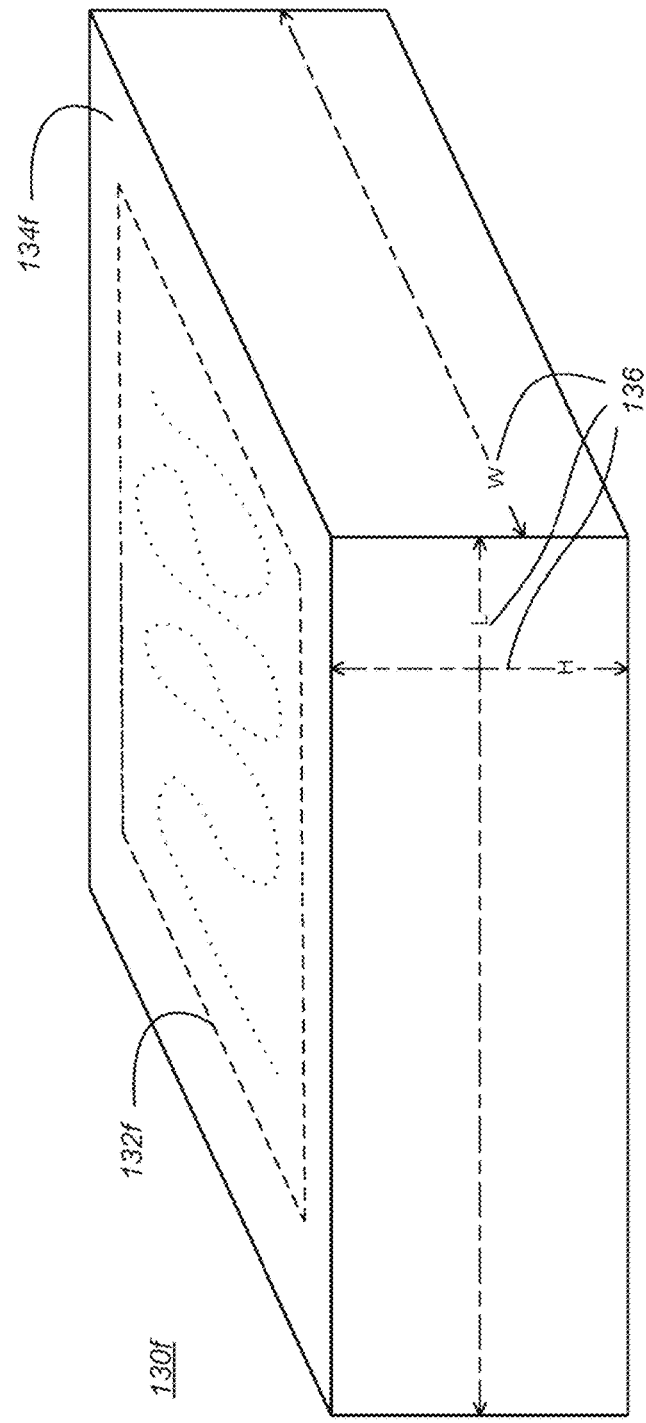

The disinfection tray system embodiment 130e of FIG. 4A may have a height of two or three centimeters (2 cm or 3 cm) or less. The disinfection tray system embodiment 130f of FIG. 4B may have a height of three centimeters (3 cm) or more. The disinfection tray system embodiments 130e, 130f have a same length L and a same width W. The length and width of various ones of the disinfection tray system embodiments taught in the present disclosure may be desirably chosen for use in a selected disinfection system 100.

Figure 4C:
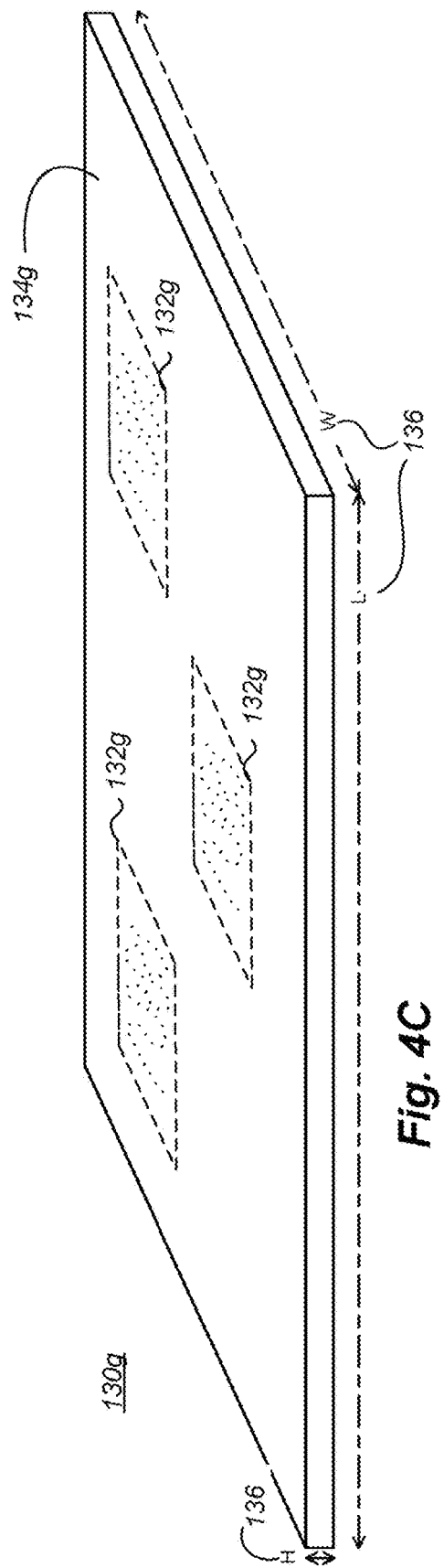

In FIG. 4C, a disinfection tray system embodiment 130g includes a plurality of receptacles 132g arranged to contain a particular target article to be disinfected. Each receptacle 132g formed in the surface of the tray portion 134g may be like all of the other receptacles 132g in some cases. In other cases, only some receptacles 132g are like other receptacles 132g. In still other cases, none of the plurality of receptacles 132g are like any other receptacle 132g. Using the disinfection tray system embodiment 130g of FIG. 4C, two or more target articles may be simultaneously disinfected.

Figure 4E:
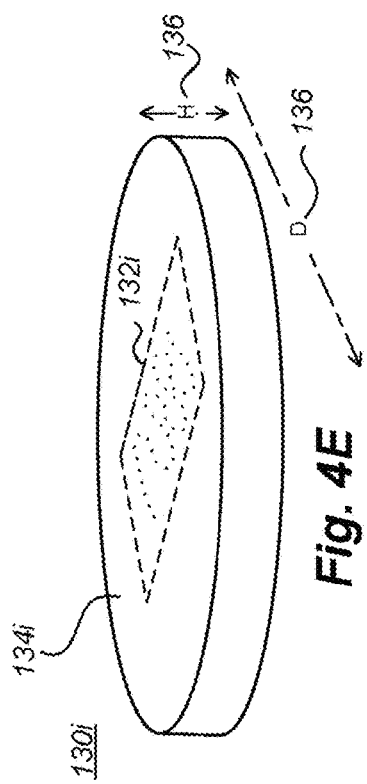
Figure 4D:
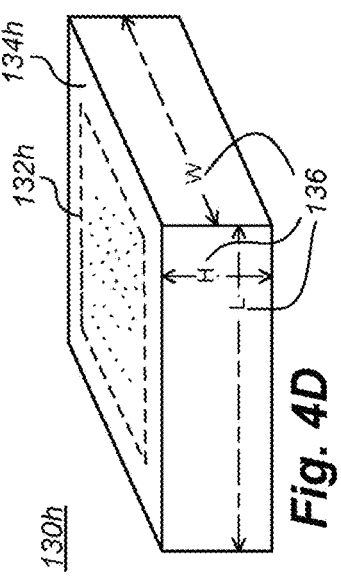

The disinfection tray system embodiment 130h of FIG. 4D is relatively smaller than other disinfection tray system embodiments of the present disclosure. In at least some cases, a plurality of the disinfection tray system embodiments 130h may be concurrently placed in a certain disinfection chamber 102, and two or more target articles may be simultaneously disinfected.

In FIG. 4E, a disc-shaped disinfection tray system embodiment 130i is presented. The disc-shaped disinfection tray system embodiment 130i may be arranged to more easily align a particular target article to be disinfected. Additionally, or in the alternative, the disc-shaped embodiment may provide for easier alignment in a particular disinfection system 100. The disc-shaped disinfection tray system embodiment 130*i*, and a disinfection tray system embodiment having any other particular shape may be selected for other reasons.

Figure 5A:
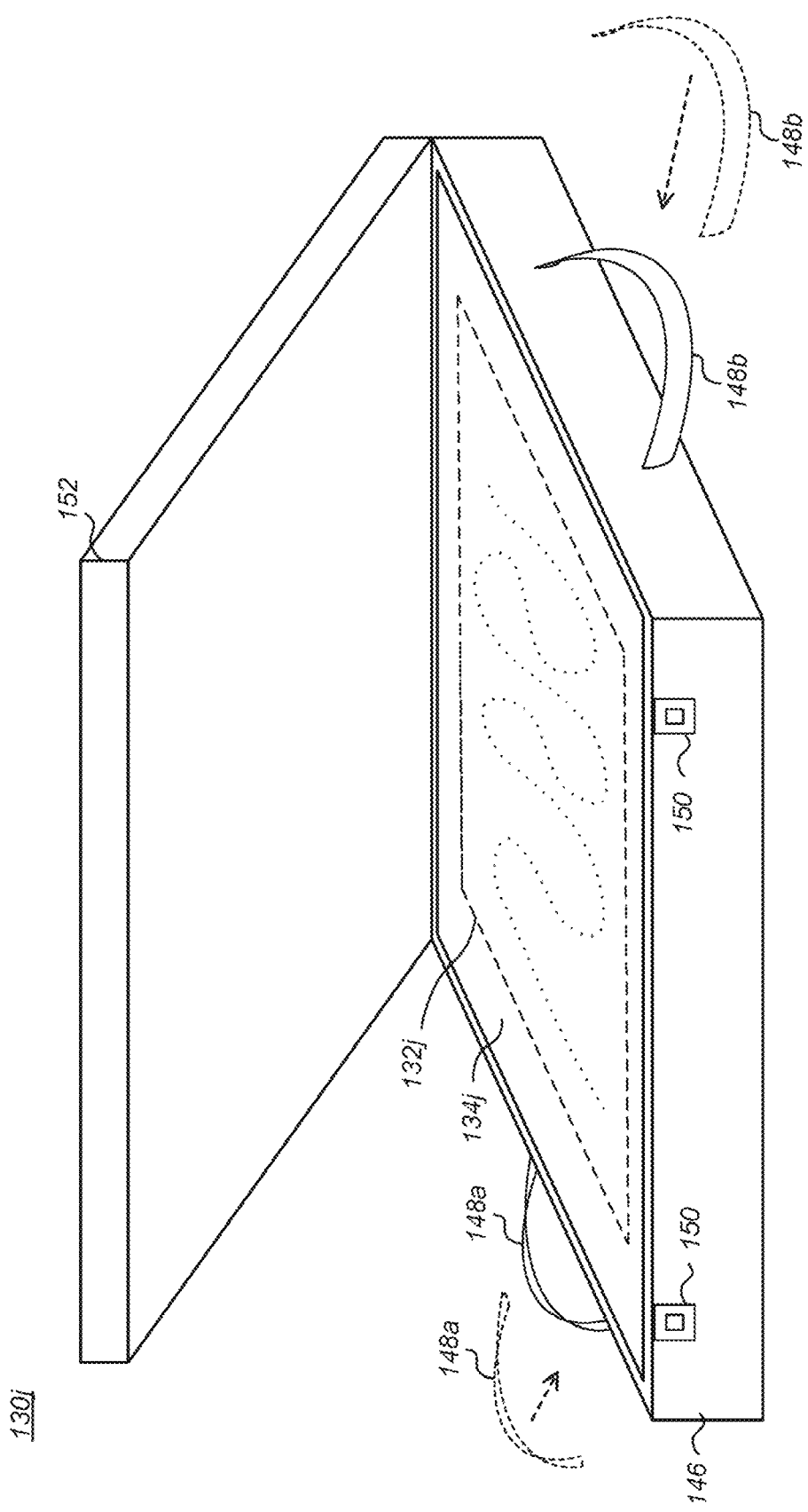

FIGS. 5A and 5B are optional container portions 146 that may be arranged as part of a disinfection tray system 130*a*-130*j*. FIGS. 5A-5B may be collectively referred to herein as FIG. 5.

FIG. 5A is a disinfection tray system 130*j* that includes a container portion 146 arranged to hold at least one tray portion 134*j*. In the embodiment of FIG. 5A, the container portion 146 is a mechanically sealable case 146. The mechanically sealable case may be arranged to store the any number of target articles before disinfection, during disinfection, and after disinfection. In some cases, the container portion 146 is arranged to store one or more target articles for a long time after a disinfection process. In this way, for example, a target article may be disinfected at a first time and then stored until a second time proximate to when the target article is put to use. Any number of minutes, hours, days, month, or even several years may pass between the first time and the second time.

The container portion 146 may in some cases be formed partially or fully from UV-transparent material. The container portion 146 may be a solid structure that fully contains a tray portion 134*j*. Alternatively, the container portion 146 may be a mesh or netting, a frame, or some other arrangement. The container portion 146 may in some cases have a shape and one or more dimensions that define the alignment portion of the disinfection tray system 130*j*, along the lines of the alignment portion 136 of FIG. 3 and FIG. 4.

The mechanically sealable case of FIG. 5A may optionally include one or more handles 148*a*, 148*b*, a locking mechanism 150, a lid portion 152, and other optional features. The optional handles 148*a*, 148*b* may be arranged on opposing sides of a container portion 146 as illustrated in FIG. 5A. In other embodiments, one of skill in the art will recognized that one or more handles may be arranged on all sides of the container portion 146, on the top of the container portion 146, on the bottom of the container portion 146, or in any other locations. Each handle 148*a*, 148*b* may have two points of contact with the container portion 146 as illustrated in FIG. 5A. Alternatively, handles 148*a*, 148*b* may take other suitable forms. The handles may be loops, buttons, prongs, knobs, shafts, grips, or some other structure. The handles may be rigid or flexible. The handles may be temporary or fixed. In some cases, such as when handles 148*a*, 148*b* are first installed and used to transport a disinfection tray system 130*j* and then later removed, the handles may have features (e.g., pegs, pins, hooks, apertures, protrusions, or any other suitable structures) that cooperate with corresponding features of the container portion 146 to facilitate placement and use of the handles.

The optional locking mechanism 150 of FIG. 5A may be used to secure an optional lid portion 152 to the body of the container portion 146. The locking mechanism 150, when included, may be any suitable means to temporarily secure the optional lid 152. Suitable locking mechanisms 150 include clasps, mortise locks, springs, hydraulic pistons, single use locking means (e.g., stickers, cable ties, tags, and the like). In some cases, the locking mechanism may include electronic locking systems such as radio-frequency identifier (RFID) based locking systems, relay-based locking systems, audible alarm-based locking systems, and other such systems.

The optional lid portion 152 of the disinfection tray system 130*j* may be any suitable lid. The lid may form a seal around a perimeter of the container portion 146 or the tray portion 134*j*. In such embodiments, target articles may be prevented from spreading contaminants. Additionally or alternatively, sealable lids 152 may prevent disinfected target articles from becoming contaminated. In at least some embodiments, a lid 152 is sealed, but not hermetically sealed. In other embodiments, a lid 152 is hermetically sealed. The lid 152, like other optional features of the disinfection tray system 130*j* (e.g., locking mechanisms 150, handles 148*a*, 148*b*), may in some cases be formed from UV-transparent material.

FIG. 5B is a container portion of a disinfection tray system 130. The container portion 146 in the embodiment of FIG. 5B is arranged to hold any number of different type of tray portions 134*a*-134*j*. When so combined, the composition of a tray portion 134*a* and a container portion 146 forms the disinfection tray system 130*a*; when so combined, the composition of a tray portion 134*b* and a container portion 146 forms the disinfection tray system 130*b*; and so on. It is recognized that in such a system, the shape and at least one dimension of the container portion 146 provide at least part of the alignment portion 136 that cooperates with a disinfection system 100. In at least one example, a particular disinfection tray system 130 is arranged to hold a particular target article. When the particular disinfection tray system 130 is placed in the container portion 146 and the combination is placed in a certain disinfection chamber 102, the target article to be disinfected will be desirably aligned in view of the radiation sources 104 arranged in the certain disinfection chamber 102. Such a configuration will permit users of the systems to more efficiently and more reliably disinfect target articles with increased assurance that adequate disinfection has occurred.

For the avoidance of doubt, the container 146 of FIG. 5B may be suitably arranged with optional features. The optional features include handles 148*a*, 148*b*, a locking mechanism 150, a lid 152, and any other such features.

FIGS. 6A-6E are disinfection system 100*c*-100*g* embodiments arranged to receive any one or more of the disinfection tray embodiments 130*a*-130*j* taught in the present disclosure. FIGS. 6A-6E may be collectively referred to herein as FIG. 6. The disinfection tray systems 130*a*-130*j* taught in the present disclosure may be collectively referred to herein as a disinfection tray system 130. Many features of the disinfection systems 100*c*-100*g* are not illustrated or identified in FIG. 6 to avoid unnecessarily obscuring other features of interest in the embodiment.

Figure 6A:
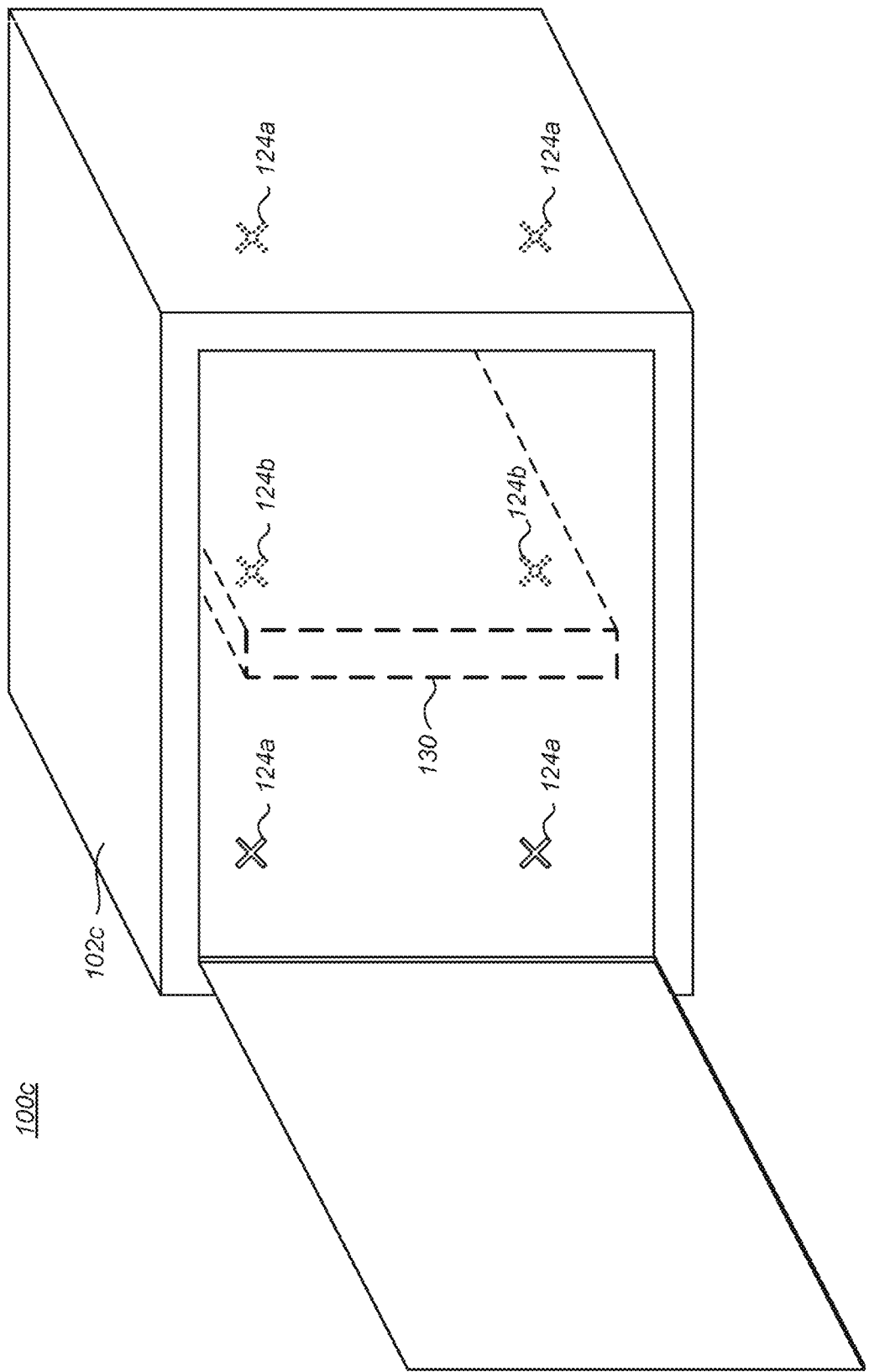

In FIG. 6A, a disinfection system 100*c* includes a disinfection chamber 102*c* arranged to receive a disinfection tray system 130. The disinfection tray system 130 is arranged to be placed in a particular alignment (e.g., a length-wise vertical alignment). One or more registration features 124*a* of the disinfection chamber 102*c* cooperate with one or more corresponding registration features 124*b* of the disinfection tray portion 130. The registration features 124*a*, 124*b* are arranged to permit a user to determine that the disinfection tray portion 130 is correctly placed in the disinfection chamber 102*c* quickly, efficiently, and with confidence. The registration features 124*a*, 124*b* may be any type of registration features. The chamber-based registration features may, for example, have a first size and shape, and the tray-based registration features may have a second size and shape that cooperates with the first size and shape. These features may include grooves, rails, posts, apertures, protuberances, and any other such physical features. These features may provide tactile feedback, visual feedback, audible feedback, or some other type of positive feedback that indicates to a user that the disinfection tray 130 is properly aligned in the disinfection chamber 102c. In these or other cases, the registration features may include electronic circuits such as, but not limited to, photo-diodes, light emitting diodes (LED's), time of flight sensors, radio signals, inductive circuits, and the like.

Figure 6B:
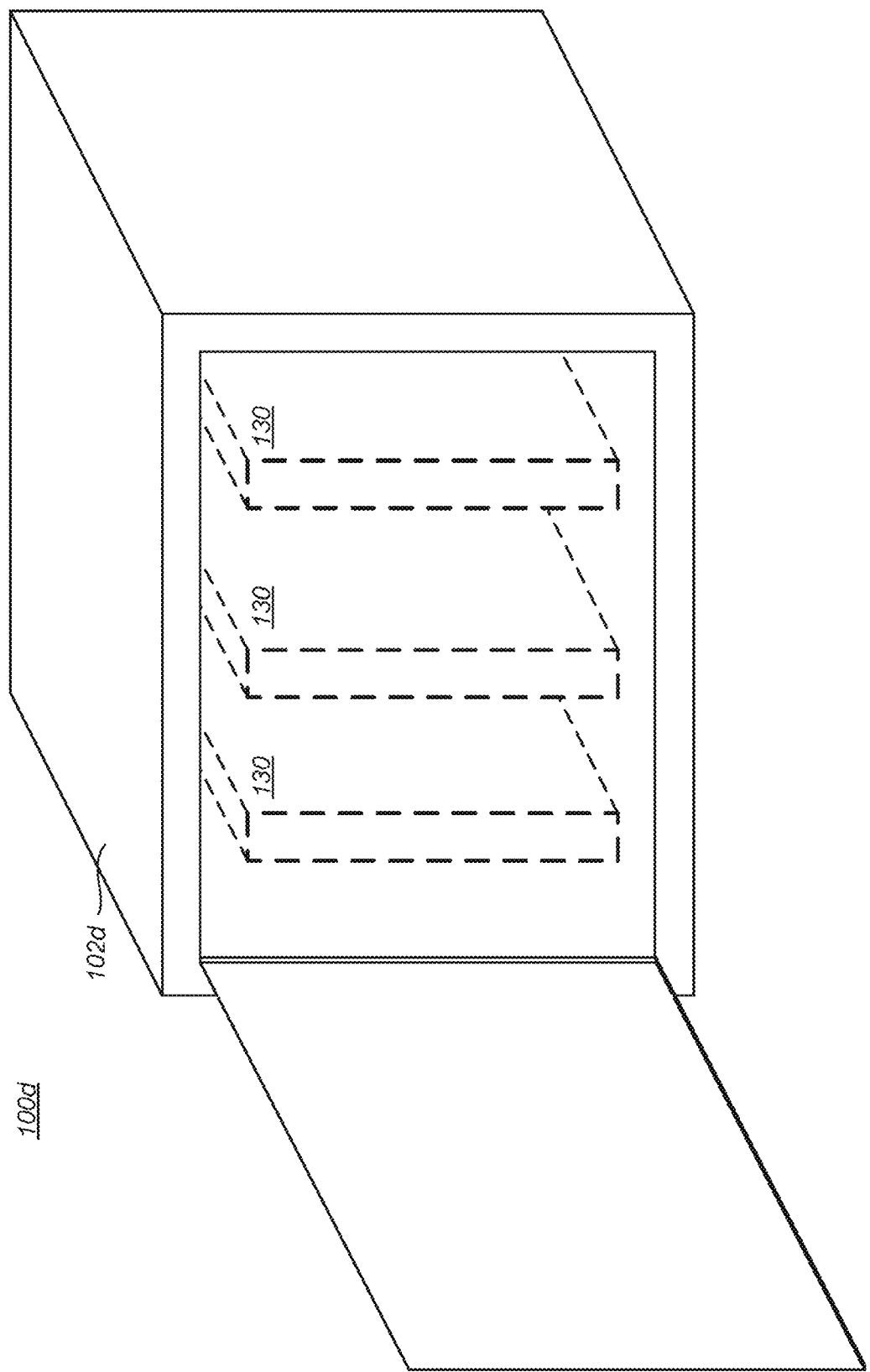

In the embodiment of FIG. 6B, a disinfection system 100d includes a disinfection chamber 102d arranged to optionally receive a plurality of disinfection tray systems 130. Three disinfection systems 130 are shown in FIG. 6B, each of which is length-wise vertically aligned. A different number of disinfection tray systems 130 in different alignments and orientations are contemplated.

Figure 6D:
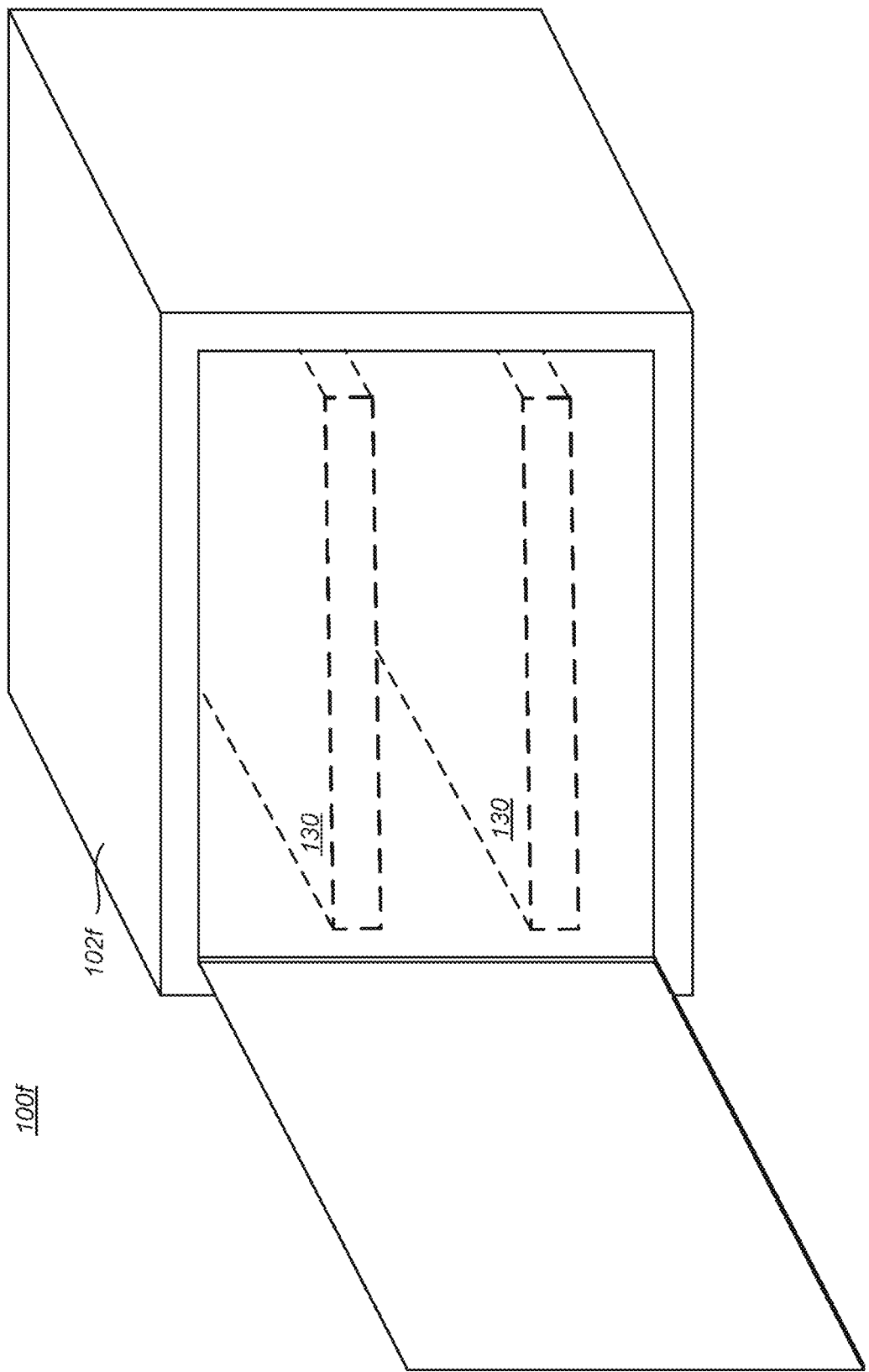

FIGS. 6C and 6D are disinfection systems 100e, 100f, respectively, that includes horizontally aligned disinfection tray systems 130. A single disinfection tray system 130 is arranged in a disinfection chamber 102e in FIG. 6C, and two disinfection tray systems 130 are arranged in a disinfection chamber 102f in FIG. 6D. Any other number of disinfection tray systems 130 in different alignments and orientations are contemplated.

Figure 6E:
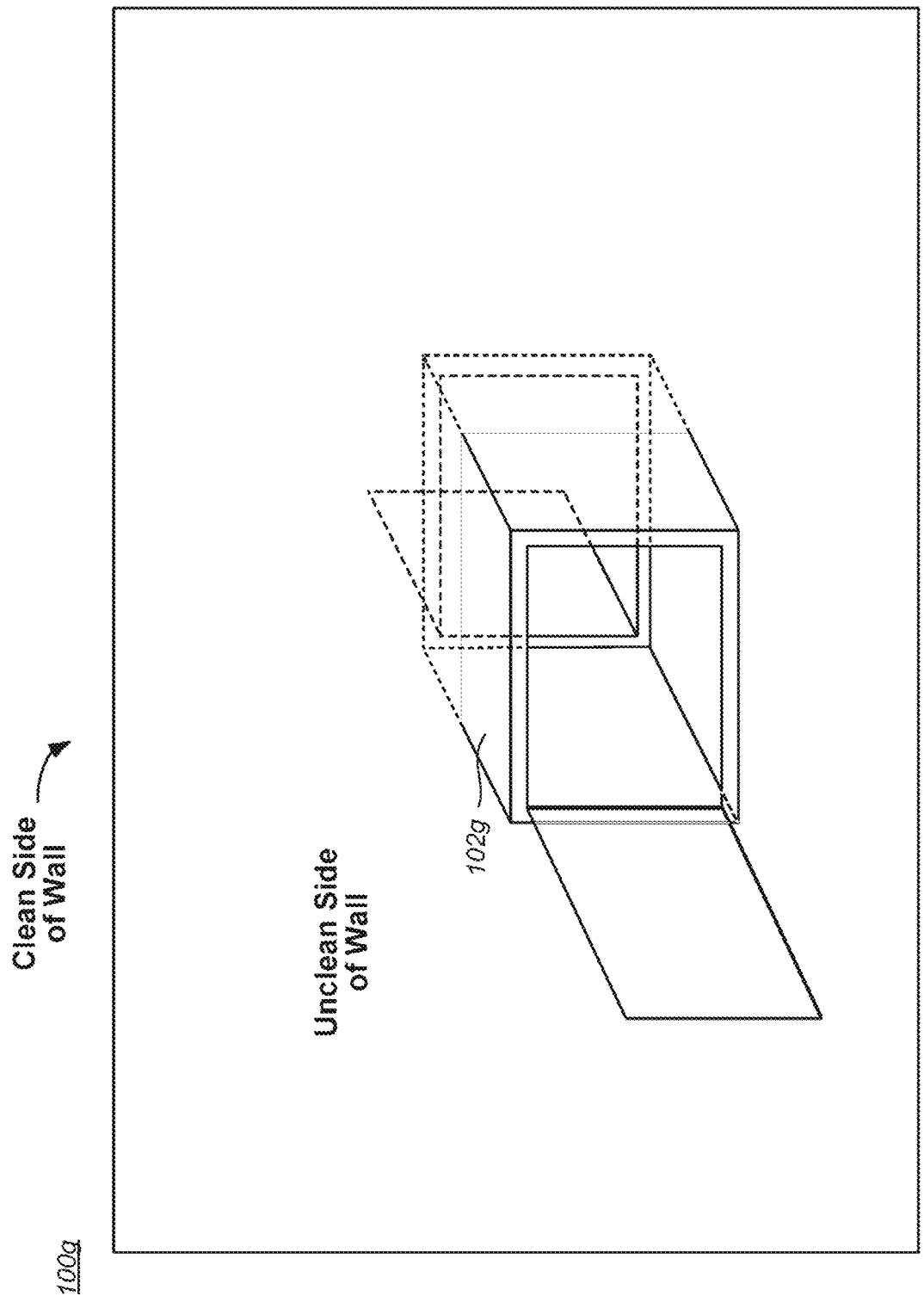

In the disinfection system 100g of FIG. 6E, a disinfection chamber 102g is mounted in a wall. The disinfection chamber 102g has a first opening on an unclean side of the wall, and a second opening on a clean side of the wall. Respective doors permit access to the interior volume of the disinfection chamber 102g from either side of the wall. In at least one embodiment, contaminated target articles are aligned in a disinfection tray system from the unclean side of the wall. Both doors of the disinfection chamber 102g are closed, and a disinfection cycle is executed. The disinfected target articles are then removed from the disinfection chamber 102g by opening the door on the clean side of the wall.

In at least some cases of the disinfection system 100g, the doors of the disinfection chamber 102g are intelligently controlled. For example, after a disinfection cycle is executed, the door on the unclean side may be locked and not permitted to open until the door on the clean side of the wall is opened. Circuits associated with one or more controllers of the disinfection system 100g may be used to determine whether or not a disinfection tray system 130 is present in the disinfection chamber 102g, and if the tray is present and if a disinfection cycle is executed, then circuitry may determine when the disinfected target articles are removed from the disinfection chamber 102g. Along these lines, the circuitry may further prevent both doors of the disinfection chamber 102g from being open concurrently. If, for example, the door on the unclean side of the wall is open, then the door on the clean side of the wall may be locked and prevented from opening. Other such controls are of course contemplated.

FIG. 7 is an exemplary controller 160. The controller 160a of a disinfection system 100b (FIG. 1C) is formed and arranged along the lines of the controller 160 of FIG. 7. The controller 160b of a disinfection tray system 130a (FIG. 3A) is formed and arranged along the lines of the controller 160 of FIG. 7. Embodiments of controller 160 include a processor 162 and a memory 164. The memory 164 includes software instructions 166 that are executable by the processor to carry out the acts of the controller's particular system.

In the embodiment of FIG. 7, a controller 160 of a disinfection system 100 will include chamber software executable instructions 166a, and a controller 160 of a disinfection tray system 130 will include tray software executable instructions 166b. In some cases, executable software 166 will include instructions for both a disinfection system 100 and a disinfection tray system 130; and in other cases, executable software 166 will include instructions for only one of a disinfection system 100 and a disinfection tray system 130. The dashed lines around the chamber software 166a of executable software 166 and the dashed lines around the tray software 166b of the executable software 166 signify a controller 160 may include one or both of the chamber software 166a and the tray software 166b.

The memory 164 of a controller 160 will include any number of suitable memory locations to store parameters 168. The parameters 168 may include temporary storage variables, transient values, and other permanent and transitory information generated, stored, consumed, or otherwise associated with the executable software 166, the processor 162, and any other logic of the controller 160 or associated therewith.

The controller 160 may optionally include a user interface 170, a sensor interface 172, and a communications interface 174. The controller 160 also comprises other desirable circuitry. A non-limiting, non-exhaustive list of at least some of the other desirable circuitry includes power circuitry, clock circuitry, a memory interface, bus structures to electrically and communicatively couple various hardware circuits, and the like. The other desirable circuitry is not shown in FIG. 7 to avoid unnecessarily complicating the embodiment.

The user interface 170 may include any suitable number of human interface devices (HID). In some cases, the controller 160 will not have any HID devices. The user interface 170 may include audio, visual, tactile, and other such circuits. A non-limiting list of HID means includes display screens, keyboards, computer mice, touch screen circuits, speakers, piezo-electric devices, vibrators, LED's, and other such circuits.

In some cases, the user interface 170 may include at least one clean/not clean indicator such as a green "clean" LED and a red "not clean" LED. The user interface 170 may include a time-of-last-clean indicator, which may display or otherwise communicate time, date, or time and date information reporting when a particular target article 120 was disinfected, and the user interface may also include a disinfection expiration indicator. A disinfection expiration indicator may be used to indicate when a target article 120 should be re-disinfected.

In some cases, the user interface 170 may include any desirable number of "aligned" and "not-aligned" indicators. The aligned and not-aligned indicators (i.e., alignment indicators) may represent an alignment condition of any portion of a target article 120 within a receptacle portion 138 of a disinfection tray system 130. These or other aligned and not-aligned indicators may additionally or alternatively represent an alignment condition of a disinfection tray system 130 within a disinfection chamber 102. The alignment indicators may be visual alignment indicators, such as a template, outline, or image of a target article to be disinfected; the visual alignment indicator formed or otherwise placed in a receptacle portion 138 of a disinfection tray system 130. The alignment indicators may be electronic circuits (e.g., paired RF transceivers, electrical continuity circuits, optical alignment circuits, and the like) that indicate a suitable alignment of components or portions of components. The alignment indicators may be tactile structures such as protuberances and corresponding indentures of any suitable shape.

The sensor interface 172 is arranged to send control information to one or more sensors, receive data from one or more sensors, or both send control information and receive data to/from one or more sensors. The sensors may be ultraviolet (UV) radiation sensors (e.g., photo detectors), and in some of these cases, the UV sensors may be tuned for a particular UV frequency (e.g., UV-A radiation, UV-B radiation, or UV-C radiation). The sensors may be time-of-flight sensors. In some cases, the sensors include non-electronic sensors such as an UV-sensitive material (e.g., a paint that changes color when exposed to a particular type of radiation such as UV radiation). When the non-electronic sensor is a UV-sensitive material, the UV-sensitive material may change its appearance (e.g. color, brightness, texture, or the like) in relationship to the amount of radiation impinging on the sensor's surface (e.g., a first amount of radiation may change a white material to a pink material, and a second higher amount of radiation may change the material to a red material, and so on). Other sensors such as door-closed sensors, door-opened sensors, radiation source failure sensors, and other sensors are contemplated.

The communications interface 174 may be coupled to any one or more suitable data communication circuits. The data communications may, for example, include wired or wireless serial communication circuit structures, WiFi (i.e., 802.11-compatible) circuits, Ethernet circuits, cellular telecom circuits, inductive communication circuits, and any other suitable circuits. The communications interface may be arranged for bi-direction or unidirectional communications. The communications interface 174 of a disinfection tray system 130 may be arranged for communications with a corresponding communications interface 174 of a disinfection system 100. In some cases, two or more disinfection tray systems 130 may communicate with each other. In some cases, two or more disinfection systems 100 may communicate with each other. In some cases, the communications interface 174 is arranged to communicate with a wide area network (WAN) such as the Internet. In some cases, communications between relevant devices of the present disclosure is facilitated by passing information through a surrogate communications medium (e.g., a WAN, a local area network (LAN), or some other network).

The chamber software 166a and the tray software 166b include software instructions executable by the processor 162. The chamber software 166a and the tray software 166b may sometimes be organized as a set of logic modules. The logic modules of the executable software 166 may in some cases also include associated circuitry (e.g., switches, multiplexors, buffers, sensors, interface circuits, clock circuits, power circuits, compression/decompression circuits, encryption/decryption circuits, and the like). In at least some cases, one or more logic modules of the chamber software 166a are identical to one or more modules of the tray software 166b. In some cases, one or more of the logic modules of executable software 166 are shared by the chamber software 166a and the tray software 166b.

The chamber software 166a includes an identification module 176a, a disinfection module 178a, an alignment module 180a, a door control module 182a, a sensor control module 184a, and an additional logic module 186a. The tray software 166b includes an identification module 176b, a disinfected tray module 178b, an alignment module 180b, a time information module 182b, a sensor control module 184b, and an additional logic module 186b.

Each type of target article 120 may have a unique and specific type identifier. Each specific target article 120 may have a unique identifier. Along these lines, each disinfection tray system 130 may have a unique and specific type identifier, and each disinfection tray system 130 may have a unique identifier. The unique identifier may be arranged as a serial number or some other such identifier. Further still along these lines, each type of disinfection system 100 may have a unique and specific type identifier, and each disinfection system 100 may have a unique identifier. Hence, identification information, as the term is used herein, may include any or all of: 1) target article type identifiers, 2) disinfection tray system type identifiers, 3) disinfection system type identifiers, 4) target article identifiers, 5) disinfection tray system identifiers, and 6) disinfection system identifiers. Any or all of this identification information is suitably administered by one or both of the identification module 176a of the chamber software 166a and the identification module 176b of the tray software 166b. The identification information may be established by the manufacturer of the disinfection system 100, the disinfection tray system 130, and the target article 120 as the case may be. The identification information may be stored in a hardware circuit, a read-only portion of memory, or in some other way. The identification information may be encrypted or in clear text.

The identification module 176a of the chamber software 166a is associated with the specific identification information of the disinfection system 100. The identification module 176a is arranged to verify that particular operations of the disinfection system 100 may be performed based on the identification information. For example, the executable software 166 may have stored therein a large number (e.g., 10, 50, 500) of disinfection algorithms, but only certain ones of the disinfection algorithms may be suitable for execution in the particular disinfection chamber 102, and the determination of whether or not a disinfection algorithm is suitable for the disinfection system 100 may be based on the identification information. Additional information associated with the identification information may, under the direction and control of the identification module 176a, be communicated in to or out from the disinfection system 100 via the communications interface 174. In at least some cases, the identification information is accessible via a wide area network (e.g., the Internet). The identification information may be associated with other information of the disinfection system 100 such as, but not limited to, the age of the radiation sources 104, the number and types of radiation sensors 126, the number and types of registration features, disinfection tray compatibility information, disinfection cycle metadata (e.g., the number of disinfection cycles executed, time and date information, identification information associated with target articles or disinfection trays, errors, interrupted disinfection cycles, and the like), the size and shape of the interior volume 114, and suspension assembly information. Other types and uses for the identification information of the disinfection chamber 100 as administered by the identification module 176a are also contemplated.

The identification module 176b of the tray software 166b is associated with specific identification information of a disinfection tray system 130 and one or more target articles 120. In some cases, the identification module 176b and the communication interface 174 cooperate to send the disinfection tray identification information to a disinfection system 100. In these cases, the disinfection system 100 may validate whether or not the particular disinfection tray system 130 is compatible with the disinfection system 100. In these cases, the disinfection system 100 may validate whether or not the particular target article that is aligned in the disinfection tray system 130 is compatible with the disinfection system 100.

The identification module 176b of the disinfection tray system 130 may cooperate with the identification module 176a of the disinfection system 100 to maintain current information regarding the disinfection status of one or more disinfection tray systems 130 and additionally or alternatively one or more specific target articles 120. When a particular disinfection tray system 130 or a particular target article 120 is disinfected, for example, the associated identification information and additional metadata may be recorded such that a later audit or other analysis can determine when a device was disinfected, the success or failure of the disinfection, the parameters of the disinfection cycle, the specific disinfection system 100 that performed the disinfection cycle, and other such information.

Based on the identification information, the identification module 176b is arranged to verify that particular parameters of disinfection are met. The identification module 176b may determine the type of target article 120 that is stored in a receptacle of the disinfection tray system 130. The identification module 176b identity of the target article 120 that is stored in a receptacle of the disinfection tray system 130. The identification module 176b may determine if the target article 120 is properly aligned in the disinfection tray system 130.

The disinfection module 178a of the chamber software 166a is arranged to administer a disinfection cycle in a disinfection system 100. The disinfection module 178a may direct or otherwise control a timed disinfection algorithm, a radiation sensor-based disinfection algorithm, or a different type of disinfection algorithm. In some cases, the disinfection algorithm may be selected or otherwise controlled based on identification information of a disinfection tray system 130 or identification information of a target article.

The disinfected tray module 178b of the tray software 166b is arranged to determine or otherwise maintain information associated with a disinfection cycle to be performed, or having been performed, on the disinfection tray system 130. The disinfected tray module 178b may, for example, maintain metadata representing when the disinfection cycle was performed, whether or not the disinfection cycle was completed, whether a lid portion 152 of a disinfection tray system 130 has been opened since a disinfection cycle was performed, and whether or not any other particular conditions have been met.

The alignment module 180a of the chamber software 166a and the alignment module 180b of the tray software 166b may operate independently or cooperatively to determine whether a target article has been properly aligned in the receptacle portion 132 and whether a disinfection tray system 130 has been properly aligned in a disinfection chamber 102. The alignment module 180a, 180b, may work cooperatively with the sensor interface 172 and one or more registration features 124. The alignment of registration features (e.g., mechanical registration features, electromechanical registration features, electronic registration features) between the disinfection tray system 130 and the disinfection chamber 102, between a target article 120 and a receptacle 132, or between any other portions of the systems of interest may be determined based on light circuits (e.g., photo detectors, LED's, and the like), radio circuits (e.g., radio frequency (RF) transmitter/receiver pairs), electrical continuity circuits, or any other such circuits. The operation of such circuits, and the determination of alignment, is carried out in one or both of the alignment modules 180a, 180b.

One or both alignment modules 180a, 180b, may generate or otherwise direct output alert information to a user of the respective system via the user interface 170. The output information is provided to indicate to the user when at least one of a proper alignment condition and an improper alignment condition exists or has existed. The output alert information may be any one or more of audio information (e.g., buzzer, piezo device, bell, speaker-delivered alert, and the like), visual information (e.g., a light emitting diode (LED) illumination, a screen message, and the like), or tactile information (e.g., a vibrator, a piezo buzzer, or the like). In some cases, an alignment module 180a, 180b provides information into other circuitry of the disinfection system 100 and disinfection tray system 130 that is a prerequisite to the performance of a disinfection process. That is, the disinfection process in some cases is only performed if the relevant alignment modules 180a, 180b determine that the target article 120, disinfection tray system 130, and disinfection system 100 are all properly aligned. In at least one case, a determination of alignment is generated within a range of "insufficient alignment" to "sufficient alignment," and the range is used to control how long a portion of a disinfection process will be executed. Particularly, if alignment is determined to be a first value, then a disinfection process may execute for a first time period, and if alignment is determined to be a second value that is higher than the first value, then a disinfection process may execute for a second period of time that is shorter than the first time period. Such operations are in some cases facilitated by one or both alignment modules 180a, 180b.

The door control module 182a of the chamber software 166a may be used to lock a disinfection chamber door 112, unlock a disinfection chamber door 112, and alternatively or additionally provide an indication of a locked/unlocked state of a disinfection chamber door 112. The door control module 182a may direct operations of an interlock mechanism 112a. Additionally or alternatively, the door control module 182a may receive status information from an interlock mechanism 112a. In some cases, such as in the embodiment of FIG. 6E, the door control module 182a will control to and receive information from a plurality of doors of a disinfection system 100.

The time information module 182b of the tray software 166b may be used to determine when a target article 120 is aligned in the disinfection tray module. In these or other cases, the time information module 182b may be used to determine how long a disinfection tray system 130 has been exposed to radiation. The time information module in these or still other cases may be used to determine how long a lid portion 152 of a disinfection system 100 has been open, closed, or open and closed.

A sensor control module 184a of the chamber software 166a and a sensor control module 184b of the tray software 166b may operate independently or cooperatively. The sensor control module 184a, 184b may enable and disable a sensor, load parameters into a sensor, receive data from a sensor, and provide and receive any other information associated with a sensor. The sensor control modules 184a, 184b facilitate communication of control information and data via a sensor interface 172. A non-limiting list of sensors that may interact with the sensor control modules 184a, 184b include radiation sensors, door close sensors, alignment sensors, keyboards, computer mice, touch screens, and other human interfaces devices. Still other sensors are of course contemplated.

The additional logic module 186a of the chamber software 166a and the additional logic module 186b of the tray software 166b perform still other functions. Such logic may control or receive information from clock circuits, power measurement circuits, the user interface 170, the communications interface 174, and still other circuits. The additional logic modules 186a, 186b may further provide software instructions that, when executed by the processor 162, carry out still other functions of the disinfection system 100 and disinfection tray system 106, respectively.

Figure 8:
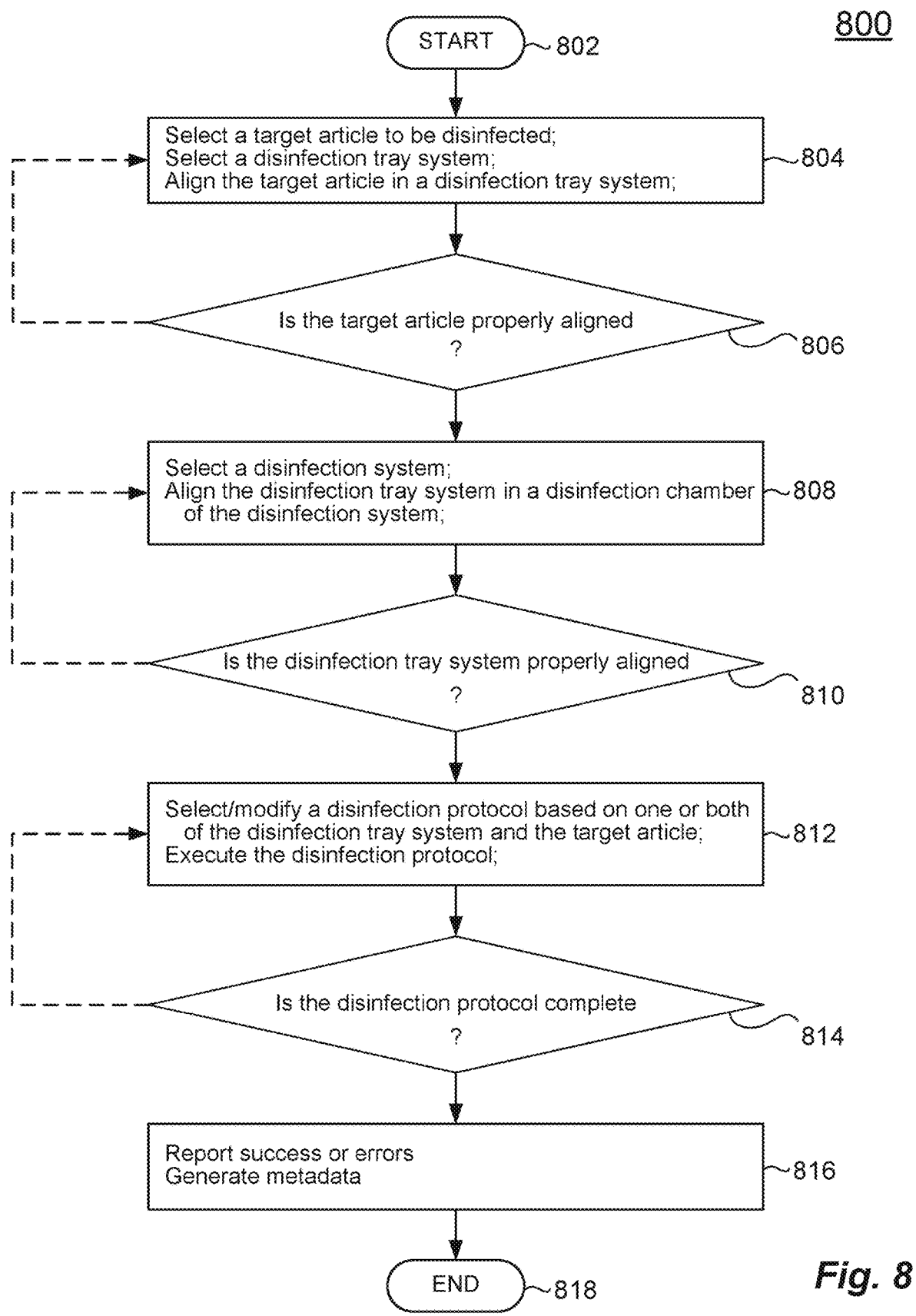
FIG. 8 is a data flow diagram representing a method of aligning a target article to be disinfected in disinfection tray system, placing the disinfection tray system in a disinfection system, and disinfecting the target article.

FIG. 8 is a data flow diagram 800 representing a method of aligning a target article 120 to be disinfected in disinfection tray system 130, placing the disinfection tray system 130 in a disinfection system 100, and disinfecting the target article 120. Processing in the data flow diagram 800 begins at 802 and advances to 804.

At 804, a user (e.g., a medical practitioner, a scientist, a manufacturer, or some other user) may determine that a target article 120 will be disinfected. The target article to be disinfected may be a probe of any particular type such as a probe used in a medical setting, a dental instrument, device used in the development or manufacture of electronic components, a device used in the manufacture of pharmaceuticals, a cable, a handle, or any other device that the user determines should be disinfected.

Next, the user selects a disinfection tray system 130 and aligns the target article 120 to be disinfected in a receptacle portion 138 of a tray portion 134 of the disinfection tray system 130. The tray portion is formed from a UV-transparent material. The UV-transparent material may include one or more of plastic, vinyl, glass such as quartz, gel, a polymer, poly-methyl methacrylate (PMMA), polystyrene, or some other UV-transparent material. The UV-transparent material may in some cases be at least 50 percent (50%) UV-transparent, at least 75 percent (75%) UV-transparent, at least 95 percent (95%) UV-transparent, or UV-transparent to some other level.

The disinfection tray system 130 may be a molded structure, a blow-molded structure, a laser-cut structure, a heat-formed structure, a poured structure, a machined structure, or a structure formed in some other way. The disinfection tray system 130 may in some cases be arranged for use a single time. That is, the disinfection tray system 130 may in some cases be a disposable device. In other cases, certain portions of the disinfection tray system 130 are arranged for use a single time (e.g., disposable portions). In still other cases some or all portions of the disinfection tray system 130 are reusable.

The disinfection tray system 130 may be arranged to include a receptacle portion 138. The receptacle portion 138 has a defined shape (e.g., a shape of the target article 120 to be disinfected) and a defined dimension (e.g., a size of the target article 120 to be disinfected). The receptacle portion 138 may have any number of different sections that are sunken in the surface of the tray portion 138. Alternatively, the receptacle portion may include a plurality of one or more alignment receptacle portions such as clips or some other binding means. The surface of the tray portion 138 may include a template, outline, image of a target article to be disinfected or some other visual alignment means that guides the user toward proper placement of the target article to be disinfected in the disinfection tray system 130.

In some cases, the receptacle portion 138 of the disinfection tray system 130 may include registration features that mate or otherwise cooperate with selected portions of the target article to be disinfected 120. For example, when a receptacle 132 is embedded into the surface of the tray portion 134, the receptacle may have one or more primary receptacle portions 138a, one or more secondary receptacle portions 138c, one or more alignment receptacle portions 138b, and any other number of suitable portions. In at least some cases, the receptacle 132 includes one or more alignment receptacle pass-through portions 142 that permit a cable, hose, or some other part of the target article 120 to be disinfected to extend beyond a boundary of the tray portion 134.

At 806, and in combination with the processing at 804, a determination is made whether or not the target article 120 to be disinfected is properly aligned in the receptacle portion 138 of the disinfection tray system 130.

When the user aligns the target article 120 to be disinfected in the receptacle portion 138, proper alignment of the target article 120 may be determined visually, tactilely, electronically, or in some other way. For example, the receptacle portions may provide low tolerance cut outs (e.g., cut outs within 50 millimeters, within 10 millimeters, within 2 millimeters, or within some other tolerance between a boundary of the target article and a corresponding boundary of the receptacle). The low tolerance cut outs permit a user to tactilely know whether or not the target article 120 is properly aligned in the disinfection tray system 130.

In addition, or in the alternative, the disinfection tray system 130 may include electronic means of determining that the target article 120 to be disinfected is properly aligned in the receptacle portion 138. The electronic means may include optical pairs, radio frequency receiver/transmitter pairs, electrical continuity points, or some other electronic circuits arranged to determine that the target article 120 is properly aligned.

In still other cases, proper alignment is achieved by a user visually observing that the target article to be disinfected is placed in the receptacle portion according to written instructions, a template, a visual representation printed or otherwise displayed on the disinfection tray system 130 such as within the boundaries of the receptacle portion 138.

A disinfection tray system 130 of the types taught in the present disclosure may optionally include a controller such as controller 160 of FIG. 7. The controller 160 may be arranged as an electronics module having a communications interface, a user interface (e.g., audio interface, visual interface, tactile interface, or the like), at least one clean/not-clean indicator (e.g., a color-coded indicator, a flashing/not-flashing indicator, an audible/silent indicator, or some other indicator), a time-of-last-clean indicator, a disinfection "expired"/"not expired" indicator, a serial number or some other identifier repository or circuit, an encryption/decryption module, and any other suitable circuitry. In some cases, the electronics module may be hermetically sealed in the tray portion 138. In other cases, the electronics module is attachable to the disinfection tray system 130 or in proximity to the disinfection tray system 130.

The electronics module is arranged to communicate identification information associated with the target article 120 to be disinfected, along with any other desirable information, from the disinfection tray system 130 to a disinfection system 100. The electronics module may also communicate such information to some other computing devices such as a computing server communicatively coupled to a network such as the Internet.

If the target article 120 to be disinfected is properly aligned in the disinfection tray system 130, processing falls to 808. If the target article 120 to be disinfected is not properly aligned in the disinfection tray system 130, processing at 806 returns to 804.

Processing falls to 808 where a particular disinfection system 100 is selected to receive the disinfection tray system 130. The disinfection tray system 130 is aligned in the disinfection system 100 at 808, and a determination is made at 810 as to whether or not the disinfection tray system 130 is properly aligned in the disinfection system 100.

In some cases, aligning the disinfection tray system 130 includes placing the disinfection tray system 130 into a disinfection chamber 102 using one or more handle structures integrated with, or coupled to, the disinfection tray system 130. In some cases, the disinfection tray system 130 includes at least two handles. In these cases, each of the handles is arranged for removable coupling to a corresponding handle attachment structure. The handles, may, for example include hooks, clamps, or the like that fit into holes, loops, or some other structure of the disinfection tray system 130.

To assist with alignment, the disinfection tray system 130 may include an alignment portion having a defined shape and a defined dimension. The defined shape may be the shape of the tray portion 134 of the disinfection tray system 130. Exemplary but non-limiting shapes include a cuboid, which may be defined as a square or a rectangle, a rectangular parallelepiped, a convex polyhedron bounded by six quadrilateral faces, a rectangular box, or by any other like definition. Other geometrically simple shapes (e.g., spherical shapes, pyramidal shapes) are contemplated. Other complex shapes are also contemplated. The defined shape in some cases is selected to provide line of sight exposure, more proximal exposure, or some other element of exposure of one or more selected portions of the target article 120 to be disinfected to one or more radiation sources 104 of the disinfection system 100. For example, a shape of a disinfection tray system 130 may be fully or partially selected to place a "front" (i.e., patient-contact) portion of a medical probe in close, line-of-sight proximity to a particular radiation source 104 in the disinfection system 100.

In some cases, when an optional first electronics module (e.g., controller 160) is included in the disinfection tray system 130, the first electronics module is arranged to communicate with a corresponding second electronics module (e.g., controller 160) of the disinfection system 100. The first electronics module may communicate identification information to the second electronics module thereby informing the disinfection system 100 of the identity (e.g., serial number, type of target article) of the target article 120 to be disinfected. Other information may also be communicated between the first and second electronics modules.

The disinfection tray system 130 may optionally include an alignment portion having any number of registration features. The registration features may include the shape and one or more dimensional values associated with the disinfection tray system 130. The registration features may further include any number of optional physical alignment structures or electronic circuits that assist in aligning the disinfection tray system 130 within the disinfection chamber 102 of the disinfection system 100.

In at least some cases, particularly where the alignment of the disinfection tray system 130 in the disinfection system 100 is determined electronically, the alignment information can be communicated between the disinfection tray system 130 and the disinfection system 100. The alignment information may be an indication that the structures are properly aligned. Alternatively, the alignment information may be that the structures are not properly aligned. Based on the alignment information, the user may be alerted by an audible indicator, a visual indicator, a tactile indicator, or some other indicator. Such information may be suitably communicated in some cases between the disinfection tray system 130 and the disinfection system 100.

If the disinfection tray system 130 is properly aligned in the disinfection system 100, processing falls to 812. If the disinfection tray system 130 is not properly aligned in the disinfection system 100, processing at 810 returns to 808.

At 812, a disinfection protocol is selected by the disinfection system 100 based on one or both of the disinfection tray system 130 and the target article 120 to be disinfected, and the disinfection protocol is executed. Because some or all portions of the disinfection tray system 130 are formed from radiation-transparent material, radiation from the radiation sources 104 passes through the disinfection tray system 130, reaches the target article 120, and disinfects the target article.

The disinfection protocol may enable one or more radiation sources 104 based on time, based on radiation delivered to one or more radiation sensors, or based on some other function. In some cases, with knowledge of the target article 120, the disinfection protocol can expressly control one or more radiation sources 104 to provide a particular disinfection outcome. For example, one or more radiation sources 104 in the disinfection chamber 102 may be enabled for a longer time than other radiation sources 104 in the disinfection chamber 102. In addition, or in the alternative, one or more radiation sources 104 in the disinfection chamber 102 may be pulsed or enabled in other ways to prevent overheating of a portion of the target article 120.

In some cases, radiation sensors embedded in, or otherwise associated with, the disinfection tray system 130 provide information to the disinfection system 100 regarding continuation or termination of the disinfection protocol. In these cases, for example, the disinfection tray system 130 collects radiation sensor information and communicates the radiation sensor information to the disinfection system 100. The disinfection system 100 may use the radiation sensor information to determine when to end a disinfection process, when to extend a disinfection process, and when to modify a disinfection process. One example of modifying a disinfection process includes extending the enablement of a first one or more radiation sensors 104 to continue radiating and concurrently disabling a second one or more radiation sensors 104 to terminate radiating. In this way, a first selected portion of the target article 120 can continue to receive direct, line-of-sight radiation, and second selected portion of the target article 120 will stop or reduce the amount of direct line-of-sight radiation that is received.

If the disinfection system 100 at 814 determines that the disinfection protocol is complete, then processing advances to 816. Alternatively, if the disinfection protocol is not complete, then processing returns to 812.

At 816, one or both of the disinfection tray system 130 and the disinfection system 100 can report success or failure of the disinfection process, and one or both of the disinfection tray system 130 and the disinfection system 100 can optionally generate metadata associated with the disinfection process. Success or failure may be reported electronically via a user interface (e.g., an audible alert, a visual indicator, or the like). Success or failure may additionally or alternatively be reported via a physical medium such as a radiation-sensitive material as taught in the present disclosure. The radiation-sensitive material may be integrated with, coupled to, or otherwise associated with the disinfection tray system 130.

The metadata generated at 816 may include timing information such as a timestamp and a date stamp identifying when the disinfection process was conducted. The timing information may be specifically coupled or otherwise associated with identification information of the target article 120, the disinfection tray system 130, or both the target article 120 and the disinfection tray system 130. In at least some cases, the disinfection tray system 130 includes a mechanically sealable case (e.g., container 146) arranged to hold at least one tray portion 134. The mechanically sealable case may be used to store the target article 120 for hours, days, weeks, months, or for some other period of time. In these and at least some other cases, the metadata optionally include disinfection-expiration timing information. This disinfection-expiration timing information informs a user when the target article 120 should be re-disinfected if the target article 120 has not been used.

Still other metadata may be collected and communicated in any useful way. The other metadata may include parameters of the disinfection process that were dynamically changed. Such information may be used to detect imminent or pending problems with the disinfection tray system 130 and the disinfection system 100. Other metadata may include the number of times a particular target article 120 has been disinfected, the number of times a particular disinfection tray system 130 has been disinfected, the cumulative amount of radiation collected by radiation sensors, the duration of disinfection process, and any other information associated with the disinfection process.

Processing from 816 falls and terminates at 818.

In the foregoing description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments.

Turning back to FIG. 1, each radiation source 104 may emit radiation light rays according to its own parameters and characteristics. For example, the age of a radiation source 104 may be directly related to the light emitting characteristic thereof. Further, the time lapse after a radiation source is turned on may also affect the UV-C radiation emitted from the radiation source 104. For example, the intensity of radiation light emitted by a radiation source 104 may, as part of its natural operation, be time dependent and may include a specific pattern of waveform/variations, e.g., continuous decreasing, continuous increasing, or fluctuating. Further, each radiation source 104 may include different operation states of emitting the radiated light. For example, each radiation source 104 may have characteristics that cause the respective source to radiate at different power levels even when the output power of two or more radiation sources 104 is otherwise expected to be the same. Each radiation source 104 may also emit radiation light rays at different angles, substantially parallel to each other, or a combination of attitudes in operation. And a plurality of radiation sources may be controlled with common signals and common parameters. Alternatively, two or more radiation sources may be independently controlled via independent control signals and parameters.

A disinfection chamber 102 as described herein may be configured to create a plurality of disinfection regions within the interior volume 114. In such embodiments, the disinfection chamber 102 and/or one or more target articles 120 to be disinfected can be further configured such that the one or more target articles 120 to be disinfected are positioned within the disinfection regions in selected positions, alignments, orientations, or the like. As used herein, the term "disinfection region" refers to a region within the disinfection chamber wherein a certain intensity of disinfecting radiation is delivered over the course of a disinfection process. In specific embodiments, the interior volume 114 is coupled to one or more sources 104 of UV-C radiation, and the one or more sources 104 of UV-C radiation are selected and arranged to deliver, independently or in common, UV-C radiation to the disinfecting regions at a varying radiation intensity, namely irradiance (also referred to as "power" to or through a specific unit of area) of, e.g., at least about 1,500 µW/cm². In this way, via the plurality of disinfection regions and the independent or common control of radiation sources, more precise delivery of radiation may be possible within the interior volume 114 of the respective chamber.

In some embodiments, the one or more radiation sources 104 of UV-C radiation may be selected to emit UV-C light within a band selected from between about 240 nm and about 270 nm and between about 255 nm and about 265 nm. For example, one or more UV-C source(s) 104 may be selected and arranged such that one or more disinfection regions are formed within the disinfection chamber, and the radiation intensity ("irradiance") of the UV-C radiation delivered to the one or more disinfecting regions is between about 1,500 µW/cm² and about 5,000 µW/cm². In further embodiments, the one or more UV-C source(s) 104 may be selected and arranged to provide one or more disinfecting regions wherein the irradiance of the UV-C radiation delivered within the disinfection region(s) is selected from between about 1,500 µW/cm² and about 2,000 µW/cm², between about 1,500 µW/cm² and about 2,500 µW/cm², between about 1,500 µW/cm² and about 3,000 µW/cm², between about 2,000 µW/cm² and about 2,500 µW/cm², between about 2,000 µW/cm² and about 3,000 µW/cm², between about 2,000 µW/cm² and about 3,500 µW/cm², between about 2,000 µW/cm² and about 2,500 µW/cm², between about 2,000 µW/cm² and about 2,750 µW/cm², between about 2,500 µW/cm² and about 2,600 µW/cm², between about 2,500 µW/cm² and about 2,750 µW/cm², and between about 2,500 µW/cm² and about 3,000 µW/cm², or between other like values.

In some embodiments, a disinfection region created within the interior volume 114 is characterized by the delivery of disinfecting radiation at a substantially uniform irradiance within the region. As used herein in reference to a disinfecting region, the term "substantially uniform" refers to a region within which the irradiance of the disinfecting radiation does not vary by more than 10% within the entire region (i.e., the irradiance measured within the region does not vary by more than 10%). In particular embodiments, "substantially uniform surface irradiation" refers to a disinfecting region wherein the intensity at which the disinfecting radiation is delivered to the surface(s) of the article to be disinfected does not vary across any portion of those surface(s) by more than an amount selected from ±30%, ±25%, ±20%, ±15%, ±10%, and ±5% or another like value. The disinfection regions may be re-defined or custom-tuned for different types of target articles 120, different regions of target articles 120 intended for disinfection, different operational states of radiation sources 104, or for other reasons. Further, the disinfection regions may be dynamically adjusted, collectively adjusted, independently adjusted, or adjusted in some other way. For example, if it is determined that the radiation intensity variation within a disinfection region is beyond a threshold, e.g., 10%, the disinfection region may be redefined into two or more disinfection regions according to a generated disinfection program, for example, or by some other logic.

Though disinfection does not require that radiation be delivered uniformly, it may be useful to have reasonably uniform irradiance in a local volume/region within which a target article 120 is positioned. A uniform distribution may be used to confirm the actual power level that is established where one or more surfaces of a target article 120 are being disinfected. For example, when a selected volume or region is uniformly irradiated, the radiation dosage reaching one or more surfaces in the selected volume or region may be inferred from a sensor measurement of radiation in the selected volume or region. In this way, a minimum dose of radiation that is determined to achieve the level of disinfection desired may be delivered to an intended surface and the chance of overexposure can be reduced.

The one or more interior walls defining the interior volume 114 of the disinfection chamber 102 may also be configured to work in conjunction with the one or more radiation sources 104 of disinfecting radiation to deliver high intensity disinfecting radiation to the one or more disinfection regions within interior volume 114. For example, the one or more walls included in the disinfection chamber and, where included, the one or more reflective surfaces, can be configured to function in cooperation with the one or more radiation sources 104 of disinfecting radiation to provide one or more disinfection regions. In some embodiments, the interior volume of the disinfection chamber is defined by one or more sidewalls with a top and/or a bottom wall. In such embodiments, sources 104 of disinfecting radiation can be positioned on or within any sidewall, top wall, bottom wall, or at any junction between any of two or more sidewalls, a sidewall and a bottom wall, and a sidewall and a top wall. In addition, or in the alternative, a generated disinfection program may control one or more radiation sources 104 to deliver one or more desired levels of radiation to one or more different disinfection regions defined in the interior volume 114 of the disinfecting chamber 102. And the radiation intensity delivered to one disinfection region may concurrently be different from the radiation intensity delivered to another disinfection region.

The one or more walls defining the interior volume 114 of the disinfection chamber 110 can provide any one of many cross-sectional shapes for the chamber. For example, in particular embodiments, the one or more walls are configured to provide an interior volume 114 having a circular or multi-sided cross section, such as a rectangular, triangular, hexagonal or octagonal cross section. In some embodiments, the disinfection chamber 102 is configured such that the interior volume 114 is defined by a plurality of walls and the cross-sectional shape of the interior volume is a rectangular parallelepiped or an octagonal parallelepiped. In still other embodiments, the interior volume 114, or portions thereof, may be shaped as a circle, a parabola, a double ellipse, or some other shape. In some cases, interior walls of the interior volume 114 may be added, removed, or alternatively or in addition re-positioned so that a disinfection chamber having an interior volume defined by a first cross-sectional shape is modified to have an interior volume defined by a second, different cross-sectional shape.

Embodiments of the disinfection chamber 102 may include a reflector (not specifically shown for simplicity) totally or partially behind the one or more disinfecting radiation source(s) 104, and in such embodiments, where the source 104 of disinfecting radiation emits UV radiation and is a line source, such as, for example, a tube that emits UV-C radiation, the reflector may be parabolic, with the UV-C radiation source at or near its focus. Such a configuration can result in sending light, upon its initial reflection from the parabolic reflector, being sent out in mostly parallel rays. Of course other reflector geometries, UV radiation source locations, and resulting radiation fields are possible. Where tubes emitting UV-C radiation are used as the one or more sources of disinfecting radiation, in some embodiments, the rated total power delivered by the source tubes (i.e., UV-C fluence leaving the source, integrated over a surface area that encompasses the source) may range from about 20 W to about 200 W. The input electrical power consumed by disinfecting radiation source(s) 104 (e.g., UV tubes) is related and informative of the output UV power delivered from these sources, but it is noted that the relationship is not linear, and the relationship will generally change over time. In specific embodiments, however, the input power for UV tubes used in a disinfection chamber as described herein may be selected from, for example, 20 W, 25 W, 30 W, 35 W, 40 W, 45 W, 50 W, 55 W, 60 W, 65 W, 70 W, 75 W, 80 W, 85 W, 90 W, 95 W, 100 W, 135 W, 150 W, or another like value.

One or more sources 104 of disinfecting radiation may be positioned around the one or more sidewalls of the interior volume 114 in a manner that results in radiation of a selected intensity (such as, e.g., energy of an intensity as described in relation to the disinfection regions) being delivered to the one or more disinfection regions within interior volume 114. The one or more sources 104 of disinfecting radiation can be positioned around the interior volume 114 to provide a disinfection region with a certain radiation intensity. For example, in embodiments of the interior volume 114 having one or more sidewalls, two or more sources 104 of disinfecting radiation, such as two or more sources 104 of UV-C radiation may be positioned along one or more of the sidewalls at uniformly spaced locations. In embodiments having multiple sidewalls, one or more sources 104 of disinfecting radiation may be positioned at one or more corners of the sidewalls. Where the disinfection chamber includes at least one top or bottom wall or surface, one or more sources 104 of disinfecting radiation can be positioned at a top and/or bottom wall or surface to provide a certain level of irradiance of disinfecting radiation directed into one or more disinfection regions formed within the interior volume 114. In specific embodiments, where the interior volume 114 of the disinfection chamber 102 is configured to include two or more sidewalls and a bottom wall, with a UV radiation source 104 at each corner formed between the sidewalls and at least one UV radiation source 104 positioned at the bottom wall, the input power of each corner tube may be at least 50 W, and where included, the power of the bottom one or more tubes may be at least 30 W.

To facilitate positioning of target articles 120 within the interior volume 114, the disinfection chamber 102 can be provided with a moveable base, e.g., a suspension assembly, which positions one or more target articles 120, e.g., an ultrasound probe or other medical instrument, within the chamber. A suspension assembly as described herein works to position one or more target articles 120 to be disinfected consistently within the disinfection chamber. In these cases, where the disinfection chamber is designed to create one or more disinfection regions, providing a suspension assembly allows consistent, repeatable positioning of the one or more articles to be disinfected within disinfection region(s), thereby ensuring the one or more articles are subjected to high intensity radiation during a disinfection cycle.

As will be appreciated, the positions of the shape and size of interior volume 114, the position, shape, and light reflective properties of reflective interior sidewalls that define interior volume 114, the amount and positions of radiation sources 104, the movement of moveable base and other structural configurations of interior volume 114 may all affect the radiation intensity delivered to a disinfection region within interior volume 114. In the description herein, all such structural configurations of and/or within interior volume 114 are referred to as "structural configurations" of interior volume 114.

The number and positioning of the one or more sensors 126 included in the disinfection system 100 are also selected to provide rapid, high-level disinfection at a low temperature. For purposes of the present description, a sensor 126 includes any device or assembly of components that collects and measures an environmental condition. When referring to one or more sensors 126 for detecting disinfecting radiation within the disinfection chamber, the one or more sensors 126 will each be a device or assembly of components capable of collecting information regarding the disinfecting radiation present in the disinfection chamber, sensing or measuring the amount of disinfecting radiation within the disinfection chamber, and amplifying or processing the collected information regarding the disinfecting radiation. Further, in the context of the present description, a sensor 126 is considered to be positioned within the disinfection chamber 102 where any component of the sensor 126 is capable of detecting, measuring, transmitting, processing, or communicating processed information regarding the disinfecting radiation present within the disinfection chamber, whether or not it is positioned within or directly exposed to the interior of the disinfecting chamber.

Each of the one or more sensors 126 included in the interior volume 114 may be capable of detecting and communicating information such as a total radiation dose, a rate of exposure over time, and the like, to controller 160. For example, where UV-C light is used as the disinfecting radiation, the sensors 126 may sense the UV-C dose received by the target article 120 and/or the amount of UV-C radiation emitted by one or more UV-C sources 104 included in the disinfection device. In some embodiments, UV-C sensors 126 included in the disinfection devices described herein may be, or otherwise include, one or more photodiodes fixedly or movably positioned within the interior volume 114 of the disinfection chamber 102. In these and in other embodiments, the one or more sensors 126 may comprise one or more light conducting components such as lenses, mirrors, filters and other optical elements used to collect radiation within the chamber, and may also comprise fiber optic cables or light pipes that conduct the collected disinfecting energy to a detector, such as a photodiode. Sensors 126 may be standalone sensors or sensors 126 may be formed as a combination of discrete structures (e.g., a fiber optic probe (FOP) that includes at least one light conductive element and at least one photo electric sensor coupled into a common structure. In some variations, the sensors 126 within the disinfection chamber 102 are configured to have a band-pass optical filter or other electromagnetic filter in front of them so that only radiation in the spectrum of interest is sensed. In some embodiments, one or more sensors 126 may be positioned on or incorporated into the one or more articles to be disinfected. Positioning of one or more sensors 126 on the one or more target articles 120 to be disinfected may provide more accurate reading of the disinfecting radiation reaching the article 120. The devices described herein may include one or more sensors 126 that utilize, for example, multiple optical conductors positioned to monitor direct and indirect sources of the disinfecting radiation. Photonic conductors useful in the context of the devices described herein include, but are not limited to, fiber optic "cable" (suitable for conducting light over a long distance with low loss) or a simple "light pipe" formed of a glass, polymer, or other simple, optically transparent material that traps and contains light within itself and conducts the light with low loss. Where used, a "light pipe" as referenced herein is typically more suited to conducting light over short distances to prevent undesirable losses. A lens may be used to gather radiation and direct it to a detecting device, or the gathered radiation may be transported to another location for measurement.

It may be beneficial in some embodiments to include one sensor 126 or a set of sensors 126 to detect the global (i.e., aggregate) radiation dosage delivered to the interior volume 114 and another sensor 126 or set of sensors 126 to check or monitor each disinfection region, source, or other feature within interior volume 114.

In one embodiment, a disinfection system 100 is controlled by controller 160 to direct operation of a radiation source 104 with a specified power level and a specific period of time, namely to reach a determined cumulative threshold radiation dosage. For example, where UV-C radiation is used as the disinfecting radiation, in particular embodiments, the predetermined threshold dose may be selected from between about 50,000 $\mu J/cm^2$ and about 10,000,000 $\mu J/cm^2$. In certain such embodiments, the dose may be selected from between about 50,000 $\mu J/cm^2$ and about 1,000,000 $\mu J/cm^2$, such as, for example, a dose selected from between about 50,000 $\mu J/cm^2$ and about 750,000 $\mu J/cm^2$, between about 50,000 $\mu J/cm^2$ and about 650,000 $\mu J/cm^2$, between about 50,000 $\mu J/cm^2$ and about 500,000 $\mu J/cm^2$, between about 50,000 $\mu J/cm^2$ and about 450,000 $\mu J/cm^2$, between about 50,000 $\mu J/cm^2$ and about 350,000 $\mu J/cm^2$, between about 50,000 $\mu J/cm^2$ and about 250,000 $\mu J/cm^2$, and between about 50,000 $\mu J/cm^2$ and about 100,000 $\mu J/cm^2$, or between other like values. In further such embodiments, the dose may be selected from between about 150,000 $\mu J/cm^2$ and about 750,000 $\mu J/cm^2$, between about 150,000 $\mu J/cm^2$ and about 650,000 $\mu J/cm^2$, between about 150,000 $\mu J/cm^2$ and about 500,000 $\mu J/cm^2$, between about 150,000 $\mu J/cm^2$ and about 450,000 $\mu J/cm^2$, between about 150,000 $\mu J/cm^2$ and about 350,000 $\mu J/cm^2$, and between about 150,000 $\mu J/cm^2$ and about 250,000 $\mu J/cm^2$, or between other like values. In still further such embodiments, the dose may be selected from between about 250,000 $\mu J/cm^2$ and about 750,000 $\mu J/cm^2$, between about 250,000 $\mu J/cm^2$ and about 650,000 $\mu J/cm^2$, between about 250,000 $\mu J/cm^2$ and about 500,000 $\mu J/cm^2$, between about 250,000 $\mu J/cm^2$ and about 450,000 $\mu J/cm^2$, and between about 250,000 $\mu J/cm^2$ and about 350,000 $\mu J/cm^2$, or between other like values.

Having now set forth certain embodiments, further clarification of certain terms used herein may be helpful to providing a more complete understanding of that which is considered inventive in the present disclosure.

In the embodiments of present disclosure, one or more particular disinfection structures may include a controller 150 and integrated or otherwise associated electronic circuits. The various components and devices of the embodiments are interchangeably described herein as "coupled," "connected," "attached," and the like. The materials and the junctions formed at the point where two or more structures meet in the present embodiments are joined to a mechanically, medically, or otherwise industrially acceptable level.

FIG. 8 includes a data flow diagram illustrating a non-limiting process that may be used by embodiments of disinfection systems 100 and disinfection tray systems 130. In this regard, each described process may represent a module, segment, or portion of software code, which comprises one or more executable instructions for implementing the specified logical function(s). It should also be noted that in some implementations, the functions noted in the process may occur in a different order, may include additional functions, may occur concurrently, and/or may be omitted.

The figures in the present disclosure illustrate portions of one or more non-limiting computing device embodiments such as one or more components of controller 160. The computing devices may include operative hardware found in conventional computing device apparatuses such as one or more processors, volatile and non-volatile memory, serial and parallel input/output (I/O) circuitry compliant with various standards and protocols, wired and/or wireless networking circuitry (e.g., a communications transceiver), one or more user interface (UI) modules, logic, and other electronic circuitry.

Processing devices, or "processors," as described herein, include central processing units (CPU's), microcontrollers (MCU), digital signal processors (DSP), application specific integrated circuits (ASIC), peripheral interface controllers (PIC), state machines, and the like. Accordingly, a processor as described herein includes any device, system, or part thereof that controls at least one operation, and such a device may be implemented in hardware, firmware, or software, or some combination of at least two of the same. The functionality associated with any particular processor may be centralized or distributed, whether locally or remotely. Processors may interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, one or more embodiments describe software executable by the processor, which when executed, carries out one or more of the method acts.

The present application discusses several embodiments that include or otherwise cooperate with one or more computing devices. It is recognized that these computing devices are arranged to perform one or more algorithms to implement the inventive concepts taught herein. Each of said algorithms is understood to be a finite sequence of steps for solving a logical or mathematical problem or performing a task. Any or all of the algorithms taught in the present disclosure may be demonstrated by formulas, flow charts, data flow diagrams, narratives in the specification, and other such means as evident in the present disclosure. Along these lines, the structures to carry out the algorithms disclosed herein include at least one processing device executing at least one software instruction retrieved from at least one memory device. The structures may, as the case may be, further include suitable input circuits known to one of skill in the art (e.g., keyboards, buttons, memory devices, communication circuits, touch screen inputs, and any other integrated and peripheral circuit inputs (e.g., accelerometers, thermometers, light detection circuits and other such sensors)), suitable output circuits known to one of skill in the art (e.g., displays, light sources, audio devices, tactile devices, control signals, switches, relays, and the like), and any additional circuits or other structures taught in the present disclosure. To this end, every invocation of means or step plus function elements in any of the claims, if so desired, will be expressly recited.

As known by one skilled in the art, a computing device has one or more memories, and each memory comprises any combination of volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. The memory in some cases is a non-transitory computer medium configured to store software instructions arranged to be executed by a processor. Some or all of the stored contents of a memory may include software instructions executable by a processing device to carry out one or more particular acts.

The computing devices illustrated herein may further include operative software found in a conventional computing device such as an operating system or task loop, software drivers to direct operations through I/O circuitry, networking circuitry, and other peripheral component circuitry. In addition, the computing devices may include operative application software such as network software for communicating with other computing devices, database software for building and maintaining databases, and task management software where appropriate for distributing the communication and/or operational workload amongst various processors. In some cases, the computing device is a single hardware machine having at least some of the hardware and software listed herein, and in other cases, the computing device is a networked collection of hardware and software machines working together in a server farm to execute the functions of one or more embodiments described herein. Some aspects of the conventional hardware and software of the computing device are not shown in the figures for simplicity.

When so arranged as described herein, each computing device may be transformed from a generic and unspecific computing device to a combination device arranged comprising hardware and software configured for a specific and particular purpose such as to provide a determined practical application and technical solution. When so arranged as described herein, to the extent that any of the inventive concepts described herein are found by a body of competent adjudication to be subsumed in an abstract idea, the ordered combination of elements and limitations are expressly presented to provide a requisite inventive concept by transforming the abstract idea into a tangible and concrete practical application of that abstract idea.

The embodiments described herein use computerized technology to improve the technology of disinfection, but there other techniques and tools remain available to disinfect target articles. Therefore, the claimed subject matter does not foreclose the whole or even substantial disinfection technological area. The innovation described herein uses both new and known building blocks combined in new and useful ways along with other structures and limitations to create something more than has heretofore been conventionally known. The embodiments improve on computing systems which, when un-programmed or differently programmed, cannot perform or provide the specific disinfection system features claimed herein. The embodiments described in the present disclosure improve upon known disinfection processes and techniques. The computerized acts described in the embodiments herein are not purely conventional and are not well understood. Instead, the acts are new to the industry. Furthermore, the combination of acts as described in conjunction with the present embodiments provides new information, motivation, and business results that are not already present when the acts are considered separately. There is no prevailing, accepted definition for what constitutes an abstract idea. To the extent the concepts discussed in the present disclosure may be considered abstract, the claims present significantly more tangible, practical, and concrete applications of said allegedly abstract concepts. And said claims also improve previously known computer-based systems that perform disinfection operations.

Software may include a fully executable software program, a simple configuration data file, a link to additional directions, or any combination of known software types. When a computing device updates software, the update may be small or large. For example, in some cases, a computing device downloads a small configuration data file to as part of software, and in other cases, a computing device completely replaces most or all of the present software on itself or another computing device with a fresh version. In some cases, software, data, or software and data is encrypted, encoded, and/or otherwise compressed for reasons that include security, privacy, data transfer speed, data cost, or the like.

Database structures, if any are present in the disinfection systems described herein, may be formed in a single database or multiple databases. In some cases hardware or software storage repositories are shared amongst various functions of the particular system or systems to which they are associated. A database may be formed as part of a local system or local area network. Alternatively, or in addition, a database may be formed remotely, such as within a distributed "cloud" computing system, which would be accessible via a wide area network or some other network.

Input/output (I/O) circuitry and user interface (UI) modules include serial ports, parallel ports, universal serial bus (USB) ports, IEEE 802.11 transceivers and other transceivers compliant with protocols administered by one or more standard-setting bodies, displays, projectors, printers, keyboards, computer mice, microphones, micro-electro-mechanical (MEMS) devices such as accelerometers, and the like.

In at least one embodiment, devices such as the controller 160 may communicate with other devices via communication over a network. The network may involve an Internet connection or some other type of local area network (LAN) or wide area network (WAN). Non-limiting examples of structures that enable or form parts of a network include, but are not limited to, an Ethernet, twisted pair Ethernet, digital subscriber loop (DSL) devices, wireless LAN, Wi-Fi, Worldwide Interoperability for Microwave Access (WiMax), or the like.

In the present disclosure, memory may be used in one configuration or another. The memory may be configured to store data. In the alternative or in addition, the memory may be a non-transitory computer readable medium (CRM). The CRM is configured to store computing instructions executable by a processor of the controller 160. The computing instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of a disinfection system.

Buttons, keypads, computer mice, memory cards, serial ports, bio-sensor readers, touch screens, and the like may individually or in cooperation be useful to a user operating the disinfection system. The devices may, for example, input control information into the system. Displays, printers, memory cards, LED indicators, temperature sensors, audio devices (e.g., speakers, piezo device, etc.), vibrators, and the like are all useful to present output information to the user operating the disinfection system. In some cases, the input and output devices are directly coupled to the controller 160 and electronically coupled to a processor or other operative circuitry. In other cases, the input and output devices pass information via one or more communication ports (e.g., RS-232, RS-485, infrared, USB, etc.).

As described herein, for simplicity, a user may in some cases be described in the context of the male gender. It is understood that a user can be of any gender, and the terms "he," "his," and the like as used herein are to be interpreted broadly inclusive of all known gender definitions. As the context may require in this disclosure, except as the context may dictate otherwise, the singular shall mean the plural and vice versa; all pronouns shall mean and include the person, entity, firm or corporation to which they relate; and the masculine shall mean the feminine and vice versa.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, the technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

In the present disclosure, when an element (e.g., component, circuit, device, apparatus, structure, layer, material, or the like) is referred to as being "on," "coupled to," or "connected to" another element, the elements can be directly on, directly coupled to, or directly connected to each other, or intervening elements may be present. In contrast, when an element is referred to as being "directly on," "directly coupled to," or "directly connected to" another element, there are no intervening elements present.

The terms "include" and "comprise" as well as derivatives and variations thereof, in all of their syntactic contexts, are to be construed without limitation in an open, inclusive sense, (e.g., "including, but not limited to"). The term "or," is inclusive, meaning and/or. The phrases "associated with" and "associated therewith," as well as derivatives thereof, can be understood as meaning to include, be included within, interconnect with, contain, be contained within, connect to or with, couple to or with, be communicable with, cooperate with, interleave, juxtapose, be proximate to, be bound to or with, have, have a property of, or the like.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the present disclosure, the terms first, second, etc., may be used to describe various elements, however, these elements are not be limited by these terms unless the context clearly requires such limitation. These terms are only used to distinguish one element from another. For example, a first machine could be termed a second machine, and, similarly, a second machine could be termed a first machine, without departing from the scope of the inventive concept.

The singular forms "a," "an," and "the" in the present disclosure include plural referents unless the content and context clearly dictates otherwise. The conjunctive terms, "and" and "or" are generally employed in the broadest sense to include "and/or" unless the content and context clearly dictates inclusivity or exclusivity as the case may be. The composition of "and" and "or" when recited herein as "and/or" encompasses an embodiment that includes all of the elements associated thereto and at least one more alternative embodiment that includes fewer than all of the elements associated thereto.

In the present disclosure, conjunctive lists make use of a comma, which may be known as an Oxford comma, a Harvard comma, a serial comma, or another like term. Such lists are intended to connect words, clauses or sentences such that the thing following the comma is also included in the list.

The headings and Abstract of the Disclosure provided herein are for convenience only and do not interpret the scope or meaning of the embodiments.

The disinfection systems described in the present disclosure provide several technical effects and advances to the field of target article disinfection. The target articles may be medical devices, such as ultrasound and other imaging probes, invasive medical procedure instruments, dental tools, and the like. A non-limiting set of technical effects and benefits includes the ability to verify when a target article is properly aligned and contained in a UV-transparent disinfection tray and the ability to verify when the UV-transparent disinfection tray is properly aligned in a disinfection chamber. When the disinfection tray includes a controller, the controller of the disinfection tray can communicate information identifying the disinfection tray, the target article, or both the disinfection tray and the target article to the disinfection chamber, and this information can be used to control the disinfection process.

The various embodiments described above can be combined to provide further embodiments. Various features of the embodiments are optional, and, features of one embodiment may be suitably combined with other embodiments. Aspects of the embodiments can be modified, if necessary to employ concepts of the various patents, application and publications to provide yet further embodiments.

Example A-1 is a disinfection tray device, comprising: a tray portion formed from a UV-transparent material, the tray portion having a receptacle arranged therein to receive a target article to be disinfected, wherein the receptacle has a first defined shape and a first defined dimension; and an alignment portion having a second defined shape and a second defined dimension.

Example A-2 may include the subject matter of Example A-1, and alternatively or additionally any other example herein, wherein the receptacle is arranged to receive only a portion of the target article to be disinfected.

Example A-3 may include the subject matter of any of Examples A-1 to A-2, and alternatively or additionally any other example herein, wherein the second defined shape is a cuboid, a square, a rectangle, a rectangular parallelepiped, a convex polyhedron bounded by six quadrilateral faces, a rectangular box, or some other defined shape.

Example A-4 may include the subject matter of any of Examples A-1 to A-3, and alternatively or additionally any other example herein, wherein the target article to be disinfected is a probe, a medical dental instrument, cable, a handle, or some other article to be disinfected.

Example A-5 may include the subject matter of any of Examples A-1 to A-4, and alternatively or additionally any other example herein, wherein the UV-transparent material includes at least one of a plastic, a glass such as quartz, a gel, a polymer, a polymethyl methacrylate (PMMA), and a polystyrene.

Example A-6 may include the subject matter of any of Examples A-1 to A-5, and alternatively or additionally any other example herein, wherein the tray portion is arranged for use a single time.

Example A-7 may include the subject matter of any of Examples A-1 to A-6, and alternatively or additionally any other example herein, wherein the disinfection device is a disposable device.

Example A-8 may include the subject matter of any of Examples A-1 to A-7, and alternatively or additionally any other example herein, wherein the tray portion is at least 50 percent (50%) UV-transparent.

Example A-9 may include the subject matter of any of Examples A-1 to A-8, and alternatively or additionally any other example herein, wherein the tray portion is at least 75 percent (75%) UV-transparent.

Example A-10 may include the subject matter of any of Examples A-1 to A-9, and alternatively or additionally any other example herein, wherein the tray portion is at least 95 percent (95%) UV-transparent.

Example A-11 may include the subject matter of any of Examples A-1 to A-10, and alternatively or additionally any other example herein, wherein the tray portion is a molded structure, a blow-molded structure, a laser-cut structure, or a heat-formed structure.

Example A-12 may include the subject matter of any of Examples A-1 to A-11, and alternatively or additionally any other example herein, further comprising: at least two handle attachment structures.

Example A-13 may include the subject matter of Example A-12, and alternatively or additionally any other example herein, further comprising: at least two handles, wherein each of said at least two handles is arranged for removable coupling to a corresponding handle attachment structure.

Example A-14 may include the subject matter of any of Examples A-1 to A-13, and alternatively or additionally any other example herein, wherein the alignment portion includes at least one registration feature.

Example A-15 may include the subject matter of any of Examples A-1 to A-14, and alternatively or additionally any other example herein, wherein the at least one registration feature is an electronic registration feature.

Example A-16 may include the subject matter of any of Examples A-1 to A-15, and alternatively or additionally any other example herein, wherein the electronic registration feature includes at least one time-of-flight sensor or at least one photo-diode.

Example A-17 may include the subject matter of any of Examples A-1 to A-16, and alternatively or additionally any other example herein, further comprising: a lid arranged to cover at least the receptacle.

Example A-18 may include the subject matter of any of Examples A-1 to A-18, and alternatively or additionally any other example herein, further comprising: at least one UV sensor.

Example A-19 may include the subject matter of any of Examples A-1 to A-18, and alternatively or additionally any other example herein, further comprising: an electronics module, the electronics module having; a communications interface; a user interface (e.g., an audio interface, visual interface, or a tactile user interface); at least one clean/not clean indicator (e.g., red/green indicator); time of last clean indicator (e.g., is the disinfection "expired" or not); a door closed sensor; a serial number or other identifier; an encryption/decryption module; and an aligned-in-chamber module.

Example A-20 may include the subject matter of any of Examples A-1 to A-19, and alternatively or additionally any other example, wherein the electronics module is hermetically sealed in the tray portion.

Example A-21 may include the subject matter of any of Examples A-1 to A-20, and alternatively or additionally any other example herein, wherein the electronics module is arranged to communicate identification information associated with the target article to be disinfected from the disinfection device to a disinfection system.

Example A-22 may include the subject matter of any of Examples A-1 to A-21, and alternatively or additionally any other example herein, further comprising: a mechanically sealable case arranged to hold at least one tray, the mechanically sealable case arranged to store the at least one target article to be disinfected.

Example B-1 is a disinfection device, comprising: a tray having at least one pre-formed compartment arranged to contain at least a portion of a target article to be disinfected, the tray having at least one registration structure arranged to cooperate with a corresponding registration structure inside a disinfection chamber, wherein the tray is formed at least in part from a UV-transparent material.

Example B-2 may include the subject matter of Example B-1, and alternatively or additionally any other example herein, further comprising: a controller arranged to communicate identification information to a controller associated with the disinfection chamber, wherein the identification information is associated with at least one of the tray and the target article to be disinfected.

Example B-3 may include the subject matter of any of Examples B-1 to B-2, and alternatively or additionally any other example herein, wherein the controller is arranged to determine whether or not the target article to be disinfected is properly aligned in the pre-formed compartment.

Example B-4 may include the subject matter of any of Examples B-1 to B-3, and alternatively or additionally any other example herein, wherein the controller is arranged to determine whether or not the tray is properly aligned inside the disinfection chamber.

Example B-5 may include the subject matter of any of Examples B-1 to B-4, and alternatively or additionally any other example herein, wherein the UV-transparent material is transparent to UV-C radiation.

Example B-6 may include the subject matter of any of Examples B-1 to B-5, and alternatively or additionally any other example herein, wherein UV-transparent material is at least 50 percent (50%) UV-transparent.

Example B-7 may include the subject matter of any of Examples B-1 to B-6, and alternatively or additionally any other example herein, wherein the at least one registration structure is a protuberance arranged to mate with a corresponding indenture inside the disinfection chamber or wherein the at least one registration structure is an indenture arranged to mate with a corresponding protuberance inside the disinfection chamber.

Example B-8 may include the subject matter of any of Examples B-1 to B-7, and alternatively or additionally any other example herein, wherein the at least one registration structure is a first electronic registration structure arranged to mate with a corresponding second electronic registration structure inside the disinfection chamber.

Example B-9 may include the subject matter of Example B-8, and alternatively or additionally any other example herein, wherein the first and electronic registration structures include at least one of optical circuitry, radio frequency (RF) circuitry, induction circuitry, or electric continuity circuitry.

Example B-10 may include the subject matter of any of Examples B-1 to B-9, and alternatively or additionally any other example herein, further comprising: a case having a lid, the case arranged to contain the tray before a disinfection process and after a disinfection process.

Example C-1 is a disinfection device, comprising: arranging a target article to be disinfected in a tray having at least one pre-formed receptacle arranged therein to receive the target article, wherein the tray is formed at least in part from a UV-transparent material; arranging the tray in a disinfection chamber, wherein arranging the tray includes cooperatively aligning a registration feature of the tray with a corresponding registration feature of the disinfection chamber; and executing a UV-based disinfection process within the disinfection chamber.

Example C-2 may include the subject matter of Example C-1, and alternatively or additionally any other example herein, further comprising: determining a misalignment condition, said determining the misalignment condition by: electronically determining whether or not the target article to be disinfected is properly aligned in the at least one pre-formed receptacle; or electronically determining whether or not the tray is properly aligned in the disinfection chamber; and providing an output indication representing the misalignment condition.

Example C-3 may include the subject matter of any of Examples C-1 to C-2, and alternatively or additionally any other example herein, further comprising: determining a misalignment condition, said determining the misalignment condition by: visually determining whether or not the target article to be disinfected is properly aligned in the at least one pre-formed receptacle; and tactilely determining whether or not the tray is properly aligned in the disinfection chamber.

Example C-4 may include the subject matter of any of Examples C-1 to C-3, and alternatively or additionally any other example herein, further comprising: communicating identification information to the disinfection chamber, the identification information representing at least one of the tray and the target article to be disinfected; and using the identification information to select the UV-based disinfection process.

Example C-5 may include the subject matter of any of Examples C-1 to C-4, and alternatively or additionally any other example herein, further comprising: generating metadata associated with the disinfection process; and communicating the metadata to a remote computing device.

Example C-6 may include the subject matter of Example C-5, and alternatively or additionally any other example herein, wherein the metadata includes at least one of: time information representing when the disinfection process was executed, date information representing when the disinfection process was executed, and user identification information.

Example C-7 may include the subject matter of Example C-5, and alternatively or additionally any other example herein, wherein the metadata includes date information representing when the disinfection will expire.

Example C-8 may include the subject matter of any of Examples C-1 to C-7, and alternatively or additionally any other example herein, further comprising: extending the disinfection process based on accumulated radiation information derived from at least one radiation sensor.

Example C-9 may include the subject matter of any of Examples C-1 to C-8, and alternatively or additionally any other example herein, further comprising: individually controlling a plurality of radiation sources in the disinfection chamber based on at least one of the tray and the target article to be disinfected, wherein individually controlling the plurality of radiation sources includes directing a first radiation source to output radiation for a first period of time and directing a second radiation source to output radiation for a second period of time, the first period of time being different from the second period of time.

Example C-10 may include the subject matter of any of Examples C-1 to C-9, and alternatively or additionally any other example herein, wherein arranging the target article to be disinfected in the tray having at least one pre-formed receptacle includes aligning the target article to be disinfected on a surface of the tray according to a template printed on the surface of the tray.

Example C-11 may include the subject matter of any of Examples C-1 to C-10, and alternatively or additionally any other example herein, wherein the at least one pre-formed receptacle includes a plurality of clips arranged to bind certain portions of the target article to be disinfected.

Example C-12 may include the subject matter of any of Examples C-1 to C-11, and alternatively or additionally any other example herein, further comprising: verifying disinfection of the target article to be disinfected after executing at least a portion of the UV-based disinfection process.

Example C-13 may include the subject matter of Example C-12, and alternatively or additionally any other example herein, wherein the verifying includes: sensing UV-radiation with at least one radiation sensor associated with the tray.

Example C-14 may include the subject matter of any of Examples C-1 to C-13, and alternatively or additionally any other example herein, wherein the registration feature of the tray and the corresponding registration feature of the disinfection chamber are formed at least in part by electronic devices.

Example C-15 may include the subject matter of Example C-14, and alternatively or additionally any other example herein, wherein the electronic devices are arranged to form an optical connection, a wireless radio connection, an electromagnetic connection, or an inductive connection.

Example C-16 may include the subject matter of any of Examples C-1 to C-15, and alternatively or additionally any other example herein, further comprising: removing at least one handle structure from the tray after arranging the tray in the disinfection chamber.

Example D-1 is a disinfection device, comprising: a controller; and a UV-transparent structure, the UV-transparent structure having a multi-compartment receptacle formed therein, the UV-transparent structure shaped to align and contain a certain type of target article to be disinfected.

Example D-2 may include the subject matter of Example D-1, and alternatively or additionally any other example herein, wherein the controller is arranged to communicate identification information to a disinfection chamber, the identification information representing at least one of the tray and the target article to be disinfected.

Example D-3 may include the subject matter of any of Examples D-1 to D-2, and alternatively or additionally any other example herein, wherein the UV-transparent structure includes: a plurality of registration features, various ones of the registration features arranged to mate with corresponding registration features in a disinfection chamber.

Example D-4 may include the subject matter of Example D-3, and alternatively or additionally any other example herein, wherein the plurality of registration features are non-electronic, physical structures.

Example D-4 may include the subject matter of Example D-3, and alternatively or additionally any other example herein, wherein the plurality of registration features are electronic registration features.

Example D-6 may include the subject matter of any of Examples D-1 to D-5, and alternatively or additionally any other example herein, further comprising: a radiation sensor arranged to provide information representing an amount of radiation received during a disinfection process.

Example D-7 may include the subject matter of Example D-6, and alternatively or additionally any other example herein, wherein the radiation sensor includes at least one electronic photo sensor.

Example D-8 may include the subject matter of Example D-6, and alternatively or additionally any other example herein, wherein the radiation sensor includes at least one radiation sensitive material arranged to change color based on the amount of radiation received during the disinfection process.

Example D-9 may include the subject matter of any of Examples D-1 to D-8, and alternatively or additionally any other example herein, wherein the multi-compartment receptacle includes: a plurality of clips suitably arranged on a printed outline of the target article to be disinfected.

Example D-10 may include the subject matter of any of Examples D-1 to D-9, and alternatively or additionally any other example herein, wherein the multi-compartment receptacle includes: a plurality of receptacle portions formed below a surface of the UV-transparent structure.

Example D-11 may include the subject matter of any of Examples D-1 to D-10, and alternatively or additionally any other example herein, wherein the UV-transparent structure is a molded plastic structure.

Example D-12 may include the subject matter of any of Examples D-1 to D-11, and alternatively or additionally any other example herein, wherein the UV-transparent structure is arranged for a plurality of disinfection cycles.

Example D-13 may include the subject matter of any of Examples D-1 to D-12, and alternatively or additionally any other example herein, wherein the UV-transparent structure is a disposable structure arranged for a single disinfection cycle.

Example D-14 may include the subject matter of any of Examples D-1 to D-13, and alternatively or additionally any other example herein, wherein the UV-transparent structure is arranged for sealed long-term storage.

Example D-15 may include the subject matter of any of Examples D-1 to D-14, and alternatively or additionally any other example herein, wherein the controller is integrated inside the UV-transparent structure.

Example E-1 is a disinfection device, comprising: a disinfection chamber, the disinfection chamber having: an interior volume; a plurality of radiation sources, which, when enabled, output a disinfecting radiation; at least one disinfection chamber registration feature; and a disinfection chamber controller arranged to perform a disinfection process via enablement of the plurality of radiation sources; and a disinfection tray device, the disinfection tray device having: a UV-transparent tray structure, the UV-transparent tray structure having a multi-compartment receptacle shaped to align and contain a certain type of target article to be disinfected.

Example E-2 may include the subject matter of Example E-1, and alternatively or additionally any other example herein, wherein the disinfection device further comprises: at least one disinfection tray registration feature, the at least one disinfection tray registration feature arranged to cooperate with the at least one disinfection chamber registration feature when the disinfection tray device is placed in the disinfection chamber.

Example E-3 may include the subject matter of Example E-2, and alternatively or additionally any other example herein, wherein the at least one disinfection tray registration feature is a non-electronic, physical structure.

Example E-4 may include the subject matter of Example E-3, and alternatively or additionally any other example herein, wherein a proper alignment of the disinfection tray device in the disinfection chamber is indicated via tactile feedback.

Example E-5 may include the subject matter of Example E-2, and alternatively or additionally any other example herein, wherein the at least one disinfection tray registration feature is an electronic registration feature.

Example E-6 may include the subject matter of Example E-5, and alternatively or additionally any other example herein, wherein a state of proper alignment or improper alignment of the disinfection tray device in the disinfection chamber is indicated via at least one of an audible output and a visual output.

Example E-7 may include the subject matter of any of Examples E-1 to E-6, and alternatively or additionally any other example herein, wherein the disinfection chamber is arranged to concurrently hold a plurality of disinfection tray devices.

Example E-8 may include the subject matter of any of Examples E-1 to E-7, and alternatively or additionally any other example herein, wherein the disinfection tray device is arranged to concurrently align and contain a plurality of target articles to be disinfected.

Example E-9 may include the subject matter of any of Examples E-1 to E-8, and alternatively or additionally any other example herein, wherein the disinfection chamber device further comprises: a door; and a door sensor, wherein the disinfection chamber controller is arranged to determine when the door is closed and wherein the disinfection chamber controller is further arranged to prevent and suspend the disinfection process when the door sensor indicates that the door is open.

Example E-10 may include the subject matter of Example E-9, and alternatively or additionally any other example herein, wherein the disinfection chamber device further comprises: a second door; and a second door sensor, wherein the disinfection chamber controller is arranged to determine when both the door and the second door are closed and wherein the disinfection chamber controller is further arranged to prevent and suspend the disinfection process when the door sensor indicates that the door is open or when the second door sensor indicates that the second door is open.

Example E-11 may include the subject matter of Example E-10, and alternatively or additionally any other example herein, wherein the disinfection chamber device further comprises: a first door lock mechanism arranged to lock the door and arranged to unlock the door; and a second door lock mechanism arranged to lock the second door and arranged to unlock the second door, wherein the disinfection chamber controller is arranged to: determine a pre-disinfection state, said pre-disinfection state being a first time before the disinfection process begins; determine a current disinfection state, said current disinfection state being a second time when the disinfection process has started and the disinfection process has not completed; determine a post-disinfection state, said post-disinfection state being a third time when the disinfection process has completed; unlock the door during the pre-disinfection state; lock the second door during the pre-disinfection state; lock both the door and the second door during the current disinfection state; lock the door during the post-disinfection state; and unlock the second door during the post-disinfection state.

Example E-12 may include the subject matter of Example E-11, and alternatively or additionally any other example herein, wherein the disinfection chamber is integrated into a wall.

Example E-13 may include the subject matter of Example E-12, and alternatively or additionally any other example herein, wherein a first side of the wall exposes the door and wherein a second opposing side of the wall exposes the second door, said first side of the wall being a pre-disinfected side of the wall and said second side opposing side of the wall being a post-disinfected side of the wall.

Example E-14 may include the subject matter of any of Examples E-1 to E-3, and alternatively or additionally any other example herein, wherein the disinfection tray device further comprises: a disinfection tray controller, the disinfection tray controller arranged to communicate identification information to the disinfection chamber controller, the identification information representing at least one of the UV-transparent tray structure and the certain type of target article to be disinfected.

Example E-15 may include the subject matter of Example E-14, and alternatively or additionally any other example herein, wherein the disinfection chamber controller is further arranged to: select the disinfection process from a plurality of disinfection processes based on the identification information.

Example E-16 may include the subject matter of Example E-14, and alternatively or additionally any other example herein, wherein the disinfection chamber controller is further arranged to: control the disinfection process based on the identification information.

Example E-17 may include the subject matter of Example E-14, and alternatively or additionally any other example herein, wherein the disinfection chamber controller is further arranged to: selectively enable a first one of the plurality of radiation sources and concurrently a disable a second one of the plurality of radiation sources during the disinfection process based on the identification information.

Example E-18 may include the subject matter of any of Examples E-1 to E-17, and alternatively or additionally any other example herein, wherein the disinfection chamber controller is further arranged to: generate metadata based on the disinfection process; and communicate at least some of the metadata to a remote computing device.

Example E-19 may include the subject matter of Example E-18, and alternatively or additionally any other example herein, wherein the metadata includes user identification information representing an identity of a user that initiated the disinfection process.

Example E-20 may include the subject matter of Example E-18, and alternatively or additionally any other example herein, wherein the metadata includes timestamp information representing a date when the disinfection process was executed.

Example E-21 may include the subject matter of Example E-18, and alternatively or additionally any other example herein, wherein the disinfection chamber controller is further arranged to: generate an expiration date associated with the disinfection process.

Example E-22 may include the subject matter of any of Examples E-1 to E-21, and alternatively or additionally any other example herein, wherein the disinfection tray device further comprises: at least one electronic radiation sensor integrated into a surface of the disinfection tray device.

Example E-23 may include the subject matter of Example E-22, and alternatively or additionally any other example herein, wherein the disinfection chamber controller is further arranged to: disable the plurality of radiation sources based on information from the at least one electronic radiation sensor.

Example E-24 may include the subject matter of any of Examples E-1 to E-24, and alternatively or additionally any other example herein, wherein the disinfection tray device further comprises: a first electronic radiation sensor integrated into a surface of the disinfection tray device at a first location proximal to a first receptacle portion of the UV-transparent tray structure; and a second electronic radiation sensor integrated into the surface of the disinfection tray device at a second location proximal to a second receptacle portion of the UV-transparent tray structure.

Example E-25 may include the subject matter of Example E-22, and alternatively or additionally any other example herein, wherein the disinfection chamber controller is further arranged to: selectively enable and disable a first one of the plurality of radiation sources based on information from the first electronic radiation sensor; and selectively enable and disable a second one of the plurality of radiation sources based on information from the second electronic radiation sensor.

Example F-1 is a non-transitory computer-readable storage medium whose stored contents configure a disinfection system to perform a method, the method comprising: determining whether a target article to be disinfected is properly aligned in a tray portion of a disinfection tray device, the tray portion formed of a UV-transparent material, the tray portion having a receptacle shaped to align and contain at least a portion of the target article to be disinfected; and communicating identification information associated with at least one of the tray portion and the target article to be disinfected to a disinfection device.

Example F-2 may include the subject matter of Example F-1, and alternatively or additionally any other example herein, wherein the method further comprises: selecting a disinfection process from a plurality of available disinfection processes based on the identification information.

Example F-3 may include the subject matter of Example F-2, and alternatively or additionally any other example herein, wherein the method further comprises: terminating the selected disinfection process based on data from at least one radiation sensor integrated in the disinfection tray device.

Example F-4 may include the subject matter of Example F-2, and alternatively or additionally any other example herein, the method further comprises: performing the selected disinfection process based on at least one alignment status indicator.

Example F-5 may include the subject matter of Example F-4, and alternatively or additionally any other example herein, wherein the alignment status indicator is generated based on a proper alignment of the disinfection tray device in the disinfection device.

The various embodiments described above can be combined to provide further embodiments. Aspects of the embodiments can be modified, if necessary to employ concepts of the various patents, application and publications to provide yet further embodiments.

For example other UV-transparent receptacle device may be designed for allowing at least a part of at least an instrument to be disinfected, to lay in an adapted position for an high-level disinfection.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

It would be understood that the arrangement of the UV-transparent receptacle enables an exposure of all points of interest of the medical instrument to be disinfected, in particular of the cold points of the instrument, to a dose of UV sufficient to reach a High Level Disinfection (as defined by the Centers for Disease Control and Prevention, known as CDC) and minimize the differences in illumination between the different points (maximizing the homogeneity of the exposure). In addition, the features of the UV-transparent receptacle makes it possible to be in conformity with the forecasts resulting from one or more tests and/or from one or more optical simulation, which determine the exposure thresholds (dose or time) necessary to carry out a high level disinfection of the instrument and in particular of its cold spot which comes from the interaction between the geometric shape of the instrument, its positioning in the enclosure, the characteristics of the enclosure.

Moreover, the physical features (transparency, shape, positioning) of the disinfection system are such that they allow a control system based on one or more optical sensors to be sensitive to variations in the optical properties of the elements of the disinfection chamber (for example, the emissivity of the sources, the reflectivity of the walls, the transparency of the receptacle) in order to measure one or more doses which will have to equal or exceed one or more thresholds for the system to validate an HLD cycle.

The invention claimed is:

1. A disinfection system for a reusable medical instrument, comprising:
   (a) a disinfection chamber, the disinfection chamber comprising:
      an interior volume;
      at least one radiation source, which, when enabled, output an UV disinfecting radiation, the at least one radiation source being suitable for emitting sufficient UV disinfecting radiation to carry out high-level disinfection; and
      a disinfection chamber controller configured to perform an high-level disinfection process via enablement of the at least one radiation source;

(b) a disinfection device suitable to be placed into the disinfection chamber, the disinfection device comprising at least one UV-transparent receptacle for receiving at least a part of at least one reusable medical instrument to be disinfected, the at least one UV-transparent receptacle being arranged for a specific orientation and placement of the at least one reusable medical instrument to be disinfected; and (c) a device for determining if the reusable medical instrument is properly aligned in the disinfection device.

2. The disinfection system of claim 1, wherein the at least one UV-transparent receptacle is arranged in a disinfection device, the disinfection device comprising at least one first registration feature, the at least one first registration feature enabling the alignment of the instrument to be disinfected into the at least one UV-transparent receptacle.

3. The disinfection system of claim 2, wherein the at least one first registration feature is a non-electronic, physical structure, such as a template printed on the surface of the UV-transparent receptacle.

4. The disinfection system of claim 2, wherein the at least one registration feature is an electronic registration feature.

5. The disinfection system of claim 1, wherein the at least one UV-transparent receptacle is arranged in a disinfection device, the disinfection chamber comprises at least one disinfection chamber registration feature, the disinfection device comprises at least one second disinfection registration feature, the at least one second disinfection registration feature being configured to cooperate with the at least one disinfection chamber registration feature when the disinfection device is placed in the disinfection chamber.

6. The disinfection system of claim 5, wherein the at least one second registration feature and/or the at least one disinfection chamber is a non-electronic, physical structure.

7. The disinfection system of claim 1, wherein the at least one UV-transparent receptacle is arranged in a disinfection device, and the disinfection device further comprises:

a disinfection controller, the disinfection controller being arranged to communicate identification information to the disinfection chamber controller, the identification information representing at least one of the UV-transparent receptacle and the certain type of instrument to be disinfected.

8. The disinfection system of claim 7, wherein the disinfection chamber controller is further arranged to:

select the disinfection process from a plurality of disinfection processes based on the identification information.

9. The disinfection system of claim 7, wherein the disinfection chamber controller is further arranged to:

control the disinfection process based on the identification information.

10. The disinfection system of claim 1, wherein the disinfection device further comprises:

at least one electronic radiation sensor integrated into a surface of the disinfection device.

11. The disinfection system of claim 10, wherein the disinfection chamber controller is further arranged to:

disable the at least one radiation source based on information from the at least one electronic radiation sensor.

12. The disinfection system of claim 1, wherein the at least one UV-transparent receptacle is arranged in a disinfection device, and the disinfection device further comprises:

a first electronic radiation sensor integrated into a surface of the disinfection device at a first location proximal to a first receptacle portion of the UV-transparent receptacle; and 'a second electronic radiation sensor integrated into the surface of the disinfection device at a second location proximal to a second receptacle portion of the UV-transparent receptacle.

13. The disinfection system of claim 12, wherein the disinfection chamber comprises a plurality of radiation source, the disinfection chamber controller being further arranged to:

selectively enable and disable a first one of the plurality of radiation sources based on information from the first electronic radiation sensor; and selectively enable and disable a second one of the plurality of radiation sources based on information from the second electronic radiation sensor.

14. The disinfection system of claim 1, wherein the device for determining if the reusable medical instrument is properly aligned comprises an element suitable for verifying a proper alignment of the disinfection device in the disinfection chamber and/or a proper alignment of the instrument to be disinfected into the UV-transparent receptacle, the element being suitable for analyzing data from a sensor.

15. The disinfection system of claim 1, wherein the disinfection chamber controller is configured to enable the at least one radiation source so as to emit a dose of radiation comprised between 10 Millijoules per square centimeter and 10 Joules per square centimeter for a duration comprised between 10 seconds and 10 minutes.

16. The disinfection system of claim 1, wherein the disinfection chamber controller is configured to create a plurality of disinfection regions within the interior volume, the disinfection chamber controller being configured to enable the at least one radiation source in order to irradiate the disinfection regions at a varying radiation intensity, at least one region being irradiated two or three time the radiation intensity of another region.

17. The disinfection system of claim 1, wherein the at least one UV-transparent receptacle is arranged in a disinfection device, the UV-transparent receptacle further being arranged such that the instrument to be disinfected is oriented substantially horizontally in the disinfection chamber, when the disinfection device is positioned into the disinfection chamber.

18. The disinfection system of claim 1, wherein the instrument to be disinfected can be fitted into the UV-transparent receptacle according to a predetermined path, allowing an optical pathway of UV photons to perform and control high level disinfection.

19. A method for disinfecting reusable medical instruments, comprising:

a) arranging a reusable medical instrument to be disinfected in a disinfection device having at least one pre-formed receptacle arranged therein to receive said reusable medical instrument to be disinfected, wherein the disinfection device is at least partially formed from a UV-transparent material and the at least one receptacle is arranged for a specific orientation and placement of the reusable medical instrument to be disinfected;

b) determining whether the reusable medical instrument to be disinfected is properly aligned in the disinfection device;

c) placing the disinfection device in a disinfection chamber, wherein the disinfection chamber comprises:

i) an interior volume;

ii) at least one radiation source, which, when enabled, outputs an UV disinfecting radiation, the at least one radiation source being suitable for emitting sufficient UV disinfecting radiation to carry out high-level disinfection; and iii) a disinfection chamber controller configured to perform a high-level disinfection process via enablement of the at least one radiation source; and d) executing the high-level disinfection process on the reusable medical instrument within the disinfection device in the disinfection chamber.

20. The method for disinfecting reusable medical instruments according to claim 19 wherein a state of proper alignment or improper alignment of the disinfection device in the disinfection chamber is indicated via an audible output or a visual output.

21. The method for disinfecting reusable medical instruments according to claim 19 wherein a proper alignment of the disinfection device in the disinfection chamber is indicated via tactile feedback.

* * * * *